US011433140B2

(12) United States Patent
Lerchen et al.

(10) Patent No.: US 11,433,140 B2
(45) Date of Patent: Sep. 6, 2022

(54) SPECIFIC ANTIBODY DRUG CONJUGATES (ADCS) HAVING KSP INHIBITORS

(71) Applicant: Bayer Pharma Aktiengesellschaft, Berlin (DE)

(72) Inventors: Hans-Georg Lerchen, Leverkusen (DE); Anne-Sophie Rebstock, Champagne au Mont d'Or (FR); Beatrix Stelte-Ludwig, Wülfrath (DE); Dennis Kirchhoff, Berlin (DE); Sandra Berndt, Hohen Neuendorf (DE); Lisa Dietz, Wuppertal (DE); Stephan Märsch, Cologne (DE); Stefanie Hammer, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 152 days.

(21) Appl. No.: 16/472,682

(22) PCT Filed: Dec. 18, 2017

(86) PCT No.: PCT/EP2017/083313
§ 371 (c)(1),
(2) Date: Jun. 21, 2019

(87) PCT Pub. No.: WO2018/114804
PCT Pub. Date: Jun. 28, 2018

(65) Prior Publication Data
US 2019/0365916 A1 Dec. 5, 2019

(30) Foreign Application Priority Data
Dec. 21, 2016 (EP) ..................................... 16205870

(51) Int. Cl.
*A61K 39/00* (2006.01)
*A61K 47/65* (2017.01)
*A61K 47/68* (2017.01)
*A61P 35/02* (2006.01)
*A61P 35/00* (2006.01)
*A61K 39/395* (2006.01)
*A61K 45/06* (2006.01)
*C07K 16/28* (2006.01)

(52) U.S. Cl.
CPC .......... *A61K 47/65* (2017.08); *A61K 39/3955* (2013.01); *A61K 45/06* (2013.01); *A61K 47/6849* (2017.08); *A61P 35/00* (2018.01); *A61P 35/02* (2018.01); *C07K 16/2866* (2013.01); *A61K 2039/505* (2013.01); *C07K 2317/24* (2013.01); *C07K 2317/565* (2013.01); *C07K 2317/73* (2013.01); *C07K 2317/76* (2013.01)

(58) Field of Classification Search
CPC ................ A61K 47/65; A61K 47/6849; A61K 2039/505; A61K 47/6889; A61K 47/6803; A61P 35/00; C07K 16/2866; C07K 2317/73

See application file for complete search history.

(56) References Cited

U.S. PATENT DOCUMENTS

| | | | |
|---|---|---|---|
| 4,399,216 A | 8/1983 | Axel et al. | |
| 4,474,893 A | 10/1984 | Reading | |
| 4,510,245 A | 4/1985 | Cousens et al. | |
| 4,634,665 A | 1/1987 | Axel et al. | |
| 4,714,681 A | 12/1987 | Reading | |
| 4,816,397 A | 3/1989 | Boss et al. | |
| 4,816,567 A | 3/1989 | Cabilly et al. | |
| 4,925,648 A | 5/1990 | Hansen et al. | |
| 4,968,615 A | 11/1990 | Koszinowski et al. | |
| 5,168,062 A | 12/1992 | Stinski | |
| 5,179,017 A | 1/1993 | Axel et al. | |
| 5,270,163 A | 12/1993 | Gold et al. | |
| 5,573,920 A | 11/1996 | Randle | |
| 5,601,819 A | 2/1997 | Wong et al. | |
| 6,177,078 B1 | 1/2001 | Lopez | |
| 7,318,924 B2 | 1/2008 | McKenzie et al. | |
| 7,465,449 B2 | 12/2008 | Violette et al. | |
| 7,598,350 B2 | 10/2009 | Liu et al. | |
| 7,628,986 B2 | 12/2009 | Weber et al. | |
| 7,662,581 B1 | 2/2010 | Bussiere et al. | |
| 10,022,453 B2 | 7/2018 | Lerchen et al. | |
| 10,485,880 B2 | 11/2019 | Lerchen et al. | |

(Continued)

FOREIGN PATENT DOCUMENTS

| CA | 2990411 A1 | 12/2016 |
|---|---|---|
| CA | 2990411 A1 | 12/2016 |

(Continued)

OTHER PUBLICATIONS

Strome et al., The Oncologist, 2007; 12:1084-95 (Year: 2007).*

(Continued)

*Primary Examiner* — Sheela J. Huff
(74) *Attorney, Agent, or Firm* — Wilson Sonsini Goodrich & Rosati

(57) ABSTRACT

Specific binder-drug conjugates (ADCs) of kinesin spindle protein inhibitors, effective metabolites of these ADCs, processes for preparing these ADCs, the use of these ADCs for the treatment and/or prevention of diseases and to the use of these ADCs for preparing medicaments for treatment and/or prevention of diseases, in particular hyperproliferative and/or angiogenic disorders such as, for example, cancer diseases, are described.

9 Claims, 13 Drawing Sheets
Specification includes a Sequence Listing.

(56) References Cited

U.S. PATENT DOCUMENTS

| | | |
|---|---|---|
| 10,744,205 B2 | 8/2020 | Lerchen et al. |
| 10,973,923 B2 | 4/2021 | Lerchen et al. |
| 11,001,636 B2 | 5/2021 | Lerchen et al. |
| 11,071,788 B2 | 7/2021 | Lerchen et al. |
| 11,123,439 B2 | 9/2021 | Lerchen et al. |
| 2007/0264253 A1 | 11/2007 | Liu et al. |
| 2008/0193445 A1 | 8/2008 | Goetsch et al. |
| 2009/0175796 A1 | 7/2009 | Raitano et al. |
| 2010/0028947 A1 | 2/2010 | Goletz et al. |
| 2012/0128688 A1* | 5/2012 | Lillard .................. A61P 35/02 424/158.1 |
| 2013/0066055 A1 | 3/2013 | Lerchen et al. |
| 2014/0322247 A1 | 10/2014 | Barsanti et al. |
| 2015/0352224 A1 | 12/2015 | Naito et al. |
| 2016/0346402 A1 | 12/2016 | Lerchen et al. |
| 2018/0015176 A1 | 1/2018 | Lerchen et al. |
| 2018/0169256 A1 | 6/2018 | Lerchen et al. |
| 2018/0185510 A1 | 7/2018 | Lerchen et al. |
| 2018/0318437 A1 | 11/2018 | Lerchen et al. |
| 2018/0318438 A1 | 11/2018 | Lerchen et al. |
| 2019/0077752 A1 | 3/2019 | Lerchen et al. |
| 2019/0328897 A1 | 10/2019 | Lerchen et al. |
| 2019/0330357 A1 | 10/2019 | Lerchen et al. |
| 2019/0351066 A1 | 11/2019 | Lerchen et al. |
| 2020/0138970 A1 | 5/2020 | Lerchen et al. |
| 2021/0230284 A1 | 7/2021 | Lerchen et al. |

FOREIGN PATENT DOCUMENTS

| | | |
|---|---|---|
| CA | 3018630 A1 | 9/2017 |
| CA | 3018630 A1 | 9/2017 |
| EP | 0586002 A2 | 3/1994 |
| EP | 0586002 A2 | 3/1994 |
| EP | 0712863 A1 | 5/1996 |
| EP | 0712863 A1 | 5/1996 |
| EP | 0719859 A1 | 7/1996 |
| EP | 0719859 A1 | 7/1996 |
| EP | 1735348 A1 | 12/2006 |
| EP | 1773884 A2 | 4/2007 |
| EP | 1900750 A1 | 3/2008 |
| EP | 1900750 A1 | 3/2008 |
| EP | 1911766 A1 | 4/2008 |
| EP | 1911766 A1 | 4/2008 |
| EP | 2073842 A2 | 7/2009 |
| EP | 2121008 A2 | 11/2009 |
| EP | 2195023 A1 | 6/2010 |
| EP | 2311879 A2 | 4/2011 |
| EP | 2311879 A2 | 4/2011 |
| EP | 1773884 B1 | 3/2012 |
| EP | 2426148 A1 | 3/2012 |
| EP | 2426148 A1 | 3/2012 |
| EP | 1735348 B1 | 6/2012 |
| EP | 2073842 B1 | 12/2014 |
| EP | 2195023 B1 | 3/2018 |
| JP | 2008524321 A | 7/2008 |
| WO | WO-9000786 A1 | 1/1990 |
| WO | WO-9100360 A1 | 1/1991 |
| WO | WO199100360 A1 | 1/1991 |
| WO | WO-9105871 A1 | 5/1991 |
| WO | WO199105871 A1 | 5/1991 |
| WO | WO-9205793 A1 | 4/1992 |
| WO | WO199205793 A1 | 4/1992 |
| WO | WO-9208802 A1 | 5/1992 |
| WO | WO199208802 A1 | 5/1992 |
| WO | WO-9215683 A1 | 9/1992 |
| WO | WO199215683 A1 | 9/1992 |
| WO | WO-9317715 A1 | 9/1993 |
| WO | WO199317715 A1 | 9/1993 |
| WO | WO-9708320 A1 | 3/1997 |
| WO | WO199708320 A1 | 3/1997 |
| WO | WO-9735616 A1 | 10/1997 |
| WO | WO199735616 A1 | 10/1997 |
| WO | WO-9947554 A1 | 9/1999 |
| WO | WO199947554 A1 | 9/1999 |
| WO | WO-0109192 A1 | 2/2001 |
| WO | WO2001009192 A1 | 2/2001 |
| WO | WO-0162931 A2 | 8/2001 |
| WO | WO2001062931 A2 | 8/2001 |
| WO | WO-0188138 A1 | 11/2001 |
| WO | WO2001088138 A1 | 11/2001 |
| WO | WO-0212501 A2 | 2/2002 |
| WO | WO2002012501 A2 | 2/2002 |
| WO | WO-02077033 A1 | 10/2002 |
| WO | WO2002077033 A1 | 10/2002 |
| WO | WO-02088170 A2 | 11/2002 |
| WO | WO-02092771 A2 | 11/2002 |
| WO | WO2002088170 A2 | 11/2002 |
| WO | WO2002092771 A2 | 11/2002 |
| WO | WO-02100348 A2 | 12/2002 |
| WO | WO2002100348 A2 | 12/2002 |
| WO | WO-03034903 A2 | 5/2003 |
| WO | WO-03040979 A1 | 5/2003 |
| WO | WO2003034903 A2 | 5/2003 |
| WO | WO2003040979 A1 | 5/2003 |
| WO | WO-03049527 A2 | 6/2003 |
| WO | WO2003049527 A2 | 6/2003 |
| WO | WO-03060064 A2 | 7/2003 |
| WO | WO2003060064 A2 | 7/2003 |
| WO | WO-03083041 A2 | 10/2003 |
| WO | WO2003083041 A2 | 10/2003 |
| WO | WO-03106495 A2 | 12/2003 |
| WO | WO2003106495 A2 | 12/2003 |
| WO | WO-2004056847 A2 | 7/2004 |
| WO | WO-2004091375 A2 | 10/2004 |
| WO | WO-2004100873 A2 | 11/2004 |
| WO | WO-2005009369 A2 | 2/2005 |
| WO | WO-2005010151 A2 | 2/2005 |
| WO | WO2004056847 A3 | 6/2005 |
| WO | WO2005009369 A3 | 6/2005 |
| WO | WO2005051922 A1 | 6/2005 |
| WO | WO-2005051922 A1 | 6/2005 |
| WO | WO-2005056606 A2 | 6/2005 |
| WO | WO2004091375 A3 | 7/2005 |
| WO | WO2004100873 A3 | 8/2005 |
| WO | WO2005010151 A3 | 9/2005 |
| WO | WO2005056606 A3 | 9/2005 |
| WO | WO-2005081711 A2 | 9/2005 |
| WO | WO-2005081854 A2 | 9/2005 |
| WO | WO-2005090407 A1 | 9/2005 |
| WO | WO2005090407 A8 | 12/2005 |
| WO | WO2005081854 A3 | 1/2006 |
| WO | WO2006002236 A1 | 1/2006 |
| WO | WO-2006002236 A1 | 1/2006 |
| WO | WO-2006044825 A2 | 4/2006 |
| WO | WO-2006060737 A2 | 6/2006 |
| WO | WO-2006062779 A2 | 6/2006 |
| WO | WO-2006066896 A2 | 6/2006 |
| WO | WO2006066896 A2 | 6/2006 |
| WO | WO-2006074418 A2 | 7/2006 |
| WO | WO-2006089232 A2 | 8/2006 |
| WO | WO2006060737 A3 | 9/2006 |
| WO | WO2006100036 A1 | 9/2006 |
| WO | WO-2006100036 A1 | 9/2006 |
| WO | WO2006044825 A3 | 10/2006 |
| WO | WO2005081711 A2 | 11/2006 |
| WO | WO-2007002222 A1 | 1/2007 |
| WO | WO2007021794 A1 | 2/2007 |
| WO | WO-2007021794 A1 | 2/2007 |
| WO | WO2006089232 A3 | 3/2007 |
| WO | WO-2007024536 A2 | 3/2007 |
| WO | WO2006074418 A3 | 4/2007 |
| WO | WO-2007038637 A2 | 4/2007 |
| WO | WO-2007064759 A2 | 6/2007 |
| WO | WO-2007070538 A2 | 6/2007 |
| WO | WO2007024536 A3 | 7/2007 |
| WO | WO2007002222 A3 | 8/2007 |
| WO | WO2007038637 A3 | 10/2007 |
| WO | WO2006062779 A3 | 1/2008 |
| WO | WO2007064759 A3 | 1/2008 |
| WO | WO2008004834 A1 | 1/2008 |
| WO | WO-2008004834 A1 | 1/2008 |
| WO | WO-2008028686 A2 | 3/2008 |
| WO | WO-2008031056 A2 | 3/2008 |

(56) References Cited

FOREIGN PATENT DOCUMENTS

| | | |
|---|---|---|
| WO | WO-2008036688 A2 | 3/2008 |
| WO | WO-2008047242 A2 | 4/2008 |
| WO | WO2008028686 A3 | 6/2008 |
| WO | WO-2008070593 A2 | 6/2008 |
| WO | WO-2008086122 A2 | 7/2008 |
| WO | WO-2008092117 A2 | 7/2008 |
| WO | WO2008031056 A3 | 10/2008 |
| WO | WO2008070593 A3 | 10/2008 |
| WO | WO2008086122 A3 | 10/2008 |
| WO | WO2008127735 A1 | 10/2008 |
| WO | WO-2008127735 A1 | 10/2008 |
| WO | WO-2008140603 A2 | 11/2008 |
| WO | WO2008140603 A2 | 11/2008 |
| WO | WO2008092117 A3 | 12/2008 |
| WO | WO2007070538 A2 | 1/2009 |
| WO | WO-2009020933 A2 | 2/2009 |
| WO | WO2009023265 A1 | 2/2009 |
| WO | WO-2009023265 A1 | 2/2009 |
| WO | WO2009026274 A1 | 2/2009 |
| WO | WO-2009026274 A1 | 2/2009 |
| WO | WO-2009033094 A2 | 3/2009 |
| WO | WO2009033094 A3 | 4/2009 |
| WO | WO-2009068204 A1 | 6/2009 |
| WO | WO2009068204 A1 | 6/2009 |
| WO | WO2009070844 A1 | 6/2009 |
| WO | WO-2009070844 A1 | 6/2009 |
| WO | WO2009020933 A9 | 7/2009 |
| WO | WO-2009080829 A1 | 7/2009 |
| WO | WO2009080829 A1 | 7/2009 |
| WO | WO-2009080830 A1 | 7/2009 |
| WO | WO2009080830 A1 | 7/2009 |
| WO | WO2008047242 A8 | 8/2009 |
| WO | WO2008036688 A3 | 9/2009 |
| WO | WO-2009123894 A2 | 10/2009 |
| WO | WO-2009140177 A2 | 11/2009 |
| WO | WO2009123894 A3 | 1/2010 |
| WO | WO-2010022736 A2 | 3/2010 |
| WO | WO2010022736 A3 | 4/2010 |
| WO | WO2009140177 A2 | 8/2010 |
| WO | WO2010112413 A1 | 10/2010 |
| WO | WO-2010112413 A1 | 10/2010 |
| WO | WO2010115554 A1 | 10/2010 |
| WO | WO-2010115554 A1 | 10/2010 |
| WO | WO2011044368 A1 | 4/2011 |
| WO | WO-2011044368 A1 | 4/2011 |
| WO | WO201 2021934 A1 | 2/2012 |
| WO | WO-2012021934 A1 | 2/2012 |
| WO | WO-2012143499 A2 | 10/2012 |
| WO | WO2012143499 A3 | 12/2012 |
| WO | WO2012171020 A1 | 12/2012 |
| WO | WO-2012171020 A1 | 12/2012 |
| WO | WO-2013076186 A1 | 5/2013 |
| WO | WO2013076186 A1 | 5/2013 |
| WO | WO2013087579 A1 | 6/2013 |
| WO | WO-2013087579 A1 | 6/2013 |
| WO | WO-2013173820 A2 | 11/2013 |
| WO | WO2013173820 A2 | 11/2013 |
| WO | WO-2014061277 A1 | 4/2014 |
| WO | WO2014061277 A1 | 4/2014 |
| WO | WO-2014093640 A1 | 6/2014 |
| WO | WO2014093640 A1 | 6/2014 |
| WO | WO-2014131739 A2 | 9/2014 |
| WO | WO-2014151030 A1 | 9/2014 |
| WO | WO2014151030 A1 | 9/2014 |
| WO | WO-2014160160 A2 | 10/2014 |
| WO | WO2014160160 A2 | 10/2014 |
| WO | WO2014131739 A2 | 12/2014 |
| WO | WO-2014198817 A1 | 12/2014 |
| WO | WO2014198817 A1 | 12/2014 |
| WO | WO2015054659 A1 | 4/2015 |
| WO | WO-2015054659 A1 | 4/2015 |
| WO | WO2015089449 A2 | 6/2015 |
| WO | WO-2015089449 A2 | 6/2015 |
| WO | WO2015096982 A1 | 7/2015 |
| WO | WO-2015096982 A1 | 7/2015 |
| WO | WO-2015138615 A2 | 9/2015 |
| WO | WO2015138615 A3 | 12/2015 |
| WO | WO-2015189143 A1 | 12/2015 |
| WO | WO2015189143 A1 | 12/2015 |
| WO | WO2016020791 A1 | 2/2016 |
| WO | WO-2016020791 A1 | 2/2016 |
| WO | WO2016028573 A1 | 2/2016 |
| WO | WO-2016028573 A1 | 2/2016 |
| WO | WO-2016096610 A1 | 6/2016 |
| WO | WO2016096610 A1 | 6/2016 |
| WO | WO-2016201065 A1 | 12/2016 |
| WO | WO2016201065 A1 | 12/2016 |
| WO | WO-2016207089 A1 | 12/2016 |
| WO | WO2016207089 A1 | 12/2016 |
| WO | WO-2016207090 A2 | 12/2016 |
| WO | WO-2016207094 A1 | 12/2016 |
| WO | WO2016207094 A1 | 12/2016 |
| WO | WO-2016207098 A1 | 12/2016 |
| WO | WO2016207098 A1 | 12/2016 |
| WO | WO-2016207103 A1 | 12/2016 |
| WO | WO2016207103 A1 | 12/2016 |
| WO | WO-2016207104 A1 | 12/2016 |
| WO | WO2016207104 A1 | 12/2016 |
| WO | WO2016207090 A3 | 2/2017 |
| WO | WO-2017162663 A1 | 9/2017 |
| WO | WO2017162663 A1 | 9/2017 |
| WO | WO2017216028 A1 | 12/2017 |
| WO | WO-2017216028 A1 | 12/2017 |
| WO | WO2018114578 A1 | 6/2018 |
| WO | WO-2018114578 A1 | 6/2018 |
| WO | WO2018114798 A1 | 6/2018 |
| WO | WO-2018114798 A1 | 6/2018 |
| WO | WO-2018114804 A1 | 6/2018 |
| WO | WO2018114804 A1 | 6/2018 |
| WO | WO-2019243159 A1 | 12/2019 |
| WO | WO-2020094471 A1 | 5/2020 |

OTHER PUBLICATIONS

Brand et al., Anticancer Res. 2006; 26:463-70 (Year: 2006).*
Cancer Treatment Reviews vol. 2 p. 1-31 (1975). (Year: 1975).*
International Preliminary Report on Patentability dated Jul. 4, 2019, for PCT Application No. PCT/EP2017/082789, filed on Dec. 14, 2017, 11 pages.
International Preliminary Report on Patentability dated Jul. 4, 2019, for PCT Application No. PCT/EP2017/083313, filed on Dec. 14, 2017, 10 pages.
International Preliminary Report on Patentability dated Jul. 4, 2019, for PCT Application No. PCT/EP2017/082789, filed on Dec. 14, 2017, 11 pages. German Language.
International Preliminary Report on Patentability dated Jul. 4, 2019, for PCT Application No. PCT/EP2017/083313, filed on Dec. 14, 2017, 10 pages. German Language.
U.S. Appl. No. 15/105,486, filed Jun. 16, 2016, for Hans-Georg Lerchen et al.
U.S. Appl. No. 15/536,112, filed Jun. 14, 2017, for Hans-Georg Lerchen et al.
U.S. Appl. No. 15/739,134, filed Dec. 21, 2017, for Hans-Georg Lerchen et al.
U.S. Appl. No. 16/310,285, filed Dec. 14, 2018, for Hans-Georg Lerchen et al.
U.S. Appl. No. 16/472,749, filed Jun. 21, 2019, for Hans-Georg Lerchen et al.
Ausubel, F.M., ed. (1988). "Current Protocols in Molecular Biology," John Wiley & Sons, Inc.
Bajjuri, K. et al. (2011). "The Legumain Protease-Activated Auristatin Prodrugs Suppress Tumor Growth and Metastasis without Toxicity," Chem Med Chem 6(1):54-59.
Bebbington C.R. et al. (1992). "High-Level Expression of a Recombinant Antibody from Myeloma Cells using a Glutamine Synthetase Gene as an Arnpiifiable Selectable Marker," Bio Technology 10(2):169-175.
Berger, S.L. (1987), "Isolation of Cytoplamic RNA: Ribonucleoside-Vanadyl Complexes," Methods in Enzymology 152:227-234.

(56) References Cited

OTHER PUBLICATIONS

Borrebaeck C. A. K., ed. (1995), "Antibody Engineering (Breakthroughs in Molecular Biology)," Oxford University Press (Copy Not Attached).
Brown S. et al. (2006). "TWEAK binding to the Fn14 cysteine-rich domain depends on charged residues located in both the A1 and D2 modules," Biochem J. 397(2):297-304.
Chen J.M. et al. (1997). "Cloning, Isolation, and Characterization of Mammalian Legumain, an Asparaginyl Endopeptidase," J. Biol. Chem. 272(12):8090-8098.
Chothia, C. et al. (1987). "Canonical Structures for the Hypervariable Regions of Immunoglobulins," J. Mol. Biol. 196:901-917.
Clackson, T. et al. (Aug. 15, 1991). "Making antibody fragments using phage display libraries," Nature 352:624-628.
Culp P.A et al. (2010), "Antibodies to TWEAK Receptor Inhibit Human Tumor Growth through Dual Mechanisms," Clin Cancer Res, 16(2):497-508.
Delfourne E. et al. (2003), "Synthesis and in Vitro Antitumor Activity of Phenanthrolin-7-one Derivatives, Analogus of the Marine Pyridoacridine Alkaloids Ascididemin and Meridine: Structure-Activity Relationship," J. Med. Chem. 46(16):3536-3545.
Donohue P.J. et al. (2003). "TWEAK is an Endothelial Cell Growth and Chemotactic Factor that also Potentiates FGF-2 and VEGF-A Mitogenic Activity," Arterioscler Thromb Vase Biol, 23(4):594-600.
Doronina, S.O et al. (Jul. 2003). "Development of Potent Monoclonal Antibody Auristatin Conjugates for Cancer Therapy," Nat. Biotechnol. 21(7)778-784.
Dubowchik G.M. et al. (1998), "Cathepsin B-Sensitive Dipeptide Prodrugs. 1. A Model Study of Structural Requirements for Efficient Release of Doxorubicin," Bioorg Med Chem Lett 8(23):3341-3346.
Dubowchik G.M. et al. (2002), "Cathepsin B-Labile Dipeptide Linkers for Lysosomal Release of Doxorubicin from Internalizing Immunoconjugates: Model Studies of Enzymatic Drug Release and Antigen-Specific in Vitro Anticancer Activity," Chem. 13(4):855-869.
Ducry, L. et al. (2010), "Antibody-Drug Conjugates: Linking Cytotoxic Payloads to Monoclonal Antibodies," Bioconjugate Chem. 21(1): 5-13.
Durocher Y. et al. (2002). "High-level and high-throughput recombinant protein production by transient, transfection of suspension-growing human 293-EBNA1 cells," Nucleic Acids Research, 30(2):1-9.
Fan L. et al. (2012). "Improving the Efficiency of CHO Cell Line Generation Using Glutamine Synthetase Gene Knockout Cells," Biotechnol Bioeng. 109(4):1007-1015.
Gerbauer, M. et al. (2009). "Engineered protein scaffolds as next-generation antibody therapeutics," Curr. Opinion in Chem. Biol. 13:245-255.
Harlow et al. eds. (1988). "Using Antibodies: A Laboratory Manual," Cold Spring Harbor Laboratory Press, pp, iv-ix, (Table of Contents Only).
Harlow, E. et al. (1998). "Using Antibodies: A Laboratory Manual," Cold Spring Harbor Laboratory Press. (Copy Not Attached).
Hoet, R.M. et al. (2005), "Generation of high-affinity human antibodies by combining donor-derived and synthetic complementarity-determining-region diversity," Nat Biotechnol, 23(3):344-348.
Hoogenboom H.R. et al. (2005), "Selecting and screening recombinant antibody libraries," Nat Biotechnol. 23(9):1105-1116.
International Preliminary Report on Patentability dated Dec. 27, 2018, for PCT Application No. PCT/EP2017/063951, filed on Jun. 8, 2017, 11 pages.
International Preliminary Report on Patentability dated Jul. 7, 2016, for PCT Application No. PCT/EP2014/077144 filed on Dec. 10, 2014, 12 pages.
International Search Report and Written Opinion dated Apr. 19, 2018, for PCT Application No. PCT/EP2017/082789, filed on Dec. 14, 2017, 17 pages.
International Search Report and Written Opinion dated Apr. 23, 2018, for PCT Application No. PCT/EP2017/083313, filed on Dec. 18, 2017, 17 pages.
International Search Report and Written Opinion dated Apr. 29, 2015, for PCT Application No. PCT/EP2014/077144 filed on Dec. 10, 2014, 12 pages.
International Search Report and Written Opinion dated Mar. 24, 2016, for PCT Application No. PCT/EP2015/079273 filed on Dec. 10, 2015, 14 pages.
International Search Report and Written Opinion dated Sep. 12, 2017, for PCT Application No. PCT/EP2017/063951, filed on Jun. 8, 2017, 16 pages.
International Search Report and Written Opinion dated Sep. 19, 2016, for PCT Application No. PCT/EP2016/064133, filed on Jun. 20, 2016, 14 pages.
Ishii S.I. (1994). "Legumain: Asparaginyi Endopeptidase," Meth Enzymol. 244:604-615.
Junutula J.R et al. (2008), "Site-specific conjugation of cytotoxic drug to an antibody improves the therapeutic index," Nat Biotechnol. 26(8):925-932.
Kabat, E.V. et al. (1991). Sequences of Proteins Immunological Interest, 5th Ed. Public Health Service, National Institutes of Health Bethesda, MD, pp. iii-xix.
Kaufman R.J. et al. (1982). "Amplification and Expression of Sequences Cotransfected with a Modular Dihydrofolate Reductase Complementary DNA Gene," J. Mol. Biol. 159:601-621.
Keefe A.D. et al. (2010). "Aptamers as Therapeutics," Nat. Rev. Drug Discov. 9:537-550.
Kohler, G. et al. (Aug. 7, 1975) "Continuous Cultures of Fused Cells Secreting Antibody of Predefined Specificity," Nature 256:495-497.
Kontermann R. et al. eds. (2001) "Antibody Engineering," Springer Laboratory Manual, Springer Verlag, pp. vii-xii (Table of Contents Only).
Kostelny, S.A. et al. (Mar. 1, 1992), "Formation of a Bispecific Antibody by the Use of Leucine Zippers," J. Immunol. 148(5):1547-1553.
Kuo, S-R. et al. (2009). "Antibody Internalization after Cell Surface Antigen Binding is Critical for Immunotoxin Development," Bioconjugate Chem. 20(10): 1975-1982.
Lambert, J. (2005), "Drug-conjugated monoclonal antibodies for the treatment of cancer," Current Opinion in Pharmacology 5:543-549.
Lang K. et al. (2014), "Cellular incorporation of Unnatural Amino Acids and Bioorthogonal Labeling of Proteins," Chem. Rev. 114(9):4764-4806.
Lerchen H.-G. et al. (2017). "Abstract 3234: Development of potent and selective antibody-drug conjugates with pyrrole-based KSP inhibitors as novel payload class," Cancer Research, AACR, 77(13):1-3.
Li B. et al. (2016). "Design, synthesis and evaluation of anti-CD123 antibody drug conjugates," Bioorg Med Chem 24(22):5855-5860.
Lonberg et ai. "Human Antibodies From Transgenic Mice," Intern. Rev. Immunol. 13:65-93, (1995).
Mayer, T.U et al. (1999), "Small Molecule Inhibitor of Mitotic Spindle Bipolarity Identified in a Phenotype-Based Screen," Science 286:971-974.
Michaelson J.S. et al. (2011), "Development of an Fn14 agonistic antibody as an anti-tumor agent," mAbs. 3(4):362-375.
Nakayama M. et al. (2003). "Characterization of murine TWEAK and its receptor (Fn14) by monoclonal antibodies," Biochem Biophys Res Com 306:819-825.
Nuttall S.D. et al. (2008). "Display scaffolds: protein engineering for novel therapeutics," Curr. Opinion in Pharmacol. 8:609-615.
Olsson L. et al. (1983). "[1] Human-Human Monoclonal Antibody-Producing Hybridomas: Technical Aspects," Meth Enzymol. 92:3-16.
Paul W.E. (1998). "Fundamental Immunology," Lippincott-Raven Publishers: Philadelphia, 9 pages (Table of Contents Only).
Pellegrini M. et al. (2013), "Structures of the extracellular domains of human and Xenopus Fn14: implications in the evolution of TWEAK and Fn14 interactions," FEBS 280:1818-1829.
Peterson J.J. et al. (1998), "Cathepsin Substrates as Cleavable Peptide Linkers in Bioconjugates, Selected from a Fluorescence Quench Combinatorial Library," Bioconjug Chem 9(5):618-626.

(56) References Cited

OTHER PUBLICATIONS

Polson A.G. et al. (2007), "Antibody-drug conjugates targeted to CD79 for the treatment of non-Hodgkin lymphoma," Blood 110(2):616-623.
Polson A.G. et al. (2009), "Antibody-Drug Conjugates for the Treatment of Non-Hodgkin's Lymphoma: Target and Linker-Drug Selection," Cancer Res. 69(6):2358-2364.
Queen, C. et al. (Dec. 1989), "A Humanized Antibody That Binds to the Interleukin 2 Receptor," Proc. Natl Acad. Sci. USA 86:10029-10033.
Rashidian M. et al. (2013), "Enzymatic Labeling of Proteins: Techniques and Approaches," Bioconjugate Chem. 24(8):1277-1294.
Sambrook, J. et al. (1989). Molecular Cloning: A Laboratory Manual, 2nd ed., Cold Spring Harbor Laboratory, Cold Spring Harbor, NY, Table of Contents, v-xxxii, 29 pages.
Schinkel A.H. et al. (1995), "Absence of the mdr1a P-Glycoprotein in Mice Affects Tissue Distribution and Pharmacokinetics of Dexamethasone, Digoxin, and Cyclosporin A," J. Clin. Invest. 96:1698-1705.
Schwab D. et al. (2003), "Comparison of in Vitro P-Glycoprotein Screening Assays: Recommendations for Their Use in Drug Discovery," J. Med. Chem. 46:1716-1725.
Seki M. et al. (2000), "Practical Synthesis of (R)-4-Mercaptopyrrolidine-2-thione from L-Aspartic Acid. Preparation of a Novel Orally Active 1-β-Methycarbapenem, TA-949," J.Org.Chem. 65(2):517-522.
Senter, P.D. (2009), "Potent antibody drug conjugates for cancer therapy," Current Opinion in Chemical Biology 13:235-244.
Soderlind, E. et al. (2000). "Recombining germline-derived CDR sequences for creating diverse single-framework antibody libraries," Nature Biotechnology 18:852-856.
Sommer A. et al. (2017), "Abstract 46: Preclinical activity of novel antibody-drug conjugates with pyrrole-based kinesin spindle protein inhibitors targeting different tumor antigens," Cancer Research, AACR 77(13):1-3.
Stern L. et al. (2009). "A Novel Antitumor Prodrug Platform Designed to be Cleaved by the Endoprotease Legumain," Bioconjugate Chem. 20(3):500-510.
Sun, Q. et al. (1996). "Monoclonal Antibody 7G3 Recognizes the N-Terminal Domain of the Human Interleukin-3 (IL-3) Receptor α-Chain and Functions as a Specific IL-3 Receptor Antagonist," Blood 87(1): 83-92.
Tao, W. et al. (2005), "Induction of apoptosis by an inhibitor of the mitotic kinesin KSP requires both activation of the spindle assembly checkpoint and mitotic slippage," Cancer Cell 8(1): 49-59.
Tom R. et al. (2007), "Transient expression in HEK293-EBNA1 cells," in Expression Systems: Methods Express, Dyson, M.R et al. eds., Scion Publishing Ltd.: Oxfordshire, pp. 204-223.
Troutman M.D. et al. (2003), "Novel Experimental Parameters to Quantify the Modulation of Absorptive and Secretory Transport of Compounds by P-Glycoprotein in Cell Culture Models of Intestinal Epithelium," Pharm. Res. 20(8):1210-1224.
Tutt, A. et al. (Jul. 1, 1991) "Trispecific F(ab')3 Derivatives that use Cooperative Signaling Via the TCR/CD3 Complex and CD2 to Activate and Redirect Resting Cytotoxic T Cells," J. Immunol. 147(1):60-69.
Urlaub G. et al. (1980). "Isolation of Chinese hamster cell mutants deficient in dihydrofolate reductase activity," Proc. Natl. Acad. Sci. USA 77(7):4216-4220.
Urlaub G. et al. (1983). "Deletion of the Diploid Dihydrofolate Reductase Locus from Cultured Mammalian Cells," Cell 33(2):405-412.
Wang Y. et al. (2014). "Protease-Activatable Hybrid Nanoprobe for Tumor Imaging," Adv. Funct. Mater. 24(34):5443-5453.
Wiley S.R. et al. (2001). "A Novel TNF Receptor Family Member Binds TWEAK and Is Implicated in Angiogenesis," Immunity 15:837-846.
Wu W. et al. (2006). "Targeting Cell-Impermeable Prodrug Activation to Tumor Microenvironment Eradicates Multiple Drug-Resistant Neoplasms," Cancer Res. 66(2):970-980.
Wu, A. et al. (2005). "Arming antibodies: prospects and challenges for immunoconjugates," Nature Biotechnology 23(9): 1137-1146.
Zhou H. et al. (2011). "Development and Characterization of a Potent Immunoconjugate Targeting the Fn14 Receptor on Solid Tumor Cells," Mol Cancer Therapeutics 10(7):276-1288.
Zhou H. et al. (2012). "The TWEAK Receptor Fn14 is a Novel Therapeutic Target in Melanoma: Immunotoxins Targeting Fn14 Receptor for Malignant Melanoma Treatment," J. Invest Dermatol. 133(4):1052-1062.
Bajjuri et al. The legumain protease-activated auristatin prodrugs suppress tumor growth and metastasis without toxicity. ChemMedChem 6(1):54-59 (2011).
Bebbington et al. High-level expression of a recombinant antibody from myeloma cells using a glutamine synthetase gene as an amplifiable selectable marker. Biotechnology 10(2):169-75 (1992).
Berger. Isolation of Cytoplamic RNA: Ribonucleoside-Vanadyl Complexes. Methods in Enzymology 152:227-234 (1987).
Borrebaeck. Antibody Engineering. 2nd edition, Ed., Oxford University Press, New York, 1995.
Brand et al. Prospect for Anti-HER2 Receptor Therapy in Breast Cancer. Anticancer Research 26(1B):463-470 (2006).
Brown et al. TWEAK binding to the Fn14 cysteine-rich domain depends on charged residues located in both the AI and D2 modules. Biochem J. 397(2):297-304 (2006).
Chen et al. Cloning, isolation, and characterization of mammalian legumain, an asparaginyl endopeptidase. J. Biol. Chem. 272:8090-8098 (1997).
Chothia et al. Canonical structures for the hypervariable regions of immunoglobulins. J Mol Biol 196:901-917 (1987).
Clackson et al. Making antibody fragments using phage display libraries. Nature 352(6336):624-628 (1991).
Co-pending U.S. Appl. No. 17/166,713, inventors Lerchen; Hans-Georg et al., filed Mar. 3, 2021.
Co-pending U.S. Appl. No. 17/253,086, inventors Johannes; Sarah Anna Liesa et al., filed Dec. 16, 2020.
Culp et al. Antibodies to TWEAK receptor inhibit human tumor growth through dual mechanisms. Clin Cancer Res. 16(2):497-508 (2010).
Delfourne et al. Synthesis and in vitro antitumor activity of phenanthrolin-7-one derivatives, analogues of the marine pyridoacridine alkaloids ascididemin and meridine: structure-activity relationship. J. Med. Chem. 46(16):3536-3545 (2003).
Donohue et al. TWEAK is an Endothelial Cell Growth and Chemotactic Factor that also Potentiates F-2 and VEGF-A Mitogenic Activity. Arterioscler Thromb Vase Biol, 23(4):594-600 (2003).
Doronina et al. Development of potent monoclonal antibody auristatin conjugates for cancer therapy. Nat Biotechnol 21:778-784 (2003).
Dubowchik et al. Cathepsin B-labile dipeptide linkers for lysosomal release of doxorubicin from internalizing immunoconjugates: model studies of enzymatic drug release and antigen-specific in vitro anticancer activity. Bioconjugate Chem. 13:855-869 (2002).
Dubowchik et al. Cathepsin B-sensitive dipeptide prodrugs. 1. A model study of structural requirements for efficient release of doxorubicin. Bioorg Med Chem Lett 8:3341-3346 (1998).
Ducry et al. Antibody-drug conjugates: linking cytotoxic payloads to monoclonal antibodies. Bioconjug Chem. 21(1):5-13 (2010).
Durocher et al., High-level and high-throughput recombinant protein production by transient transfection of suspension-growing human HEK293-EBNA1 cells. Nucleic acids research, 30(2):e9 (2002).
Fan et al. Improving the efficiency of CHO cell line generation using glutamine synthetase gene knockout cells. Biotechnol Bioeng. 109(4):1007-15 (2012).
Gebauer et al. Engineered protein scaffolds as next-generation antibody therapeutics. Curr. Opinion in Chem. Biol. 13:245-255 (2009).
Harlow, et al. Using Antibodies: A Laboratory Manual. Cold Spring Harbor Laboratory, Cold Spring Harbor, N.Y. 1999.

(56) References Cited

OTHER PUBLICATIONS

Hoet et al. Generation of high-affinity human antibodies by combining donor-derived and synthetic complementarity-determining-region diversity. Nature Biotechnology 23(3):344-348 (Mar. 2005).
Hoogenboom. Selecting and screening recombinant antibody libraries. Nat Biotechnol. 23(9):1105-16 (2005).
Ishii. Legumain: asparaginyl endopeptidase. Methods Enzymol. 244:604-615 (1994).
Johnson et al., The Clinical Impact of Screening and other Experimental Tumor Studies. Cancer Treatment Reviews 2: 1-31 (1975).
Junutula et al. Site-specific conjugation of a cytotoxic drug to an antibody improves the therapeutic index. Nat Biotechnol. 26(8):925-32 (2008).
Kabat et al. Sequences of proteins of immunological interest. NIH Publ. No. 91-3242 1:647-669 (1991).
Kaufman, et al. Amplification and expression of sequences cotransfected with a modular dihydrofolate reductase complementary dna gene. J Mol Biol. Aug. 25, 1982; 159(4):601-21.
Keefe et al. Aptamers as therapeutics. Nat. Rev. Drug Discov. 9:537-550 (2010).
Kohler et al. Continuous cultures of fused cells secreting antibody of predefined specificity. Nature256(5517):495-497 (1975).
Kontermann, et al. Antibody Engineering. Springer Lab Manual, Springer Verlag, 2001.
Kostelnyet al. Formation of a bispecific antibody by the use of leucine zippers. J. Immunol. 148(5):1547-1553 (1992).
Kuo et al. Antibody internalization after cell surface antigen binding is critical for immunotoxin development. Bioconjug Chem. 20(10):1975-82 (2009).
Lambert. Drug-conjugated monoclonal antibodies for the treatment of cancer. Curr. Opin. Pharmacol. 5:543-549 (2005).
Lang et al. Cellular Incorporation of Unnatural Amino Acids and Bioorthogonal Labeling of Proteins, Chem.Rev. 114:4764-4806 (2014).
Lerchen et al. Abstract 3234: Development of potent and selective antibody-drug conjugates with 3-yrrole-based KSP inhibitors as novel payload class. Cancer Research, AACR 77(13):1-3 (2017).
Li et al. Design, synthesis and evaluation of anti-CD123 antibody drug conjugates Bioorg Med Chem 24(22):5855-5860 (2016).
Lonberg et al. Human antibodies from transgenic mice. Int Rev Immunol. 13(1):65-93 (1995).
Mayer et al. Small molecule inhibitor of mitotic spindle bipolarity identified in a phenotype-based screen. Science 286(5441):971-974 (1999).
Michaelson et al. Development of an Fn14 agonistic antibody as an anti-tumor agent. MAbs 3(4):362-375 (2011).
Nakayama et al. Characterization of murine TWEAK and its receptor (Fn14) by monoclonal antibodies. Biochem Biophy Res Comm 306:819-825 (2003).
Nuttall et al. Display scaffolds: protein engineering for novel therapeutics. Curr. Opinion in Pharmacology 8:609-615 (2008).
Olsson et al. Human-human monoclonal antibody-producing hybridomas: Technical aspects. Meth Enzymol. 92:3-16 (1983).
Paul, W. E., ed., Fundamental Immunology, 4th Ed., Lippincott-Raven, Philadelphia (1999).
PCT/EP2014/077144 International Search Report and Written Opinion dated Apr. 29, 2015.
PCT/EP2015/079273 International Search Report and Written Opinion dated Mar. 24, 2016.
PCT/EP2016/064133 International Search Report and Written Opinion dated Sep. 19, 2016.
PCT/EP2017/063951 International Search Report and Written Opinion dated Sep. 12, 2017.
PCT/EP2017/082789 International Search Report and Written Opinion dated Apr. 19, 2018.
PCT/EP2017/083313 International Search Report and Written Opinion dated Apr. 23, 2018.
Pellegrini et al. Structure of the extracellular domains of human and Xenopus Fn14: implications in the evolution of TWEAK and Fn14 interactions. FEBS 280:1818-1829 (2013).
Peterson et al. Cathepsin substrates as cleavable peptide linkers in bioconjugates, selected from a fluorescence quench combinatorial library. Bioconjugate Chem. 9:618-626 (1998).
Polson et al. Antibody-drug conjugates for the treatment of non-Hodgkin's lymphoma: target and linker-drug selection. Cancer Res. 69(6):2358-64 (2009).
Polson et al. Antibody-drug conjugates targeted to CD79 for the treatment of non-Hodgkin lymphoma. Blood 110(2):616-623 (2007).
Queen et al. A humanized antibody that binds to the interleukin 2 receptor. PNAS USA 86:10029-10032 (1989).
Rashidian et al. Enzymatic labeling of proteins: techniques and approaches. Bioconjugate Chem. 24:1277-1294 (2013).
Schinkel et al. Absence of the mdr1a P-Glycoprotein in mice affects tissue distribution and pharmacokinetics of dexamethasone, digoxin, and cyclosporin A. J. Clin. Invest. 96:1698-1705 (1995).
Schwab et al. Comparison of in vitro P-glycoprotein screening assays: recommendations for their use in drug discovery. J. Med. Chem. 46:1716-1725 (2003).
Söderlind et al. Recombining germline-derived CDR sequences for creating diverse single-framework antibody libraries. Nature Biotechnology 18:852-856 (Aug. 1, 2000).
Seki et al. Practical synthesis of (R)-4-mercaptopyrrolidine-2-thione from L-aspartic acid. Preparation of a novel orally active 1-beta-methylcarbapenem, TA-949. J. Org. Chem. 65:517-522 (2000).
Senter. Potent antibody drug conjugates for cancer therapy. Curr. Opin. Chem. Biol 13:235-244 (2009).
Sommer et al. Abstract 46: Preclinical activity of novel antibody-drug conjugates with pyrrole-based kinesin spindle protein inhibitors targeting different tumor antigens. Cancer Research, AACR 77(13):1-3 (2017).
Stern, L. et al., A novel antitumor prodrug platform designed to be cleaved by the endoprotease legumain, Bioconj. Chem., 20: 500-510 (2009).
Strome et al. A mechanistic perspective of monoclonal antibodies in cancer therapy beyond target-related effects. The Oncologist 12:1084-95 (2007).
Sun et al. Monoclonal antibody 7G3 recognizes the N-terminal domain of the human interleukin-3 (IL-3) receptor alpha-chain and functions as a specific IL-3 receptor antagonist. Blood 87(1):83-92 (1996).
Tao et al. Induction of apoptosis by an inhibitor of the mitotic kinesin KSP requires both activation of the spindle assembly checkpoint and mitotic slippage. Cancer Cell 8(1):49-59 (2005).
Tom et al. Transient expression in HEK293-EBNA1 cells, in Expression Systems: Methods Express, Dyson, M.R et al. eds., Scion Publishing Ltd.: Oxfordshire, pp. 204-223 (2007).
Troutman et al. Novel experimental parameters to quantify the modulation of absorptive and secretory transport of compounds by P-glycoprotein in cell culture models of intestinal epithelium. Pharm. Res. 20(8):1210-1224 (2003).
Tutt et al. Trispecific F(ab')3 derivatives that use cooperative signaling via the TCR/CD3 complex and CD2 to activate and redirect resting cytotoxic T cells. J Immunol. 147(1):60-69 (Jul. 1, 1991).
Urlaub et al. Deletion of the diploid dihydrofolate reductase locus from cultured mammalian cells. Cell 33(2):405-12 (1983).
Urlaub et al. Isolation of Chinese hamster cell mutants deficient in dihydrofolate reductase activity. PNAS USA 77:4216-4220 (1980).
Wang et al. Protease-Activatable Hybrid Nanoprobe for Tumor Imaging. Adv. Funct. Mater. 24(34):5443-5453 (2014).
Wiley et al. A Novel TNF Receptor Family Member Binds TWEAK and Is Implicated in Angiogenesis. Immunity 15:837-846 (2001).
Wu et al. Arming antibodies: prospects and challenges for immunoconjugates. Nat. Biotechnol. 23:1137-1146 (2005).
Wu et al. Targeting cell-impermeable prodrug activation to tumor microenvironment eradicates multiple drug-resistant neoplasms. Cancer Res. 66:970-980 (2006).
Zhou et al. Development and Characterization of a Potent Immunoconjugate Targeting the Fn14 Receptor on Solid Tumor Cell. Mol Cancer Therapeutics 10(7):1276-1288 (2011).

(56) References Cited

OTHER PUBLICATIONS

Zhou et al. The TWEAK Receptor Fn14 is a Novel Therapeutic Target in Melanoma: Immunotoxins Targeting Fn14 Receptor for Malignant Melanoma Treatment. J. Invest Dermatol. 133(4):1052-1062 (2013).
Co-pending U.S. Appl. No. 17/290,911, inventors Lerchen; Hans-Georg et al., filed May 3, 2021.
Co-pending U.S. Appl. No. 17/374,756, inventors Lerchen; Hans-Georg et al., filed Jul. 13, 2021.

* cited by examiner

FIG. 1A

```
>TPP-8987 VH (PRT)
QVQLVQSGAEVKKPGSSVKVSCKASGGTFSDYYMKWVRQAPGQGLEWMGDIIPSNGATFYNQKFKGQVTITADESTSTAY
                              |---|                   |-----HCDR2-----|
                              HCDR1

MELSSLRSEDTAVYYCARSHLLRASWFAYWGQGTLVTVSS
              |--HCDR3--|

>TPP-8987 VL (PRT)
DIVMTQSPDSLAVSLGERATINCESSQSVLNSGNQKNYLTWYQQKPGQPPKLLIYWASTRESGVPDRFSGSGSGTDFTLT
                    |-----LCDR1-----|                |-----|
                                                       LCDR2

ISSLQAEDVAVYYCQNDYSYPYTFGQGTKLEIK
             |-LCDR3-|

>TPP-8987 Heavy Chain (PRT)
QVQLVQSGAEVKKPGSSVKVSCKASGGTFSDYYMKWVRQAPGQGLEWMGDIIPSNGATFYNQKFKGQVTITADESTSTAY
|-----------------------------------------------------VH-------------------
                              |---|                   |-----HCDR2-----|
                              HCDR1

MELSSLRSEDTAVYYCARSHLLRASWFAYWGQGTLVTVSSASTKGPSVFPLAPSSKSTSGGTAALGCLVKDYFPEPVTVS
------------------------------------|
              |--HCDR3--|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

>TPP-8987 Light Chain (PRT)
DIVMTQSPDSLAVSLGERATINCESSQSVLNSGNQKNYLTWYQQKPGQPPKLLIYWASTRESGVPDRFSGSGSGTDFTLT
|----------------------------------------------------VL-----------------------
                    |-----LCDR1-----|                |-----|
                                                       LCDR2

ISSLQAEDVAVYYCQNDYSYPYTFGQGTKLEIKRTVAAPSVFIFPPSDEQLKSGTASVVCLLNNFYPREAKVQWKVDNAL
-------------------------------|
             |-LCDR3-|
```

FIG. 1B

```
QSGNSQESVTEQDSKDSTYSLSSTLTLSKADYEKHKVYACEVTHQGLSSPVTKSFNRGEC

>TPP-8988 VH (PRT)
EVQLLESGGGLVQPGGSLRLSCAVSDYSITSGYYWNWIRQAPGKKLEWMGYISYDGSNNYNPSLKNGRITISRDTSKNTF
                            |----|                  |-----HCDR2-----|
                            HCDR1

YLQMNSLRAEDTAVYYCARGEGFYFDSWGQGTLVTVSS
                 |------|
                 HCDR3

>TPP-8988 VL (PRT)
EIVLTQSPGTLSLSPGERATLSCKSSQSLFFGSTQKNYLAWYQQKPGQAPRLLIYWASTRESGIPDRFSGSGSGTDFTLT
                      |-----LCDR1-----|                 |-----|
                                                         LCDR2

ISRLEPEDFAVYYCQQYYNYPWTFGQGTKLEIK
             |-LCDR3-|

>TPP-8988 Heavy Chain (PRT)
EVQLLESGGGLVQPGGSLRLSCAVSDYSITSGYYWNWIRQAPGKKLEWMGYISYDGSNNYNPSLKNGRITISRDTSKNTF
|-----------------------------------------------------------VH--------------------
                            |----|                  |-----HCDR2-----|
                            HCDR1

YLQMNSLRAEDTAVYYCARGEGFYFDSWGQGTLVTVSSASTKGPSVFPLAPSSKSTSGGTAALGCLVKDYFPEPVTVSWN
-----------------------------------|
                 |------|
                 HCDR3

SGALTSGVHTFPAVLQSSGLYSLSSVVTVPSSSLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNAKTKPREEQYNSTYRVVSVLTVLHQDWLNGKEY

KCKVSNKALPAPIEKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

>TPP-8988 Light Chain (PRT)
EIVLTQSPGTLSLSPGERATLSCKSSQSLFFGSTQKNYLAWYQQKPGQAPRLLIYWASTRESGIPDRFSGSGSGTDFTLT
|---------------------------------------------------------VL-----------------------
                      |-----LCDR1-----|                 |-----|
                                                         LCDR2

ISRLEPEDFAVYYCQQYYNYPWTFGQGTKLEIKRTVAAPSVFIFPPSDEQLKSGTASVVCLLNNFYPREAKVQWKVDNAL
-------------------------------|
             |-LCDR3-|
```

FIG. 1C

```
QSGNSQESVTEQDSKDSTYSLSSTLTLSKADYEKHKVYACEVTHQGLSSPVTKSFNRGEC

>TPP-9024 VH (PRT)
EVQLVESGGGLVQPGKSLKLSCSASGFTFSTSGMHWFRQAPGKGLDWVAYISSSSGFVYADAVKGRFTISRDNAQNTLYL
                             |---|              |----HCDR2-----|
                             HCDR1

QLNSLKSEDTAIYYCARSEAAFWGQGTLVTVSS
             |---|
             HCDR3

>TPP-9024 VL (PRT)
DIVLTQAPRSVSVTPGESASISCRSNKSRLSRMGITPLNWYLQKPGKSPQLLIYRMSNLASGVPDRFSGSGSETDFTLKI
                  |----LCDR1-----|                    |-----|
                                                         LCDR2

SKVETEDVGVYYCAQFLEYPPTFGSGTKLEIK
           |-LCDR3-|

>TPP-9024 Heavy Chain (PRT)
EVQLVESGGGLVQPGKSLKLSCSASGFTFSTSGMHWFRQAPGKGLDWVAYISSSSGFVYADAVKGRFTISRDNAQNTLYL
|---------------------------------------------------VH----------------------
                             |---|              |----HCDR2-----|
                             HCDR1

QLNSLKSEDTAIYYCARSEAAFWGQGTLVTVSSASTKGPSVFPLAPSSKSTSGGTAALGCLVKDYFPEPVTVSWNSGALT
-----------------------------|
             |---|
             HCDR3

SGVHTFPAVLQSSGLYSLSSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSVLTVLHQDWLNGKEYKCKVS

NKALPAPIEKTISKAKGQPREPQVYTLPPSRDELTKNQVSLTCLVKGFYPSDIAVEWESNGQPENNYKTTPPVLDSDGSF

FLYSKLTVDKSRWQQGNVFSCSVMHEALHNHYTQKSLSLSPG

>TPP-9024 Light Chain (PRT)
DIVLTQAPRSVSVTPGESASISCRSNKSRLSRMGITPLNWYLQKPGKSPQLLIYRMSNLASGVPDRFSGSGSETDFTLKI
|---------------------------------------------------VL----------------------
                  |----LCDR1-----|                    |-----|
                                                         LCDR2

SKVETEDVGVYYCAQFLEYPPTFGSGTKLEIKRTVAAPSVFIFPPSDEQLKSGTASVVCLLNNFYPREAKVQWKVDNALQ
-----------------------------|
           |-LCDR3-|
```

FIG. 1D

```
SGNSQESVTEQDSKDSTYSLSSTLTLSKADYEKHKVYACEVTHQGLSSPVTKSFNRGEC

>TPP-9476 VH (PRT)
QVQLVQSGAEVKKPGSSVKVSCKASGGTFSDYYMKWVRQAPGQGLEWMGDIIPSNGATFYNQKFKGRVTITADESTSTAY
                        |---|                   |-----HCDR2-----|
                        HCDR1

MELSSLRSEDTAVYYCARSHLLRASWFAYWGQGTLVTVSS
                |--HCDR3--|

>TPP-9476 VL (PRT)
DIVMTQSPDSLAVSLGERATINCESSQSVLNSGNQKNYLTWYQQKPGQPPKLLIYWASTRESGVPDRFSGSGSGTDFTLT
                    |-----LCDR1-----|                    |-----|
                                                            LCDR2

ISSLQAEDVAVYYCQNDYSYPYTFGQGTKLEIK
            |-LCDR3-|

>TPP-9476 Heavy Chain (PRT)
QVQLVQSGAEVKKPGSSVKVSCKASGGTFSDYYMKWVRQAPGQGLEWMGDIIPSNGATFYNQKFKGRVTITADESTSTAY
|------------------------------------------------------------VH-------------------
                        |---|                   |-----HCDR2-----|
                        HCDR1

MELSSLRSEDTAVYYCARSHLLRASWFAYWGQGTLVTVSSASTKGPSVFPLAPSSKSTSGGTAALGCLVKDYFPEPVTVS
-------------------------------------|
                |--HCDR3--|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

>TPP-9476 Light Chain (PRT)
DIVMTQSPDSLAVSLGERATINCESSQSVLNSGNQKNYLTWYQQKPGQPPKLLIYWASTRESGVPDRFSGSGSGTDFTLT
|--------------------------------------------------------VL----------------------
                    |-----LCDR1-----|                    |-----|
                                                            LCDR2

ISSLQAEDVAVYYCQNDYSYPYTFGQGTKLEIKRTVAAPSVFIFPPSDEQLKSGTASVVCLLNNFYPREAKVQWKVDNAL
-------------------------------|
            |-LCDR3-|
```

FIG. 1E

```
QSGNSQESVTEQDSKDSTYSLSSTLTLSKADYEKHKVYACEVTHQGLSSPVTKSFNRGEC

>TPP-9574 VH (PRT)
EVQLVESGGGLIQPGGSLRLSCAASGFTFSTSGMHWFRQAPGKGLEWVAYISSSSGFVYADAVKGRFTISRDNSKNTLYL
                        |---|                    |----HCDR2-----|
                        HCDR1

QMNSLRAEDTAVYYCARSEAAFWGQGTLVTVSS
              |---|
              HCDR3

>TPP-9574 VL (PRT)
DIVMTQSPLSLPVTPGEPASISCRSQKSRLSRMGITPLNWYLQKPGQSPQLLIYRMSNLASGVPDRFSGSGSGTDFTLKI
                   |----LCDR1-----|                     |-----|
                                                         LCDR2

SRVEAEDVGVYYCAQFLEYPPTFGQGTKLEIK
          |-LCDR3-|

>TPP-9574 Heavy Chain (PRT)
EVQLVESGGGLIQPGGSLRLSCAASGFTFSTSGMHWFRQAPGKGLEWVAYISSSSGFVYADAVKGRFTISRDNSKNTLYL
|----------------------------------------------------VH-----------------------
                        |---|                    |----HCDR2-----|
                        HCDR1

QMNSLRAEDTAVYYCARSEAAFWGQGTLVTVSSASTKGPSVFPLAPSSKSTSGGTAALGCLVKDYFPEPVTVSWNSGALT
-------------------------------|
              |---|
              HCDR3

SGVHTFPAVLQSSGLYSLSSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSVLTVLHQDWLNGKEYKCKVS

NKALPAPIEKTISKAKGQPREPQVYTLPPSRDELTKNQVSLTCLVKGFYPSDIAVEWESNGQPENNYKTTPPVLDSDGSF

FLYSKLTVDKSRWQQGNVFSCSVMHEALHNHYTQKSLSLSPG

>TPP-9574 Light Chain (PRT)
DIVMTQSPLSLPVTPGEPASISCRSQKSRLSRMGITPLNWYLQKPGQSPQLLIYRMSNLASGVPDRFSGSGSGTDFTLKI
|----------------------------------------------------VL-----------------------
                   |----LCDR1-----|                     |-----|
                                                         LCDR2

SRVEAEDVGVYYCAQFLEYPPTFGQGTKLEIKRTVAAPSVFIFPPSDEQLKSGTASVVCLLNNFYPREAKVQWKVDNALQ
-------------------------------|
          |-LCDR3-|
```

FIG. 1F

```
SGNSQESVTEQDSKDSTYSLSSTLTLSKADYEKHKVYACEVTHQGLSSPVTKSFNRGEC

>TPP-9580 VH (PRT)
EVQLVESGGGLIQPGGSLRLSCAASGFTFSTSGMHWVRQAPGKGLEWVSYISSSSGFVYADAVKGRFTISRDNSKNTLYL
                          |---|                    |----HCDR2-----|
                          HCDR1

QMNSLRAEDTAVYYCARSEAAFWGQGTLVTVSS
              |---|
              HCDR3

>TPP-9580 VL (PRT)
DIVMTQSPLSLPVTPGEPASISCRSQKSRLSRMGITPLNWYLQKPGQSPQLLIYRMSNLASGVPDRFSGSGSGTDFTLKI
                   |----LCDR1-----|                      |-----|
                                                            LCDR2

SRVEAEDVGVYYCAQFLEYPPTFGQGTKLEIK
           |-LCDR3-|

>TPP-9580 Heavy Chain (PRT)
EVQLVESGGGLIQPGGSLRLSCAASGFTFSTSGMHWVRQAPGKGLEWVSYISSSSGFVYADAVKGRFTISRDNSKNTLYL
|----------------------------------------------------VH----------------------
                          |---|                    |----HCDR2-----|
                          HCDR1

QMNSLRAEDTAVYYCARSEAAFWGQGTLVTVSSASTKGPSVFPLAPSSKSTSGGTAALGCLVKDYFPEPVTVSWNSGALT
------------------------------|
              |---|
              HCDR3

SGVHTFPAVLQSSGLYSLSSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSVLTVLHQDWLNGKEYKCKVS

NKALPAPIEKTISKAKGQPREPQVYTLPPSRDELTKNQVSLTCLVKGFYPSDIAVEWESNGQPENNYKTTPPVLDSDGSF

FLYSKLTVDKSRWQQGNVFSCSVMHEALHNHYTQKSLSLSPG

>TPP-9580 Light Chain (PRT)
DIVMTQSPLSLPVTPGEPASISCRSQKSRLSRMGITPLNWYLQKPGQSPQLLIYRMSNLASGVPDRFSGSGSGTDFTLKI
|----------------------------------------------------VL----------------------
                   |----LCDR1-----|                      |-----|
                                                            LCDR2

SRVEAEDVGVYYCAQFLEYPPTFGQGTKLEIKRTVAAPSVFIFPPSDEQLKSGTASVVCLLNNFYPREAKVQWKVDNALQ
------------------------------|
           |-LCDR3-|
```

FIG. 1G

SGNSQESVTEQDSKDSTYSLSSTLTLSKADYEKHKVYACEVTHQGLSSPVTKSFNRGEC

FIG. 2A

<SEQ ID NO:1>
QVQLVQSGAEVKKPGSSVKVSCKASGGTFSDYYMKWVRQAPGQGLEWMGDIIPSNGATFYNQKFKGQV
TITADESTSTAYMELSSLRSEDTAVYYCARSHLLRASWFAYWGQGTLVTVSS

<SEQ ID NO:2>
DYYMK

<SEQ ID NO:3>
DIIPSNGATFYNQKFKG

<SEQ ID NO:4>
SHLLRASWFAY

<SEQ ID NO:5>
DIVMTQSPDSLAVSLGERATINCESSQSVLNSGNQKNYLTWYQQKPGQPPKLLIYWASTRESGVPDRF
SGSGSGTDFTLTISSLQAEDVAVYYCQNDYSYPYTFGQGTKLEIK

<SEQ ID NO:6>
ESSQSVLNSGNQKNYLT

<SEQ ID NO:7>
WASTRES

<SEQ ID NO:8>
QNDYSYPYT

<SEQ ID NO:9>
QVQLVQSGAEVKKPGSSVKVSCKASGGTFSDYYMKWVRQAPGQGLEWMGDIIPSNGATFYNQKFKGQV
TITADESTSTAYMELSSLRSEDTAVYYCARSHLLRASWFAYWGQGTLVTVSSASTKGPSVFPLAPSSK
STSGGTAALGCLVKDYFPEPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKCKVSNKALPAPIEKTIS
KAKGQPREPQVYTLPPSRDELTKNQVSLTCLVKGFYPSDIAVEWESNGQPENNYKTTPPVLDSDGSFF
LYSKLTVDKSRWQQGNVFSCSVMHEALHNHYTQKSLSLSPG

<SEQ ID NO:10>
DIVMTQSPDSLAVSLGERATINCESSQSVLNSGNQKNYLTWYQQKPGQPPKLLIYWASTRESGVPDRF
SGSGSGTDFTLTISSLQAEDVAVYYCQNDYSYPYTFGQGTKLEIKRTVAAPSVFIFPPSDEQLKSGTA
SVVCLLNNFYPREAKVQWKVDNALQSGNSQESVTEQDSKDSTYSLSSTLTLSKADYEKHKVYACEVTH
QGLSSPVTKSFNRGEC

<SEQ ID NO:11>
EVQLLESGGGLVQPGGSLRLSCAVSDYSITSGYYWNWIRQAPGKKLEWMGYISYDGSNNYNPSLKNGR
ITISRDTSKNTFYLQMNSLRAEDTAVYYCARGEGFYFDSWGQGTLVTVSS

<SEQ ID NO:12>
SGYYWN

<SEQ ID NO:13>
YISYDGSNNYNPSLKNG

FIG. 2B

<SEQ ID NO:14>
GEGFYFDS

<SEQ ID NO:15>
EIVLTQSPGTLSLSPGERATLSCKSSQSLFFGSTQKNYLAWYQQKPGQAPRLLIYWASTRESGIPDRF
SGSGSGTDFTLTISRLEPEDFAVYYCQQYYNYPWTFGQGTKLEIK

<SEQ ID NO:16>
KSSQSLFFGSTQKNYLA

<SEQ ID NO:17>
WASTRES

<SEQ ID NO:18>
QQYYNYPWT

<SEQ ID NO:19>
EVQLLESGGGLVQPGGSLRLSCAVSDYSITSGYYWNWIRQAPGKKLEWMGYISYDGSNNYNPSLKNGR
ITISRDTSKNTFYLQMNSLRAEDTAVYYCARGEGFYFDSWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVN
HKPSNTKVDKKVEPKSCDKTHTCPPCPAPELLGGPSVFLFPPKPKDTLMISRTPEVTCVVVDVSHEDP
EVKFNWYVDGVEVHNAKTKPREEQYNSTYRVVSVLTVLHQDWLNGKEYKCKVSNKALPAPIEKTISKA
KGQPREPQVYTLPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPG

<SEQ ID NO:20>
EIVLTQSPGTLSLSPGERATLSCKSSQSLFFGSTQKNYLAWYQQKPGQAPRLLIYWASTRESGIPDRF
SGSGSGTDFTLTISRLEPEDFAVYYCQQYYNYPWTFGQGTKLEIKRTVAAPSVFIFPPSDEQLKSGTA
SVVCLLNNFYPREAKVQWKVDNALQSGNSQESVTEQDSKDSTYSLSSTLTLSKADYEKHKVYACEVTH
QGLSSPVTKSFNRGEC

<SEQ ID NO:21>
EVQLVESGGGLVQPGKSLKLSCSASGFTFSTSGMHWFRQAPGKGLDWVAYISSSSGFVYADAVKGRFT
ISRDNAQNTLYLQLNSLKSEDTAIYYCARSEAAFWGQGTLVTVSS

<SEQ ID NO:22>
TSGMH

<SEQ ID NO:23>
YISSSSGFVYADAVKG

<SEQ ID NO:24>
SEAAF

<SEQ ID NO:25>
DIVLTQAPRSVSVTPGESASISCRSNKSRLSRMGITPLNWYLQKPGKSPQLLIYRMSNLASGVPDRFS
GSGSETDFTLKISKVETEDVGVYYCAQFLEYPPTFGSGTKLEIK

<SEQ ID NO:26>
RSNKSRLSRMGITPLN

FIG. 2C

<SEQ ID NO:27>
RMSNLAS

<SEQ ID NO:28>
AQFLEYPPT

<SEQ ID NO:29>
EVQLVESGGGLVQPGKSLKLSCSASGFTFSTSGMHWFRQAPGKGLDWVAYISSSSGFVYADAVKGRFT
ISRDNAQNTLYLQLNSLKSEDTAIYYCARSEAAFWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSN
TKVDKKVEPKSCDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKTTPPVLDSDGSFFLYSKLTV
DKSRWQQGNVFSCSVMHEALHNHYTQKSLSLSPG

<SEQ ID NO:30>
DIVLTQAPRSVSVTPGESASISCRSNKSRLSRMGITPLNWYLQKPGKSPQLLIYRMSNLASGVPDRFS
GSGSETDFTLKISKVETEDVGVYYCAQFLEYPPTFGSGTKLEIKRTVAAPSVFIFPPSDEQLKSGTAS
VVCLLNNFYPREAKVQWKVDNALQSGNSQESVTEQDSKDSTYSLSSTLTLSKADYEKHKVYACEVTHQ
GLSSPVTKSFNRGEC

<SEQ ID NO:31>
QVQLVQSGAEVKKPGSSVKVSCKASGGTFSDYYMKWVRQAPGQGLEWMGDIIPSNGATFYNQKFKGRV
TITADESTSTAYMELSSLRSEDTAVYYCARSHLLRASWFAYWGQGTLVTVSS

<SEQ ID NO:32>
DYYMK

<SEQ ID NO:33>
DIIPSNGATFYNQKFKG

<SEQ ID NO:34>
SHLLRASWFAY

<SEQ ID NO:35>
DIVMTQSPDSLAVSLGERATINCESSQSVLNSGNQKNYLTWYQQKPGQPPKLLIYWASTRESGVPDRF
SGSGSGTDFTLTISSLQAEDVAVYYCQNDYSYPYTFGQGTKLEIK

<SEQ ID NO:36>
ESSQSVLNSGNQKNYLT

<SEQ ID NO:37>
WASTRES

<SEQ ID NO:38>
QNDYSYPYT

<SEQ ID NO:39>
QVQLVQSGAEVKKPGSSVKVSCKASGGTFSDYYMKWVRQAPGQGLEWMGDIIPSNGATFYNQKFKGRV
TITADESTSTAYMELSSLRSEDTAVYYCARSHLLRASWFAYWGQGTLVTVSSASTKGPSVFPLAPSSK
STSGGTAALGCLVKDYFPEPVTVSWNSGALTSGVHTFPAVLQSSGLYSLSSVVTVPSSSLGTQTYICN

FIG. 2D

VNHKPSNTKVDKKVEPKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKCKVSNKALPAPIEKTIS
KAKGQPREPQVYTLPPSRDELTKNQVSLTCLVKGFYPSDIAVEWESNGQPENNYKTTPPVLDSDGSFF
LYSKLTVDKSRWQQGNVFSCSVMHEALHNHYTQKSLSLSPG

<SEQ ID NO:40>
DIVMTQSPDSLAVSLGERATINCESSQSVLNSGNQKNYLTWYQQKPGQPPKLLIYWASTRESGVPDRF
SGSGSGTDFTLTISSLQAEDVAVYYCQNDYSYPYTFGQGTKLEIKRTVAAPSVFIFPPSDEQLKSGTA
SVVCLLNNFYPREAKVQWKVDNALQSGNSQESVTEQDSKDSTYSLSSTLTLSKADYEKHKVYACEVTH
QGLSSPVTKSFNRGEC

<SEQ ID NO:41>
EVQLVESGGGLIQPGGSLRLSCAASGFTFSTSGMHWFRQAPGKGLEWVAYISSSSGFVYADAVKGRFT
ISRDNSKNTLYLQMNSLRAEDTAVYYCARSEAAFWGQGTLVTVSS

<SEQ ID NO:42>
TSGMH

<SEQ ID NO:43>
YISSSSGFVYADAVKG

<SEQ ID NO:44>
SEAAF

<SEQ ID NO:45>
DIVMTQSPLSLPVTPGEPASISCRSQKSRLSRMGITPLNWYLQKPGQSPQLLIYRMSNLASGVPDRFS
GSGSGTDFTLKISRVEAEDVGVYYCAQFLEYPPTFGQGTKLEIK

<SEQ ID NO:46>
RSQKSRLSRMGITPLN

<SEQ ID NO:47>
RMSNLAS

<SEQ ID NO:48>
AQFLEYPPT

<SEQ ID NO:49>
EVQLVESGGGLIQPGGSLRLSCAASGFTFSTSGMHWFRQAPGKGLEWVAYISSSSGFVYADAVKGRFT
ISRDNSKNTLYLQMNSLRAEDTAVYYCARSEAAFWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSN
TKVDKKVEPKSCDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKTTPPVLDSDGSFFLYSKLTV
DKSRWQQGNVFSCSVMHEALHNHYTQKSLSLSPG

<SEQ ID NO:50>
DIVMTQSPLSLPVTPGEPASISCRSQKSRLSRMGITPLNWYLQKPGQSPQLLIYRMSNLASGVPDRFS
GSGSGTDFTLKISRVEAEDVGVYYCAQFLEYPPTFGQGTKLEIKRTVAAPSVFIFPPSDEQLKSGTAS
VVCLLNNFYPREAKVQWKVDNALQSGNSQESVTEQDSKDSTYSLSSTLTLSKADYEKHKVYACEVTHQ
GLSSPVTKSFNRGEC

FIG. 2E

<SEQ ID NO:51>
EVQLVESGGGLIQPGGSLRLSCAASGFTFSTSGMHWVRQAPGKGLEWVSYISSSSGFVYADAVKGRFT
ISRDNSKNTLYLQMNSLRAEDTAVYYCARSEAAFWGQGTLVTVSS

<SEQ ID NO:52>
TSGMH

<SEQ ID NO:53>
YISSSSGFVYADAVKG

<SEQ ID NO:54>
SEAAF

<SEQ ID NO:55>
DIVMTQSPLSLPVTPGEPASISCRSQKSRLSRMGITPLNWYLQKPGQSPQLLIYRMSNLASGVPDRFS
GSGSGTDFTLKISRVEAEDVGVYYCAQFLEYPPTFGQGTKLEIK

<SEQ ID NO:56>
RSQKSRLSRMGITPLN

<SEQ ID NO:57>
RMSNLAS

<SEQ ID NO:58>
AQFLEYPPT

<SEQ ID NO:59>
EVQLVESGGGLIQPGGSLRLSCAASGFTFSTSGMHWVRQAPGKGLEWVSYISSSSGFVYADAVKGRFT
ISRDNSKNTLYLQMNSLRAEDTAVYYCARSEAAFWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNHKPSN
TKVDKKVEPKSCDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKTTPPVLDSDGSFFLYSKLTV
DKSRWQQGNVFSCSVMHEALHNHYTQKSLSLSPG

<SEQ ID NO:60>
DIVMTQSPLSLPVTPGEPASISCRSQKSRLSRMGITPLNWYLQKPGQSPQLLIYRMSNLASGVPDRFS
GSGSGTDFTLKISRVEAEDVGVYYCAQFLEYPPTFGQGTKLEIKRTVAAPSVFIFPPSDEQLKSGTAS
VVCLLNNFYPREAKVQWKVDNALQSGNSQESVTEQDSKDSTYSLSSTLTLSKADYEKHKVYACEVTHQ
GLSSPVTKSFNRGEC

<SEQ ID NO:61>
MNYPLTLEMDLENLEDLFWELDRLDNYNDTSLVENHLCPATEGPLMASFKAVFVPVAYSLIFLLGVIG
NVLVLVILERHRQTRSSTETFLFHLAVADLLLVFILPFAVAEGSVGWVLGTFLCKTVIALHKVNFYCS
SLLLACIAVDRYLAIVHAVHAYRHRRLLSIHITCGTIWLVGFLLALPEILFAKVSQGHHNNSLPRCTF
SQENQAETHAWFTSRFLYHVAGFLLPMLVMGWCYVGVVHRLRQAQRRPQRQKAVRVAILVTSIFFLCW
SPYHIVIFLDTLARLKAVDNTCKLNGSLPVAITMCEFLGLAHCCLNPMLYTFAGVKFRSDLSRLLTKL
GCTGPASLCQLFPSWRRSSLSESENATSLTTF

<SEQ ID NO:62>

FIG. 2F

```
MVLLWLTLLLIALPCLLQTKEDPNPPITNLRMKAKAQQLTWDLNRNVTDIECVKDADYSMPAVNNSYC
QFGAISLCEVTNYTVRVANPPFSTWILFPENSGKPWAGAENLTCWIHDVDFLSCSWAVGPGAPADVQY
DLYLNVANRRQQYECLHYKTDAQGTRIGCRFDDISRLSSGSQSSHILVRGRSAAFGIPCTDKFVVFSQ
IEILTPPNMTAKCNKTHSFMHWKMRSHFNRKFRYELQIQKRMQPVITEQVRDRTSFQLLNPGTYTVQI
RARERVYEFLSAWSTPQRFECDQEEGANTRAWRTSLLIALGTLLALVCVFVICRRYLVMQRLFPRIPH
MKDPIGDSFQNDKLVVWEAGKAGLEECLVTEVQVVQKT
```

SPECIFIC ANTIBODY DRUG CONJUGATES (ADCS) HAVING KSP INHIBITORS

CROSS REFERENCE TO RELATED APPLICATIONS

This application is a national stage application under 35 U.S.C. § 371 of International Application No. PCT/EP2017/083313, filed internationally on Dec. 18, 2017, which claims the benefit of European Application No. 16205870.5, filed Dec. 21, 2016.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 777052035300SEQLIST.TXT, date recorded: Jun. 18, 2019, size: 62 KB).

INTRODUCTION AND STATE OF THE ART

The invention relates to specific binder-drug conjugates (ADCs) of kinesin spindle protein inhibitors, to effective metabolites of these ADCs, to processes for preparing these ADCs, to the use of these ADCs for the treatment and/or prevention of diseases and to the use of these ADCs for preparing medicaments for treatment and/or prevention of diseases, in particular hyperproliferative and/or angiogenic disorders such as, for example, cancer diseases. Such treatments can be effected as monotherapy or else in combination with other medicaments or further therapeutic measures.

Cancers are the consequence of uncontrolled cell growth of the most diverse tissues. In many cases the new cells penetrate into existing tissue (invasive growth), or they metastasize into remote organs. Cancers occur in a wide variety of different organs and often have tissue-specific courses. The term "cancer" as a generic term therefore describes a large group of defined diseases of different organs, tissue and cell types.

Some tumours at early stages can be removed by surgical and radiotherapy measures. Metastasized tumours as a rule can only be treated palliatively by chemotherapeutics. The aim here is to achieve the optimum combination of an improvement in the quality of life and prolonging of life.

Conjugates of binder proteins with one or more drug molecules are known, in particular in the form of antibody drug conjugates (ADCs) in which an internalizing antibody directed against a tumour-associated antigen is covalently attached via a linker to a cytotoxic agent. Following introduction of the ADCs into the tumour cell and subsequent dissociation of the conjugate, either the cytotoxic agent itself or a cytotoxic metabolite formed therefrom is released within the tumour cell and can unfold its action therein directly and selectively. In this manner, in contrast to conventional cancer chemotherapy, damage to normal tissue is contained in significantly narrower limits [see, for example, J. M. Lambert, Curr. Opin. Pharmacol. 5, 543-549 (2005); A. M. Wu and P. D. Senter, Nat. Biotechnol. 23, 1137-1146 (2005); P. D. Senter, Curr. Opin. Chem. Biol. 13, 235-244 (2009); L. Ducry and B. Stump, Bioconjugate Chem. 21, 5-13 (2010)]. Thus, WO2012/171020 describes ADCs in which a plurality of toxophore molecules are attached via a polymeric linker to an antibody. As possible toxophores, WO2012/171020 mentions, among others, the substances SB 743921, SB 715992 (Ispinesib), MK-0371, AZD8477, AZ3146 and ARRY-520.

The substances mentioned last are kinesin spindle protein inhibitors. Kinesin spindle protein (KSP, also known as Eg5, HsEg5, KNSL1 or KIF11) is a kinesin-like motorprotein which is essential for the bipolar mitotic spindle to function. Inhibition of KSP leads to mitotic arrest and, over a relatively long term, to apoptosis (Tao et al., Cancer Cell 2005 Jul. 8(1), 39-59). After the discovery of the first cell-penetrating KSP inhibitor, Monastrol, KSP inhibitors have established themselves as a class of novel chemotherapeutics (Mayer et al., Science 286: 971-974, 1999), and they are subject matter of a number of patent applications (e.g. WO2006/044825; WO2006/002236; WO2005/051922; WO2006/060737; WO03/060064; WO03/040979; and WO03/049527). However, since KSP is active only during a relatively short period of time during the mitosis phase, KSP inhibitors have to be present in a sufficiently high concentration during this phase. WO2014/151030 discloses ADCs including certain KSP inhibitors.

Further ADCs with KSP inhibitors have been disclosed in the patent applications WO2015/096982 and WO2016/096610.

SUMMARY OF THE INVENTION

Despite various disclosures of antibody-drug conjugates, it is an object of the present invention to provide substances which, after administration at a relatively low concentration, exhibit long-lasting apoptotic action and may therefore be of benefit for cancer therapy. Here, the profile of the metabolites released intracellularly from the ADCs plays an important role. Frequently, the metabolites formed from ADCs are substrates of efflux pumps and/or have high cell membrane permeability. Both phenomena may contribute to a short residence time and thus suboptimal apoptotic action in the tumour cell.

The present invention provides ADCs having a specific toxophor linker composition which in particular have an improved activity profile both in association with a specific anti-CD123 antibody and with an anti-CXCR5 antibody.

The antibody is preferably a humanized or chimeric monoclonal anti-CD123 antibody or an anti-CXCR5 antibody. Particular preference is given to the humanized anti-CD123 antibodies TPP-8987, TPP-8988 and TPP-9476 and to the humanized or chimeric anti-CXCR5 antibodies TPP-9024, TPP-9574 and TPP-9580.

It has now been found that antibody-drug conjugates (ADCs) of the formula (I)

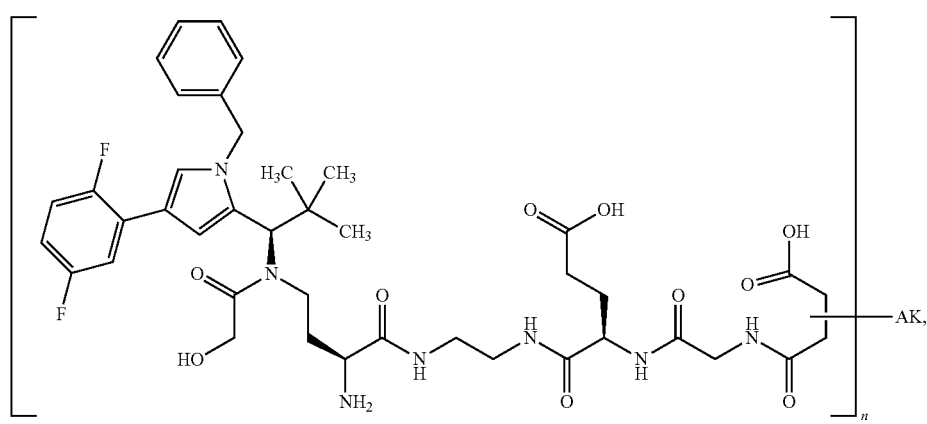

(I)

in which n represents 1 to 8,

AK represents an anti-CD123 antibody selected from the group consisting of TPP-8987, TPP-9476 and TPP-8988 or

AK represents an anti-CXCR5 antibody, preferably selected from the group consisting of TPP-9574, TPP-9580 and TPP-9024, or AK represents an antigen-binding fragment of these antibodies, where the antibody or the antigen-binding fragment is attached via a sulfur atom of a cysteine side group, and their salts, solvates and salts of these solvates, have superior properties compared to the known conjugates.

Preference is given to those antibody-drug conjugates (ADCs) of the formula (I), in which n represents 4 to 8.

Preference is given to those antibody-drug conjugates (ADCs) of the formula (I), in which AK represents an anti-CD123 antibody selected from the group consisting of TPP-8987, TPP-9476 and TPP-8988 and an antigen-binding fragment of these antibodies; particularly preferably AK represents TPP-9476, and an antigen-binding fragment of this antibody.

DESCRIPTION OF THE FIGURES

FIG. 1A-FIG. 1G: Annotated sequences of preferred antibodies for binder-drug conjugates. What are shown are the protein sequences of the heavy and light chains of the IgGs, and the VH and VL regions of these antibodies. Below the sequences, important regions are annotated (VH and VL regions in IgGs, and the CDR regions (H-CDR1, H-CDR2, H-CDR3, L-CDR1, L-CDR2, L-CDR3)). SEQ ID NOs of annotated sequences are as follows: TPP-8987 VH (PRT)—SEQ ID NO: 1, TPP-8987 VL (PRT)—SEQ ID NO: 5, TPP-8987 Heavy Chain (PRT)—SEQ ID NO: 9, TPP-8987 Light Chain (PRT)—SEQ ID NO: 10, TPP-8988 VH (PRT)—SEQ ID NO: 11, TPP-8988 VL (PRT)—SEQ ID NO: 15, TPP-8988 Heavy Chain (PRT)—SEQ ID NO: 19, TPP-8988 Light Chain (PRT)—SEQ ID NO: 20, TPP-9024 VH (PRT)—SEQ ID NO: 21, TPP-9024 VL (PRT)—SEQ ID NO: 25, TPP-9024 Heavy Chain (PRT)—SEQ ID NO: 29, TPP-9024 Light Chain (PRT)—SEQ ID NO: 30, TPP-9476 VH (PRT)—SEQ ID NO: 31, TPP-9476 VL (PRT)—SEQ ID NO: 35, TPP-9476 Heavy Chain (PRT)—SEQ ID NO: 39, TPP-9476 Light Chain (PRT)—SEQ ID NO: 40, TPP-9574 VH (PRT)—SEQ ID NO: 41, TPP-9574 VL (PRT)—SEQ ID NO: 45, TPP-9574 Heavy Chain (PRT)—SEQ ID NO: 49, TPP-9574 Light Chain (PRT)—SEQ ID NO: 50, TPP-9580 VH (PRT)—SEQ ID NO: 51, TPP-9580 VL (PRT)—SEQ ID NO: 55, TPP-9580 Heavy Chain (PRT)—SEQ ID NO: 59, and TPP-9580 Light Chain (PRT)—SEQ ID NO: 60.

FIG. 2A-FIG. 2F: Sequence listing of sequences of the preferred antibodies for binder-drug conjugates and of sequences of the target molecules.

DETAILED DESCRIPTION OF THE INVENTION

The invention provides conjugates of a humanized anti-CD123 antibody or a humanized or chimeric monoclonal anti-CXCR5 antibody, the drug molecule being a kinesin spindle protein inhibitor (KSP inhibitor) which is attached to the antibody via a linker L. Particular preference is given here to the humanized anti-CD123 antibodies TPP-8987, TPP-8988 and TPP-9476 and the humanized or chimeric anti-CXCR5 antibodies TPP-9024, TPP-9574 and TPP-9580.

Binders

In the broadest sense, the term "binder" is understood to mean a molecule which binds to a target molecule present at a certain target cell population to be addressed by the binder-drug conjugate. The term binder is to be understood in its broadest meaning and also comprises, for example, lectins, proteins capable of binding to certain sugar chains, or phospholipid-binding proteins. Such binders include, for example, high-molecular weight proteins (binding proteins), polypeptides or peptides (binding peptides), non-peptidic (e.g. aptamers (U.S. Pat. No. 5,270,163) review by Keefe A D., et al., Nat. Rev. Drug Discov. 2010; 9:537-550), or vitamins) and all other cell-binding molecules or substances. Binding proteins are, for example, antibodies and antibody fragments or antibody mimetics, for example affibodies, adnectins, anticalins, DARPins, avimers, nanobodies (review by Gebauer M. et al., Curr. Opinion in Chem. Biol. 2009; 13:245-255; Nuttall S. D. et al., Curr. Opinion in Pharmacology 2008; 8:608-617). Binding peptides are, for example, ligands of a ligand/receptor pair such as, for example, VEGF of the ligand/receptor pair VEGF/KDR, such as transferrin of the ligand/receptor pair transferrin/transferrin receptor or cytokine/cytokine receptor, such as TNFalpha of the ligand/receptor pair TNFalpha/TNFalpha receptor.

The binder may be a binding protein. Preferred embodiments of the binders are an antibody, an antigen-binding antibody fragment, a multispecific antibody or an antibody mimetic.

The literature also discloses various options of covalent coupling (conjugation) of organic molecules to binders and in particular antibodies. Preference according to the invention is given to the conjugation of the toxophores to the antibody via one or more sulfur atoms of cysteine residues of the antibody and/or via one or more NH groups of lysine residues of the antibody. However, it is also possible to bind the toxophore to the antibody via free carboxyl groups or via sugar residues of the antibody.

A "target molecule" in the broadest sense is understood to mean a molecule which is present in the target cell population and which may be a protein (for example a receptor of a growth factor) or a non-peptidic molecule (for example a sugar or phospholipid). It is preferably a receptor or an antigen.

The term "extracellular" target molecule describes a target molecule, attached to the cell, which is located at the outside of a cell, or the part of a target molecule which is located at the outside of a cell, i.e. a binder may bind on an intact cell to its extracellular target molecule. An extracellular target molecule may be anchored in the cell membrane or be a component of the cell membrane. The person skilled in the art is aware of methods for identifying extracellular target molecules. For proteins, this may be by determining the transmembrane domain(s) and the orientation of the protein in the membrane. These data are usually deposited in protein databases (e.g. SwissProt).

The term "cancer target molecule" describes a target molecule which is more abundantly present on one or more cancer cell species than on non-cancer cells of the same tissue type. Preferably, the cancer target molecule is selectively present on one or more cancer cell species compared with non-cancer cells of the same tissue type, where selectively describes an at least two-fold enrichment on cancer cells compared to non-cancer cells of the same tissue type (a "selective cancer target molecule"). The use of cancer target molecules allows the selective therapy of cancer cells using the conjugates according to the invention.

The binder can be attached to the linker via a bond. The binder can be linked by means of a heteroatom of the binder. Heteroatoms according to the invention of the binder which can be used for attachment are sulfur (in one embodiment via a sulfhydryl group of the binder), oxygen (according to the invention by means of a carboxyl or hydroxyl group of the binder) and nitrogen (in one embodiment via a primary or secondary amine group or amide group of the binder). These heteroatoms may be present in the natural binder or are introduced by chemical methods or methods of molecular biology. According to the invention, the attachment of the binder to the toxophore has only a minor effect on the binding activity of the binder with respect to the target molecule. In a preferred embodiment, the linkage has no effect on the binding activity of the binder with respect to the target molecule.

In accordance with the present invention, the term "antibody" is to be understood in its broadest meaning and comprises immunoglobulin molecules, for example intact or modified monoclonal antibodies, polyclonal antibodies or multispecific antibodies (e.g. bispecific antibodies). An immunoglobulin molecule preferably comprises a molecule having four polypeptide chains, two heavy chains (H chains) and two light chains (L chains) which are typically linked by disulfide bridges. Each heavy chain comprises a variable domain of the heavy chain (abbreviated VH) and a constant domain of the heavy chain. The constant domain of the heavy chain may, for example, comprise three domains CH1, CH2 and CH3. Each light chain comprises a variable domain (abbreviated VL) and a constant domain. The constant domain of the light chain comprises a domain (abbreviated CL). The VH and VL domains may be subdivided further into regions having hypervariability, also referred to as complementarity determining regions (abbreviated CDR) and regions having low sequence variability (framework region, abbreviated FR). Typically, each VH and VL region is composed of three CDRs and up to four FRs. For example from the amino terminus to the carboxy terminus in the following order: FR1, CDR1, FR2, CDR2, FR3, CDR3, FR4. An antibody may be obtained from any suitable species, e.g. rabbit, llama, camel, mouse or rat. In one embodiment, the antibody is of human or murine origin. An antibody may, for example, be human, humanized or chimeric.

The term "monoclonal" antibody refers to antibodies obtained from a population of substantially homogeneous antibodies, i.e. individual antibodies of the population are identical except for naturally occurring mutations, of which there may be a small number. Monoclonal antibodies recognize a single antigenic binding site with high specificity. The term monoclonal antibody does not refer to a particular preparation process.

The term "intact" antibody refers to antibodies comprising both an antigen-binding domain and the constant domain of the light and heavy chain. The constant domain may be a naturally occurring domain or a variant thereof having a number of modified amino acid positions, and may also be aglycosylated.

The term "modified intact" antibody refers to intact antibodies fused via their amino terminus or carboxy terminus by means of a covalent bond (e.g. a peptide bond) with a further polypeptide or protein not originating from an antibody. Furthermore, antibodies may be modified such that, at defined positions, reactive cysteines are introduced to facilitate coupling to a toxophore (see Junutula et al. Nat Biotechnol. 2008 August; 26(8):925-32).

"Amino acid modification" or "mutation" here means an amino acid substitution, insertion and/or deletion in a polypeptide sequence. The preferred amino acid modification here is a substitution. "Amino acid substitution" or "substitution" here means an exchange of an amino acid at a given position in a protein sequence for another amino acid. For example, the substitution Y50W describes a variant of a parent polypeptide in which the tyrosine at position 50 has been exchanged for a tryptophan. A "variant" of a polypeptide describes a polypeptide having an amino acid sequence substantially identical to a reference polypeptide, typically a native or "parent" polypeptide. The polypeptide variant may have one or more amino acid exchanges, deletions and/or insertions at particular positions in the native amino acid sequence.

The term "human" antibody refers to antibodies which can be obtained from a human or which are synthetic human antibodies. A "synthetic" human antibody is an antibody which is partially or entirely obtainable in silico from synthetic sequences based on the analysis of human antibody sequences. A human antibody can be encoded, for example, by a nucleic acid isolated from a library of antibody sequences of human origin. An example of such an antibody can be found in Söderlind et al., Nature Biotech. 2000, 18:853-856. Such "human" and "synthetic" antibodies also include aglycosylated variants which have been produced either by deglycosylation by PNGaseF or by mutation of N297 (Kabat numbering) of the heavy chain to any other amino acid.

The term "humanized" or "chimeric" antibody describes antibodies consisting of a non-human and a human portion of the sequence. In these antibodies, part of the sequences of the human immunoglobulin (recipient) is replaced by sequence portions of a non-human immunoglobulin (donor). In many cases, the donor is a murine immunoglobulin. In the case of humanized antibodies, amino acids of the CDR of the recipient are replaced by amino acids of the donor. Sometimes, amino acids of the framework, too, are replaced by corresponding amino acids of the donor. In some cases the humanized antibody contains amino acids present neither in the recipient nor in the donor, which were introduced during the optimization of the antibody. In the case of chimeric antibodies, the variable domains of the donor immunoglobulin are fused with the constant regions of a human antibody. Such "humanized" and "chimeric" antibodies also include aglycosylated variants which have been produced either by deglycosylation by PNGaseF or by mutation of N297 (Kabat numbering) of the heavy chain to any other amino acid.

The term complementarity determining region (CDR) as used herein refers to those amino acids of a variable antibody domain which are required for binding to the antigen. Typically, each variable region has three CDR regions referred to as CDR1, CDR2 and CDR3. Each CDR region may embrace amino acids according to the definition of Kabat and/or amino acids of a hypervariable loop defined according to Chotia. The definition according to Kabat comprises, for example, the region from about amino acid position 24-34 (CDR1), 50-56 (CDR2) and 89-97 (CDR3) of the variable light chain/domain (VL) and 31-35 (CDR1), 50-65 (CDR2) and 95-102 (CDR3) of the variable heavy chain/domain (VH) (Kabat et al., Sequences of Proteins of Immunological Interest, 5th Ed. Public Health Service, National Institutes of Health, Bethesda, Md. (1991)). The definition according to Chotia comprises, for example, the region from about amino acid position 26-32 (CDR1), 50-52 (CDR2) and 91-96 (CDR3) of the variable light chain (VL) and 26-32 (CDR1), 53-55 (CDR2) and 96-101 (CDR3) of the variable heavy chain (VH) (Chothia and Lesk; J Mol Biol 196: 901-917 (1987)). In some cases, a CDR may comprise amino acids from a CDR region defined according to Kabat and Chotia.

Depending on the amino acid sequence of the constant domain of the heavy chain, antibodies may be categorized into different classes. There are five main classes of intact antibodies: IgA, IgD, IgE, IgG and IgM, and several of these can be divided into further subclasses. (Isotypes), e.g. IgG1, IgG2, IgG3, IgG4, IgA1 and IgA2. The constant domains of the heavy chain, which correspond to the different classes, are referred to as [alpha/α], [delta/δ], [epsilon/ε], [gamma/γ] and [my/μ]. Both the three-dimensional structure and the subunit structure of antibodies are known.

The term "functional fragment" or "antigen-binding antibody fragment" of an antibody/immunoglobulin is defined as a fragment of an antibody/immunoglobulin (e.g. the variable domains of an IgG) which still comprise the antigen binding domains of the antibody/immunoglobulin. The "antigen binding domain" of an antibody typically comprises one or more hypervariable regions of an antibody, for example the CDR, CDR2 and/or CDR3 region. However, the "framework" or "skeleton" region of an antibody may also play a role during binding of the antibody to the antigen. The framework region forms the skeleton of the CDRs. Preferably, the antigen binding domain comprises at least amino acids 4 to 103 of the variable light chain and amino acids 5 to 109 of the variable heavy chain, more preferably amino acids 3 to 107 of the variable light chain and 4 to 111 of the variable heavy chain, especially preferably the complete variable light and heavy chains, i.e. amino acids 1-109 of the VL and 1 to 113 of the VH (numbering according to WO97/08320).

"Functional fragments" or "antigen-binding antibody fragments" of the invention encompass, non-conclusively, Fab, Fab', F(ab')₂ and Fv fragments, diabodies, Single Domain Antibodies (DAbs), linear antibodies, individual chains of antibodies (single-chain Fv, abbreviated to scFv); and multispecific antibodies, such as bi- and tri-specific antibodies, for example, formed from antibody fragments C. A. K Borrebaeck, editor (1995) Antibody Engineering (Breakthroughs in Molecular Biology), Oxford University Press; R. Kontermann & S. Duebel, editors (2001) Antibody Engineering (Springer Laboratory Manual), Springer Verlag. Antibodies other than "multispecific" or "multifunctional" antibodies are those having identical binding sites. Multispecific antibodies may be specific for different epitopes of an antigen or may be specific for epitopes of more than one antigen (see, for example, WO 93/17715; WO 92/08802; WO 91/00360; WO 92/05793; Tutt, et al., 1991, J. Immunol. 14760 69; U.S. Pat. Nos. 4,474,893; 4,714,681; 4,925,648; 5,573,920; 5,601,819; or Kostelny et al., 1992, J. Immunol. 148 1547 1553). An F(ab')₂ or Fab molecule may be constructed such that the number of intermolecular disulfide interactions occurring between the Ch1 and the CL domains can be reduced or else completely prevented.

"Epitopes" refer to protein determinants capable of binding specifically to an immunoglobulin or T cell receptors. Epitopic determinants usually consist of chemically active surface groups of molecules such as amino acids or sugar side chains or combinations thereof, and usually have specific 3-dimensional structural properties and also specific charge properties.

"Functional fragments" or "antigen-binding antibody fragments" may be fused with another polypeptide or protein, not originating from an antibody, via the amino terminus or carboxyl terminus thereof, by means of a covalent bond (e.g. a peptide linkage). Furthermore, antibodies and antigen-binding fragments may be modified by introducing reactive cysteines at defined locations, in order to facilitate coupling to a toxophore (see Junutula et al. Nat Biotechnol. 2008 August; 26(8):925-32).

Polyclonal antibodies can be prepared by methods known to a person of ordinary skill in the art. Monoclonal antibodies may be prepared by methods known to a person of ordinary skill in the art (Köhler and Milstein, Nature, 256, 495-497, 1975). Human and humanized monoclonal antibodies may be prepared by methods known to a person of ordinary skill in the art (Olsson et al., Meth Enzymol. 92, 3-16 or Cabilly et al U.S. Pat. No. 4,816,567 or Boss et al U.S. Pat. No. 4,816,397).

A person of ordinary skill in the art is aware of diverse methods for preparing human antibodies and fragments thereof, such as, for example, by means of transgenic mice (N Lonberg and D Huszar, Int Rev Immunol. 1995; 13(1): 65-93) or Phage Display Technologien (Clackson et al., Nature. 1991 Aug. 15; 352(6336):624-8). Antibodies of the invention may be obtained from recombinant antibody libraries consisting for example on the amino acid sequences of a multiplicity of antibodies compiled from a large number of healthy volunteers. Antibodies may also be produced by means of known recombinant DNA technologies. The nucleic acid sequence of an antibody can be obtained by routine sequencing or is available from publically accessible databases.

An "isolated" antibody or binder has been purified to remove other constituents of the cell. Contaminating constituents of a cell which may interfere with a diagnostic or therapeutic use are, for example, enzymes, hormones, or other peptidic or non-peptidic constituents of a cell. A preferred antibody or binder is one which has been purified to an extent of more than 95% by weight, relative to the antibody or binder (determined for example by Lowry method, UV-Vis spectroscopy or by SDS capillary gel electrophoresis). Moreover an antibody which has been purified to such an extent that it is possible to determine at least 15 amino acids of the amino terminus or of an internal amino acid sequence, or which has been purified to homogeneity, the homogeneity being determined by SDS-PAGE under reducing or non-reducing conditions (detection may be determined by means of Coomassie Blue staining or preferably by silver coloration). However, an antibody is normally prepared by one or more purification steps.

The term "specific binding" or "binds specifically" refers to an antibody or binder which binds to a predetermined antigen/target molecule. Specific binding of an antibody or binder typically describes an antibody or binder having an affinity of at least $10^{-7}$ M (as Kd value; i.e. preferably those with Kd values smaller than $10^{-7}$ M), with the antibody or binder having an at least two times higher affinity for the predetermined antigen/target molecule than for a non-specific antigen/target molecule (e.g. bovine serum albumin, or casein) which is not the predetermined antigen/target molecule or a closely related antigen/target molecule. Specific binding of an antibody or binder does not exclude the antibody or binder binding to a plurality of antigens/target molecules (e.g. orthologs of different species). The antibodies preferably have an affinity of at least $10^{-7}$ M (as Kd value; in other words preferably those with smaller Kd values than $10^{-7}$ M), preferably of at least $10^{-8}$ M, more preferably in the range from $10^{-9}$ M to $10^{-11}$ M. The Kd values may be determined, for example, by means of surface plasmon resonance spectroscopy.

The antibody-drug conjugates of the invention likewise exhibit affinities in these ranges. The affinity is preferably not substantially affected by the conjugation of the drugs (in general, the affinity is reduced by less than one order of magnitude, in other words, for example, at most from $10^{-8}$ M to $10^{-7}$ M).

The antibodies used in accordance with the invention are also notable preferably for a high selectivity. A high selectivity exists when the antibody of the invention exhibits an affinity for the target protein which is better by a factor of at least 2, preferably by a factor of 5 or more preferably by a factor of 10, than for an independent other antigen, e.g. human serum albumin (the affinity may be determined, for example, by means of surface plasmon resonance spectroscopy).

Furthermore, the antibodies of the invention that are used are preferably cross-reactive. In order to be able to facilitate and better interpret preclinical studies, for example toxicological or activity studies (e.g. in xenograft mice), it is advantageous if the antibody used in accordance with the invention not only binds the human target protein but also binds the species target protein in the species used for the studies. In one embodiment the antibody used in accordance with the invention, in addition to the human target protein, is cross-reactive to the target protein of at least one further species. For toxicological and activity studies it is preferred to use species of the families of rodents, dogs and non-human primates. Preferred rodent species are mouse and rat. Preferred non-human primates are rhesus monkeys, chimpanzees and long-tailed macaques.

In one embodiment the antibody used in accordance with the invention, in addition to the human target protein, is cross-reactive to the target protein of at least one further species selected from the group of species consisting of mouse, rat and long-tailed macaque (*Macaca fascicularis*). Especially preferred are antibodies used in accordance with the invention which in addition to the human target protein are at least cross-reactive to the mouse target protein. Preference is given to cross-reactive antibodies whose affinity for the target protein of the further non-human species differs by a factor of not more than 50, more particularly by a factor of not more than ten, from the affinity for the human target protein.

Antibodies Directed Against a Cancer Target Molecule

The target molecule towards which the binder, for example an antibody or an antigen-binding fragment thereof, is directed is preferably a cancer target molecule. The term "cancer target molecule" describes a target molecule which is more abundantly present on one or more cancer cell species than on non-cancer cells of the same tissue type. Preferably, the cancer target molecule is selectively present on one or more cancer cell species compared with non-cancer cells of the same tissue type, where selectively describes an at least two-fold enrichment on cancer cells compared to non-cancer cells of the same tissue type (a "selective cancer target molecule"). The use of cancer target molecules allows the selective therapy of cancer cells using the conjugates according to the invention.

Antibodies which are specific against an antigen, for example cancer cell antigen, can be prepared by a person of ordinary skill in the art by means of methods with which he or she is familiar (such as recombinant expression, for example) or may be acquired commercially (as for example from Merck KGaA, Germany). Examples of known commercially available antibodies in cancer therapy are Erbitux® (cetuximab, Merck KGaA), Avastin® (bevacizumab, Roche) and Herceptin® (trastuzumab, Genentech). Trastuzumab is a recombinant humanized monoclonal antibody of the IgG1kappa type which in a cell-based assay (Kd=5 nM) binds the extracellular domains of the human epidermal growth receptor with high affinity. The antibody is produced recombinantly in CHO cells. All these antibodies can also be produced as aglycosylated variants of these antibodies, either by deglycosylation by means of PNGase F or by mutation of N297 (Kabat numbering) of the heavy chain to any amino acid.

In the present invention, the cancer target molecules are
(1) the receptor protein CXCR5 (CD185; SwissProt: P32302; NCBI Gene ID 643, NCBI Reference Sequence: NP_001707.1; SEQ ID NO: 61)
(2) the surface receptor CD123 (IL3RA; NCBI Gene ID: 3563; NCBI Reference Sequence: NP_002174.1; SwissProt: P26951; SEQ ID NO: 62)

In particularly preferred subject of the invention, the binder binds specifically to an extracellular cancer target molecule selected from the group consisting of the cancer target molecules CXCR5 and CD123. In a preferred embodiment, the binder, after binding to its extracellular target molecule on the target cell, is internalized by the target cell through the binding. This causes the binder-drug conjugate, which may be an immuno-conjugate or an ADC, to be taken up by the target cell. The binder is then processed, preferably intracellularly, with preference lysosomally.

In one embodiment the binder is a binding protein. In a preferred embodiment the binder is an antibody, an antigen-binding antibody fragment, a multispecific antibody or an antibody mimetic.

Preferred antibody mimetics are affibodies, adnectins, anticalins, DARPins, avimers, or nanobodies. Preferred multispecific antibodies are bispecific and trispecific antibodies.

In a preferred embodiment the binder is an antibody or an antigen-binding antibody fragment, more preferably an isolated antibody or an isolated antigen-binding antibody fragment.

Preferred antigen-binding antibody fragments are Fab, Fab', F(ab')2 and Fv fragments, diabodies, DAbs, linear antibodies and scFv. Particularly preferred are Fab, diabodies and scFv.

In a particularly preferred embodiment the binder is an antibody. Particularly preferred are monoclonal antibodies or antigen-binding antibody fragments thereof. Further particularly preferred are human, humanized or chimeric antibodies or antigen-binding antibody fragments thereof.

Antibodies or antigen-binding antibody fragments which bind cancer target molecules may be prepared by a person of ordinary skill in the art using known processes, such as, for example, chemical synthesis or recombinant expression. Binders for cancer target molecules may be acquired commercially or may be prepared by a person of ordinary skill in the art using known processes, such as, for example, chemical synthesis or recombinant expression. Further processes for preparing antibodies or antigen-binding antibody fragments are described in WO 2007/070538 (see page 22 "Antibodies"). The person skilled in the art knows how processes such as phage display libraries (e.g. Morphosys HuCAL Gold) can be compiled and used for discovering antibodies or antigen-binding antibody fragments (see WO 2007/070538, page 24 ff and AK Example 1 on page 70, AK Example 2 on page 72). Further processes for preparing antibodies that use DNA libraries from B cells are described for example on page 26 (WO 2007/070538). Processes for humanizing antibodies are described on page 30-32 of WO2007070538 and in detail in Queen, et al., Pros. Natl. Acad. Sci. USA 8610029-10033, 1989 or in WO 90/0786. Furthermore, processes for recombinant expression of proteins in general and of antibodies in particular are known to the person skilled in the art (see, for example, in Berger and Kimmel (Guide to Molecular Cloning Techniques, Methods in Enzymology, Vol. 152, Academic Press, Inc.); Sambrook, et al., (Molecular Cloning A Laboratory Manual, (Second Edition, Cold Spring Harbor Laboratory Press; Cold Spring Harbor, N.Y.; 1989) Vol. 1-3); Current Protocols in Molecular Biology, (F. M. Ausabel et al. [Eds.], Current Protocols, Green Publishing Associates, Inc./John Wiley & Sons, Inc.); Harlow et al., (Monoclonal Antibodies A Laboratory Manual, Cold Spring Harbor Laboratory Press (19881, Paul [Ed.]); Fundamental Immunology, (Lippincott Williams & Wilkins (1998)); and Harlow, et al., (Using Antibodies A Laboratory Manual, Cold Spring Harbor Laboratory Press (1998)). The person skilled in the art knows the corresponding vectors, promoters and signal peptides which are necessary for the expression of a protein/antibody. Commonplace processes are also described in WO 2007/070538 on pages 41-45. Processes for preparing an IgG1 antibody are described for example in WO 2007/070538 in Example 6 on page 74 ff. Processes which allow the determination of the internalization of an antibody after binding to its antigen are known to the skilled person and are described for example in WO 2007/070538 on page 80. The person skilled in the art is able to use the processes described in WO 2007/070538 that have been used for preparing carboanhydrase IX (Mn) antibodies in analogy for the preparation of antibodies with different target molecule specificity.

Bacterial Expression

The person skilled in the art is aware of the way in which antibodies, antigen-binding fragments thereof or variants thereof can be produced with the aid of bacterial expression.

Suitable expression vectors for bacterial expression of desired proteins are constructed by insertion of a DNA sequence which encodes the desired protein within the functional reading frame together with suitable translation initiation and translation termination signals and with a functional promoter. The vector comprises one or more phenotypically selectable markers and a replication origin in order to enable the retention of the vector and, if desired, the amplification thereof within the host. Suitable prokaryotic hosts for transformation include but are not limited to *E. coli, Bacillus subtilis, Salmonella typhimurium* and various species from the genus *Pseudomonas, Streptomyces*, and *Staphylococcus*. Bacterial vectors may be based, for example, on bacteriophages, plasmids, or phagemids. These vectors may contain selectable markers and a bacterial replication origin, which are derived from commercially available plasmids. Many commercially available plasmids typically contain elements of the well-known cloning vector pBR322 (ATCC 37017). In bacterial systems, a number of advantageous expression vectors can be selected on the basis of the intended use of the protein to be expressed.

After transformation of a suitable host strain and growth of the host strain to an appropriate cell density, the selected promoter is de-reprimed/induced by suitable means (for example a change in temperature or chemical induction), and the cells are cultivated for an additional period. The cells are typically harvested by centrifugation and if necessary digested in a physical manner or by chemical means, and the resulting raw extract is retained for further purification.

Therefore, a further embodiment of the present invention is an expression vector comprising a nucleic acid which encodes a novel antibody of the present invention.

Antibodies of the present invention or antigen-binding fragments thereof include naturally purified products, products which originate from chemical syntheses, and products which are produced by recombinant technologies in pro-karyotic hosts, for example *E. coli, Bacillus subtilis, Salmonella typhimurium* and various species from the genus *Pseudomonas, Streptomyces*, and *Staphylococcus*, preferably *E. coli*.

Mammalian Cell Expression

The person skilled in the art is aware of the way in which antibodies, antigen-binding fragments thereof or variants thereof can be produced with the aid of mammalian cell expression.

Preferred regulatory sequences for expression in mammalian cell hosts include viral elements which lead to high expression in mammalian cells, such as promoters and/or expression amplifiers derived from cytomegalovirus (CMV) (such as the CMV promoter/enhancer), simian virus 40 (SV40) (such as the SV40 promoter/enhancer), from adenovirus, (for example the adenovirus major late promoter (AdMLP)) and from polyoma. The expression of the antibodies may be constitutive or regulated (for example induced by addition or removal of small molecule inductors such as tetracycline in combination with the Tet system).

For further description of viral regulatory elements and sequences thereof, reference is made, for example, to U.S. Pat. No. 5,168,062 by Stinski, U.S. Pat. No. 4,510,245 by Bell et al. and U.S. Pat. No. 4,968,615 by Schaffner et al. The recombinant expression vectors may likewise include a replication origin and selectable markers (see, for example, U.S. Pat. Nos. 4,399,216, 4,634,665 and 5,179,017). Suitable selectable markers include genes which impart resistance to substances such as G418, puromycin, hygromycin, blasticidin, zeocin/bleomycin, or methotrexate, or selectable markers which lead to auxotrophy of a host cell, such as glutamine synthetase (Bebbington et al., Biotechnology (N Y). 1992 February; 10(2):169-75), when the vector has been introduced into the cell.

For example, the dihydrofolate reductase (DHFR) gene imparts resistance to methotrexate, the neo gene imparts resistance to G418, the bsd gene from *Aspergillus terreus* imparts resistance to blasticidin, puromycin N-acetyltransferase imparts resistance to puromycin, the Sh ble gene product imparts resistance to zeocin, and resistance to hygromycin is imparted by the *E. coli* hygromycin resistance gene (hyg or hph). Selectable markers such as DHFR or glutamine synthetase are also helpful for amplification techniques in conjunction with MTX and MSX.

The transfection of an expression vector into a host cell can be executed with the aid of standard techniques, including by electroporation, nucleofection, calcium phosphate precipitation, lipofection, polycation-based transfection such as polyethyleneimine (PEI)-based transfection and DEAE-dextran transfection.

Suitable mammalian host cells for the expression of antibodies, antigen-binding fragments thereof, or variants thereof include Chinese hamster ovary (CHO) cells such as CHO-K1, CHO-S, CHO-K1SV [including DHFR-CHO cells, described in Urlaub and Chasin, (1980) Proc. Natl. Acad. Sci. USA 77:4216-4220 and Urlaub et al., Cell. 1983 June; 33(2):405-12, used with a DHFR-selectable marker, as described in R. J. Kaufman and P. A. Sharp (1982) Mol. Biol. 159:601-621, and other knockout cells, as detailed in Fan et al., Biotechnol Bioeng. 2012 April; 109(4):1007-15), NS0 myeloma cells, COS cells, HEK293 cells, HKB11 cells, BHK21 cells, CAP cells, EB66 cells, and SP2 cells.

The expression of antibodies, antigen-binding fragments thereof, or variants thereof can also be effected in a transient or semi-stable manner in expression systems such as HEK293, HEK293T, HEK293-EBNA, HEK293E, HEK293-6E, HEK293 Freestyle, HKB11, Expi293F, 293EBNALT75, CHO Freestyle, CHO-S, CHO-K1, CHO-K1SV, CHOEBNALT85, CHOS-XE, CHO-3E7 or CAP-T cells (for example like Durocher et al., Nucleic Acids Res. 2002 Jan. 15; 30(2):E9)

In some embodiments, the expression vector is constructed in such a way that the protein to be expressed is secreted into the cell culture medium in which the host cells are growing. The antibodies, the antigen-binding fragments thereof, or the variants thereof can be obtained from the cell culture medium with the aid of protein purification methods known to those skilled in the art.

Purification

The antibodies, the antigen-binding fragments thereof, or the variants thereof can be obtained and purified from recombinant cell cultures with the aid of well-known methods, examples of which include ammonium sulfate or ethanol precipitation, acid extraction, protein A chromatography, protein G chromatography, anion or cation exchange chromatography, phosphocellulose chromatography, hydrophobic interaction chromatography (HIC), affinity chromatography, hydroxyapatite chromatography and lectin chromatography. High-performance liquid chromatography ("HPLC") can likewise be employed for purification. See, for example, Colligan, Current Protocols in Immunology, or Current Protocols in Protein Science, John Wiley & Sons, NY, N.Y., (1997-2001), e.g., Chapters 1, 4, 6, 8, 9, 10.

Antibodies of the present invention or antigen-binding fragments thereof, or variants thereof include naturally purified products, products from chemical synthesis methods and products which are produced with the aid of recombinant techniques in prokaryotic or eukaryotic host cells. Eukaryotic hosts include, for example, yeast cells, higher plant cells, insect cells and mammalian cells. Depending on the host cell chosen for the recombinant expression, the protein expressed may be in glycosylated or non-glycosylated form.

In a preferred embodiment, the antibody is purified (1) to an extent of more than 95% by weight, measured, for example, by the Lowry method, by UV-vis spectroscopy or by SDS capillary gel electrophoresis (for example with a Caliper LabChip GXII, GX 90 or Biorad Bioanalyzer instrument), and in more preferred embodiments more than 99% by weight, (2) to a degree suitable for determination of at least 15 residues of the N-terminal or internal amino acid sequence, or (3) to homogeneity determined by SDS-PAGE under reducing or non-reducing conditions with the aid of Coomassie blue or preferably silver staining.

Usually, an isolated antibody is obtained with the aid of at least one protein purification step.

Anti-CD123 Antibodies

According to the invention, it is possible to use anti-CD123 antibodies.

The expression "anti-CD123 antibody" or "an antibody which binds specifically to CD123" relates to an antibody which binds the cancer target molecule CD123 (NCBI Reference sequence: NP_002174.1; SEQ ID NO: 62), preferably with an affinity sufficient for a diagnostic and/or therapeutic application. In particular embodiments, the antibody binds CD123 with a dissociation constant ($K_D$) of ≤1 µM, ≤100 nM, ≤10 nM, ≤1 nM, ≤0.1 nM, ≤0.01 nM, or ≤0.001 nM.

Sun et al. (Sun et al., 1996, Blood 87(1) 83-92) describe the generation and properties of the monoclonal antibody 7G3, which binds the N-terminal domain of IL-3Rα, CD123. U.S. Pat. No. 6,177,078 (Lopez) relates to the anti-CD123 antibody 7G3. A chimeric variant of this antibody (CSL360) is described in WO 2009/070844, and a humanized version (CSL362) in WO 2012/021934. The sequence of the 7G3 antibody is disclosed in EP2426148. This sequence constitutes the starting point for the humanized antibodies obtained by CDR grafting.

An antibody which, after cell surface antigen binding, is internalized particularly well is the anti-CD123 antibody 12F1 disclosed by Kuo et al. (Kuo et al., 2009, Bioconjug Chem. 20(10):1975-82). The antibody 12F1 binds with higher affinity to CD123 than the antibody 7G3 and, after cell surface antigen binding, is internalized markedly faster than 7G3. Bispecific scFv immunofusion proteins based on 12F1 are disclosed in WO 2013/173820. Antibody TPP-6013 is a chimeric variant of 12F1.

The invention relates in particular to conjugates with antibodies or antigen-binding antibody fragments thereof or variants thereof derived from the antibodies 7G3 (Sun et al., 1996, Blood 87(1):83-92) and 12F1 (Kuo et al., 2009, Bioconjug Chem. 20(10):1975-82) originating from the mouse, or to conjugates with antibodies or antigen-binding antibody fragments thereof or variants thereof derived from the antibody 12F1 (Kuo et al., 2009, Bioconjug Chem. 20(10):1975-82) originating from the mouse.

Particular preference is given in the context of the present invention to the anti-CD123 antibodies TPP-9476, TPP-8988 and TPP-8987.

Anti-CXCR5 Antibodies

According to the invention, it is possible to use anti-CXCR5 antibodies.

The expression "anti-CXCR5 antibody" or "an antibody which binds specifically to CXCR5" relates to an antibody which binds the cancer target molecule CXCR5 (NCBI Reference Sequence: NP_001707.1; SEQ ID NO: 61), preferably with an affinity sufficient for a diagnostic and/or therapeutic application. In particular embodiments, the antibody binds CXCR5 with a dissociation constant ($K_D$) of ≤1 µM, ≤100 nM, ≤10 nM, ≤1 nM, ≤0.1 nM, ≤0.01 nM, or ≤0.001 nM.

Examples of antibodies and antigen-binding fragments which bind to CXCR5 are known to those skilled in the art and are described, for example, in EP2195023.

The hybridoma cells for the rat antibody RF8B2 (ACC2153) were purchased from DSMZ and the sequence of the antibody was identified by standard methods. TPP-9024 a chimeric variant of this antibody with a point mutation at position 67 (S67F) was prepared.

Furthermore, the rat antibody sequence constituted the starting point for the humanized antibodies obtained by CDR grafting into human framework.

These antibodies and antigen-binding fragments can be used in the context of this invention.

Particular preference is given in the context of the present invention to the humanized anti-CXCR5 antibodies TPP-9574, TPP-9580 and the chimeric antibody TPP-9024.

Preferred Antibodies and Antigen-Binding Antibody Fragments for Binder-Drug Conjugates According to the Invention In this application, in the context of the binder-drug conjugates, reference is made to the following preferred antibodies as shown in the following table: anti-CD123 antibodies TPP-8987, TPP-8988 and TPP-9476 and the anti-CXCR5 antibodies TPP-9024, TPP-9574 and TPP-9580.

TPP-8987 is an anti-CD123 antibody comprising a variable region of the heavy chain (VH) comprising the variable CDR1 sequence of the heavy chain (H-CDR1), as shown by SEQ ID NO: 2, the variable CDR2 sequence of the heavy chain (H-CDR2), as shown by SEQ ID NO: 3 and the variable CDR3 sequence of the heavy chain (H-CDR3), as shown by SEQ ID NO: 4, and a variable region of the light chain (VL) comprising the variable CDR1 sequence of the light chain (L-CDR1), as shown by SEQ ID NO: 6, the variable CDR2 sequence of the light chain (L-CDR2), as shown by SEQ ID NO: 7 and the variable CDR3 sequence of the light chain (L-CDR3), as shown by SEQ ID NO: 8.

TPP-8988 is an anti-CD123 antibody comprising a variable region of the heavy chain (VH) comprising the variable CDR1 sequence of the heavy chain (H-CDR1), as shown by SEQ ID NO: 12, the variable CDR2 sequence of the heavy chain (H-CDR2), as shown by SEQ ID NO: 13 and the variable CDR3 sequence of the heavy chain (H-CDR3), as shown by SEQ ID NO: 14, and a variable region of the light chain (VL) comprising the variable CDR1 sequence of the light chain (L-CDR1), as shown by SEQ ID NO: 16, the variable CDR2 sequence of the light chain (L-CDR2), as shown by SEQ ID NO: 17 and the variable CDR3 sequence of the light chain (L-CDR3), as shown by SEQ ID NO: 18.

TPP-9024 is an anti-CXCR5 antibody comprising a variable region of the heavy chain (VH) comprising the variable CDR1 sequence of the heavy chain (H-CDR1), as shown by SEQ ID NO: 22, the variable CDR2 sequence of the heavy chain (H-CDR2), as shown by SEQ ID NO: 23 and the variable CDR3 sequence of the heavy chain (H-CDR3), as shown by SEQ ID NO: 24, and a variable region of the light chain (VL) comprising the variable CDR1 sequence of the light chain (L-CDR1), as shown by SEQ ID NO: 26, the variable CDR2 sequence of the light chain (L-CDR2), as shown by SEQ ID NO: 27 and the variable CDR3 sequence of the light chain (L-CDR3), as shown by SEQ ID NO: 28.

TPP-9476 is an anti-CD123 antibody comprising a variable region of the heavy chain (VH) comprising the variable CDR1 sequence of the heavy chain (H-CDR1), as shown by SEQ ID NO: 32, the variable CDR2 sequence of the heavy chain (H-CDR2), as shown by SEQ ID NO: 33 and the variable CDR3 sequence of the heavy chain (H-CDR3), as shown by SEQ ID NO: 34, and a variable region of the light chain (VL) comprising the variable CDR1 sequence of the light chain (L-CDR1), as shown by SEQ ID NO: 36, the variable CDR2 sequence of the light chain (L-CDR2), as shown by SEQ ID NO: 37 and the variable CDR3 sequence of the light chain (L-CDR3), as shown by SEQ ID NO: 38.

TPP-9574 is an anti-CXCR5 antibody comprising a variable region of the heavy chain (VH) comprising the variable CDR1 sequence of the heavy chain (H-CDR1), as shown by SEQ ID NO: 42, the variable CDR2 sequence of the heavy

TABLE

Protein sequences of the preferred antibodies:

| Antibody TPP-XXX | Antigen | SEQ ID NO: VH | SEQ ID NO: H-CDR1 | SEQ ID NO: H-CDR2 | SEQ ID NO: H-CDR3 | SEQ ID NO: VL | SEQ ID NO: L-CDR1 | SEQ ID NO: L-CDR2 | SEQ ID NO: L-CDR3 | SEQ ID NO: IgG heavy chain | SEQ ID NO: IgG light chain |
|---|---|---|---|---|---|---|---|---|---|---|---|
| TPP-8987 | CD123 | 1 | 2 | 3 | 4 | 5 | 6 | 7 | 8 | 9 | 10 |
| TPP-8988 | CD123 | 11 | 12 | 13 | 14 | 15 | 16 | 17 | 18 | 19 | 20 |
| TPP-9024 | CXCR5 | 21 | 22 | 23 | 24 | 25 | 26 | 27 | 28 | 29 | 30 |
| TPP-9476 | CD123 | 31 | 32 | 33 | 34 | 35 | 36 | 37 | 38 | 39 | 40 |
| TPP-9574 | CXCR5 | 41 | 42 | 43 | 44 | 45 | 46 | 47 | 48 | 49 | 50 |
| TPP-9580 | CXCR5 | 51 | 52 | 53 | 54 | 55 | 56 | 57 | 58 | 59 | 60 |

TPP-8987, TPP-8988, TPP-9476, TPP-9024, TPP-9574 and TPP-9580 are antibodies comprising one or more of the CDR sequences specified in the above table (H-CDR1, H-CDR2, H-CDR3, L-CDR1, L-CDR2, L-CDR3) in the variable region of the heavy chain (VH) or the variable region of the light chain (VL). Preferably, the antibodies comprise the specified variable region of the heavy chain (VH) and/or the variable region of the light chain (VL). Preferably, the antibodies comprise the specified region of the heavy chain (IgG heavy chain) and/or the specified region of the light chain (IgG light chain).

chain (H-CDR2), as shown by SEQ ID NO: 33 and the variable CDR3 sequence of the heavy chain (H-CDR3), as shown by SEQ ID NO: 34, and a variable region of the light chain (VL) comprising the variable CDR1 sequence of the light chain (L-CDR1), as shown by SEQ ID NO: 36, the variable CDR2 sequence of the light chain (L-CDR2), as shown by SEQ ID NO: 37 and the variable CDR3 sequence of the light chain (L-CDR3), as shown by SEQ ID NO: 38.

TPP-9574 is an anti-CXCR5 antibody comprising a variable region of the heavy chain (VH) comprising the variable CDR1 sequence of the heavy chain (H-CDR1), as shown by SEQ ID NO: 42, the variable CDR2 sequence of the heavy chain (H-CDR2), as shown by SEQ ID NO: 43 and the variable CDR3 sequence of the heavy chain (H-CDR3), as shown by SEQ ID NO: 44, and a variable region of the light chain (VL) comprising the variable CDR1 sequence of the light chain (L-CDR1), as shown by SEQ ID NO: 46, the variable CDR2 sequence of the light chain (L-CDR2), as shown by SEQ ID NO: 47 and the variable CDR3 sequence of the light chain (L-CDR3), as shown by SEQ ID NO: 48.

TPP-9580 is an anti-CXCR5 antibody comprising a variable region of the heavy chain (VH) comprising the variable CDR1 sequence of the heavy chain (H-CDR1), as shown by SEQ ID NO: 52, the variable CDR2 sequence of the heavy chain (H-CDR2), as shown by SEQ ID NO: 53 and the variable CDR3 sequence of the heavy chain (H-CDR3), as shown by SEQ ID NO: 54, and a variable region of the light chain (VL) comprising the variable CDR1 sequence of the light chain (L-CDR1), as shown by SEQ ID NO: 56, the variable CDR2 sequence of the light chain (L-CDR2), as shown by SEQ ID NO: 57 and the variable CDR3 sequence of the light chain (L-CDR3), as shown by SEQ ID NO: 58.

TPP-8987 is an anti-CD123 antibody comprising preferably a variable region of the heavy chain (VH) as shown in SEQ ID NO: 1 and a variable region of the light chain (VL) as shown in SEQ ID NO: 5.

TPP-8988 is an anti-CD123 antibody comprising preferably a variable region of the heavy chain (VH) as shown in SEQ ID NO: 11 and a variable region of the light chain (VL) as shown in SEQ ID NO: 15.

TPP-9024 is an anti-CXCR5 antibody comprising preferably a variable region of the heavy chain (VH) as shown in SEQ ID NO: 21 and a variable region of the light chain (VL) as shown in SEQ ID NO: 25.

TPP-9476 is an anti-CD123 antibody comprising preferably a variable region of the heavy chain (VH) as shown in SEQ ID NO: 31 and a variable region of the light chain (VL) as shown in SEQ ID NO: 35.

TPP-9574 is an anti-CXCR5 antibody comprising preferably a variable region of the heavy chain (VH) as shown in SEQ ID NO: 41 and a variable region of the light chain (VL) as shown in SEQ ID NO: 45.

TPP-9580 is an anti-CXCR5 antibody comprising preferably a variable region of the heavy chain (VH) as shown in SEQ ID NO: 51 and a variable region of the light chain (VL) as shown in SEQ ID NO: 55.

TPP-8987 is an anti-CD123 antibody comprising preferably a region of the heavy chain as shown in SEQ ID NO: 9 and a region of the light chain as shown in SEQ ID NO: 10.

TPP-8988 is an anti-CD123 antibody comprising preferably a region of the heavy chain as shown in SEQ ID NO: 19 and a region of the light chain as shown in SEQ ID NO: 20.

TPP-9024 is an anti-CXCR5 antibody comprising preferably a region of the heavy chain as shown in SEQ ID NO: 29 and a region of the light chain as shown in SEQ ID NO: 30.

TPP-9476 is an anti-CD123 antibody comprising preferably a region of the heavy chain as shown in SEQ ID NO: 39 and a region of the light chain as shown in SEQ ID NO: 40.

TPP-9574 is an anti-CXCR5 antibody comprising preferably a region of the heavy chain as shown in SEQ ID NO: 49 and a region of the light chain as shown in SEQ ID NO: 50.

TPP-9580 is an anti-CXCR5 antibody comprising preferably a region of the heavy chain as shown in SEQ ID NO: 59 and a region of the light chain as shown in SEQ ID NO: 60.

Therapeutic Use

The hyper-proliferative diseases, for the treatment of which the compounds according to the invention may be employed, include in particular the group of cancer and tumour diseases. In the context of the present invention, these are understood to mean especially the following diseases, but without any limitation thereto: mammary carcinomas and mammary tumours (mammary carcinomas including ductal and lobular forms, also in situ), tumours of the respiratory tract (small-cell and non-small cell carcinoma, bronchial carcinoma), cerebral tumours (e.g. of the brain stem and of the hypothalamus, astrocytoma, ependymoma, glioblastoma, glioma, medulloblastoma, meningioma and neuro-ectodermal and pineal tumours), tumours of the digestive organs (carcinomas of the oesophagus, stomach, gall bladder, small intestine, large intestine, rectum and anal carcinomas), liver tumours (inter alia hepatocellular carcinoma, cholangiocarcinoma and mixed hepatocellular cholangiocarcinoma), tumours of the head and neck region (larynx, hypopharynx, nasopharynx, oropharynx, lips and oral cavity carcinomas, oral melanomas), skin tumours (basaliomas, spinaliomas, squamous cell carcinomas, Kaposi's sarcoma, malignant melanoma, non-melanomatous skin cancer, Merkel cell skin cancer, mast cell tumours), tumours of connective tissue (inter alia soft tissue sarcomas, osteosarcomas, malignant fibrous histiocytomas, chondrosarcomas, fibrosarcomas, haemangiosarcomas, leiomyosarcomas, liposarcomas, lymphosarcomas and rhabdomyosarcomas), tumours of the eyes (inter alia intraocular melanoma and retinoblastoma), tumours of the endocrine and exocrine glands (e.g. of the thyroid and parathyroid glands, pancreas and salivary gland carcinomas, adenocarcinomas), tumours of the urinary tract (tumours of the bladder, penis, kidney, renal pelvis and ureter) and tumours of the reproductive organs (carcinomas of the endometrium, cervix, ovary, vagina, vulva and uterus in women and carcinomas of the prostate and testes in men). These also include proliferative diseases of the blood, the lymph system and the spinal cord, in solid form and as circulating cells, such as leukaemias, lymphomas and myeloproliferative diseases, for example acute myeloid, acute lymphoblastic, chronic lymphocytic, chronic myelogenous and hairy cell leukaemia, and AIDS-correlated lymphomas, Hodgkin's lymphomas, non-Hodgkin's lymphomas, cutaneous T cell lymphomas, Burkitt's lymphomas and lymphomas in the central nervous system.

These well-characterized diseases in humans can also occur with a comparable aetiology in other mammals and can likewise be treated there with the compounds of the present invention.

The antibody-drug conjugates (ADCs) described herein and directed against CD123 can be used for the treatment of CD123-expressing disorders, such as CD123-expressing cancer diseases. Typically, such cancer cells exhibit measurable amounts of CD123 measured at the protein (e.g. using an immunoassay) or RNA level. Some of these cancer tissues show an elevated level of CD123 compared to non-cancerogenous tissue of the same type, preferably measured in the same patient. Optionally, the CD123 content is measured prior to the start of the cancer treatment with an antibody-drug conjugate (ADC) according to the invention (patient stratification). The antibody-drug conjugates (ADCs) directed against CD123 can be used for the treatment of CD123-expressing disorders, such as CD123-expressing cancer diseases, such as tumours of the haematopoietic and lymphatic tissue or haematopoietic and lymphatic malignant tumours. Examples of cancer diseases associated with CD123 expression include myeloid diseases such as acute myeloid leukaemia (AML) and myelodysplastic syndrome (MDS). Other types of cancer include B-cell acute lymphoblastic leukaemia (B-ALL), hairy cell leukaemia, blastic plasmacytoid dendritic cell neoplasm (BPDCN), Hodgkin's lymphoma, immature T-cell acute lymphoblastic leukaemia (immature T-ALL), Burkitt's lymphoma, follicular lymphoma, chronic lymphocytic leukaemia (CLL), mantle cell lymphoma (MCL). Methods of the described invention comprise the treatment of patients suffering from CD123-expressing cancer, the method comprising the administration of an antibody-drug conjugate (ADC) according to the invention.

The treatment of the cancer diseases mentioned above with the compounds according to the invention comprises both a treatment of the solid tumours and a treatment of metastasizing or circulating forms thereof.

In the context of this invention, the term "treatment" or "treat" is used in the conventional sense and means attending to, caring for and nursing a patient with the aim of combating, reducing, attenuating or alleviating a disease or health abnormality, and improving the living conditions impaired by this disease, as, for example, in the event of a cancer.

The present invention thus further provides for the use of the compounds of the invention for treatment and/or prevention of disorders, especially of the aforementioned disorders.

The present invention further provides for the use of the compounds of the invention for production of a medicament for treatment and/or prevention of disorders, especially of the aforementioned disorders.

The present invention further provides for the use of the compounds of the invention in a method for treatment and/or prevention of disorders, especially of the aforementioned disorders.

The present invention further provides a method of treatment and/or prevention of disorders, especially of the aforementioned disorders, using an effective amount of at least one of the compounds of the invention.

The compounds of the invention can be used alone or, if required, in combination with one or more other pharmacologically active substances, provided that this combination does not lead to undesirable and unacceptable side effects. The present invention therefore further provides medicaments comprising at least one of the compounds of the invention and one or more further drugs, especially for treatment and/or prevention of the aforementioned disorders.

For example, the compounds of the present invention can be combined with known anti-hyper-proliferative, cytostatic, cytotoxic or immunotherapeutic substances for the treatment of cancer diseases. Examples of suitable combination drugs include:

131I-chTNT, abarelix, abiraterone, aclarubicin, adalimumab, ado-trastuzumab emtansine, afatinib, aflibercept, aldesleukin, alemtuzumab, alendronic acid, alitretinoin, altretamine, amifostine, aminoglutethimide, hexyl-5-aminolevulinate, amrubicin, amsacrine, anastrozole, ancestim, anethole dithiolethione, anetumab ravtansine, angiotensin II, antithrombin III, aprepitant, arcitumomab, arglabin, arsenic trioxide, asparaginase, atezolizumab, avelumab, axitinib, azacitidine, belotecan, bendamustine, besilesomab, belinostat, bevacizumab, bexarotene, bicalutamide, bisantrene, bleomycin, blinatumomab, bortezomib, buserelin, bosutinib, brentuximab vedotin, busulfan, cabazitaxel, cabozantinib, calcitonin, calcium folinate, calcium levofolinate, capecitabine, capromab, carbomazepine, carboplatin, carboquon, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, dabrafenib, darolutamide, dasatinib, daunorubicin, decitabine, degarelix, denileukin-diftitox, denosumab, depreotide, deslorelin, dexrazoxane, dibrospidium chloride, dianhydrogalactitol, diclofenac, docetaxel, dolasetron, doxifluridine, doxorubicin, doxorubicin+estrone, dronabinol, durvalumab, edrecolomab, elliptinium acetate, endostatin, enocitabine, enzalutamide, epacadostat, epirubicin, epitiostanol, epoetin-alfa, epoetin-beta, epoetin-zeta, eptaplatin, eribulin, erlotinib, esomeprazole, estramustine, etoposide, ethylnyl oestradiol, everolimus, exemestane, fadrozole, fentanyl, fluoxymesterone, floxuridine, fludarabine, fluorouracil, flutamide, folic acid, formestane, fosaprepitant, fotemustine, fulvestrant, gadobutrol, gadoteridol, gadoteric acid meglumine salt, gadoversetamide, gadoxetic acid disodium salt (gd-EOB-DTPA disodium salt), gallium nitrate, ganirelix, gefitinib, gemcitabine, gemtuzumab, glucarpidase, glutoxim, goserelin, granisetron, granulocyte colony stimulating factor (G-CSF), granulocyte macrophage colony stimulating factor (GM-CSF), histamine dihydrochloride, histrelin, hydroxycarbamide, 1-125 seeds, ibandronic acid, ibritumomab-tiuxetan, ibrutinib, idarubicin, ifosfamide, imatinib, imiquimod, improsulfan, indisetron, incadronic acid, ingenol mebutate, interferon-alfa, interferon-beta, interferon-gamma, iobitridol, iobenguane (123I), iomeprol, ipilimumab, irinotecan, itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxin-sodium, lipegfilgrastim, lisuride, lobaplatin, lomustine, lonidamine, masoprocol, medroxyprogesteron, megestrol, melarsoprol, melphalan, mepitiostan, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotan, mitoxantrone, mogamulizumab, molgramostim, mopidamol, morphine hydrochloride, morphine sulfate, nabilone, nabiximols, nafarelin, naloxone+pentazocine, naltrexone, nartograstim, necitumumab, nedaplatin, nelarabine, neridronic acid, netupitant/palonosetrone, nivolumab, nivolumab, pentetreotide, nilotinib, nilutamide, nimorazole, nimotuzumab, nimustine, nintedanib, nitracrine, nivolumab, obinutuzumab, octreotide, ofatumumab, olaparib, olaratumab, omacetaxin mepesuccinate, omeprazole, ondansetron, orgotein, orilotimod, osimertinib, oxaliplatin, oxycodone, oxymetholone, ozogamicin, p53 gene therapy, paclitaxel, palbociclib, palifermine, palladium-103 seed, palonosetron, pamidronic acid, panitumumab, panobinostat, pantoprazole, pazopanib, pegaspargase, pembrolizumab, Peg-interferon alfa-2b, pembrolizumab, pemetrexed, pentostatin, peplomycin, perflubutane, perfosfamide, pertuzumab, picibanil, pilocarpine, pirarubicin, pixantron, plerixafor, plicamycin, poliglusam, polyoestradiol phosphate, polyvinylpyrrolidone+sodium hyaluronate, polysaccharide-K, pomalidomide, ponatinib, porfimer-sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxan, refametinib, regorafenib, risedronic acid, rhenium-186 etidronate, rituximab, rogaratinib, rolapitant, romidepsin, romurtid, roniciclib, samarium (153Sm) lexidronam, satumomab, secretin, siltuximab, sipuleucel-T, sizofiran, sobuzoxane, sodium glycididazole, sonidegib, sorafenib, stanozolol, streptozocin, sunitinib, talaporf in, talimogen laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, trametinib, tramadol, trastuzumab, treosulfan, tretinoin, trifluridine+tipiracil, trametinib, trilostane, triptorelin, trofosfamide, thrombopoietin, ubenimex, valrubicin, vandetanib, vapreotide, vatalanib, vemurafenib, vinblastine, vincristine, vindesine, vinflunine, vinorelbine, vismodegib, vorinostat, yttrium-90 glass microbeads, zinostatin, zinostatin stimalamer, zoledronic acid, zorubicin In addition, the compounds of the present invention can be combined, for example, with binders (e.g. antibodies) which, by way of example, can bind to the following targets: OX-40, CD137/4-1BB, DR3, IDO1/IDO2, LAG-3, CD40.

Since a non-cell-permeable toxophore metabolite of an antibody-drug conjugate (ADC) should have no damaging effect on the cells of the adaptive immune system, the invention furthermore provides the combination of an antibody-drug conjugate (ADC) according to the invention with a cancer immunotherapy for use in the treatment of cancer or tumours. The intrinsic mechanism of action of cytotoxic antibody-drug conjugates comprises the direct triggering of cell death of the tumour cells and thus the release of tumour antigens which may stimulate an immune response. Furthermore, there are indications that the KSP inhibitor toxophore class induces markers of immunogenic cell death (ICD) in vitro. Thus, the combination of the binder-drug conjugates (ADCs) of the present invention with one or more therapeutic approaches of cancer immunotherapy or with one or more active compounds, preferably antibodies, directed against a molecular target of cancer immunotherapy represents a preferred method for treating cancer or tumours. i) Examples of therapeutic approaches of cancer immunotherapy comprise immunomodulatory monoclonal antibodies and low-molecular weight substances directed against targets of cancer immunotherapy, vaccines, CAR T cells, bispecific T-cell-recruiting antibodies, oncolytic viruses, cell-based vaccination approaches. ii) Examples of selected targets of cancer immunotherapy suitable for immunemodulatory monoclonal antibodies comprise CTLA-4, PD-1/PDL-1, OX-40, CD137, DR3, IDO1, IDO2, TDO2, LAG-3, TIM-3 CD40, ICOS/ICOSL, TIGIT; GITR/GITRL, VISTA, CD70, CD27, HVEM/BTLA, CEACAM1, CEACAM6, ILDR2, CD73, CD47, B7H3, TLRs. Accordingly, combination of an antibody-drug conjugate (ADC) according to the invention with cancer immunotherapy could, on the one hand, render tumours with weak immunogenic properties more immunogenic and enhance the effectiveness of cancer immunotherapy, and furthermore unfold long-lasting therapeutic action.

In addition, the compounds according to the invention can also be used in combination with radiotherapy and/or surgical intervention.

Generally, the following aims can be pursued with the combination of compounds of the present invention with other cytostatically, cytotoxically or immunotherapeutically active agents:

improved efficacy in slowing the growth of a tumour, in reducing its size or even in completely eliminating it, compared with treatment with an individual active ingredient;

the possibility of using the chemotherapeutics used in a lower dosage than in the case of monotherapy;

the possibility of a more tolerable therapy with fewer side effects compared with individual administration;

the possibility of treatment of a broader spectrum of neoplastic disorders;

the achievement of a higher rate of response to the therapy;

a longer survival time of the patient compared with present-day standard therapy.

In addition, the compounds according to the invention can also be used in combination with radiotherapy and/or surgical intervention.

The present invention further provides medicaments which comprise at least one compound of the invention, typically together with one or more inert, non-toxic, pharmaceutically suitable excipients, and for the use thereof for the aforementioned purposes.

The compounds of the invention can act systemically and/or locally. For this purpose, they can be administered in a suitable manner, for example parenterally, possibly inhalatively or as implants or stents.

The compounds of the invention can be administered in administration forms suitable for these administration routes.

Parenteral administration can bypass an absorption step (for example intravenously, intraarterially, intracardially, intraspinally or intralumbally) or include an absorption (for example intramuscularly, subcutaneously, intracutaneously, percutaneously or intraperitoneally). Administration forms suitable for parenteral administration include preparations for injection and infusion in the form of solutions, suspensions, emulsions or lyophilizates. Preference is given to parenteral administration, especially intravenous administration.

In general, it has been found to be advantageous in the case of parenteral administration to administer amounts of about 0.1 to 20 mg/kg, preferably about 0.3 to 7 mg/kg, of body weight to achieve effective results.

It may nevertheless be necessary in some cases to deviate from the stated amounts, and specifically as a function of body weight, route of administration, individual response to the active ingredient, nature of the preparation and time at which or interval over which administration takes place. Thus in some cases it may be sufficient to manage with less than the abovementioned minimum amount, while in other cases the upper limit mentioned must be exceeded. In the case of administration of greater amounts, it may be advisable to divide them into several individual doses over the day.

EXAMPLES

The examples which follow illustrate the invention. The invention is not restricted to the examples.

Unless stated otherwise, the percentages in the tests and examples which follow are percentages by weight; parts are parts by weight. Solvent ratios, dilution ratios and concentration data for the liquid/liquid solutions are based in each case on volume.

If no information with respect to a temperature at which the reaction is carried out is given in the experimental descriptions, room temperature is to be assumed.

Synthesis Routes:

By way of example for the working examples, the following schemes show illustrative synthesis routes leading to the working examples: Both the synthesis sequence and the protective group strategy can be varied on the route to the target compounds.

Scheme 1: Synthesis of intermediates

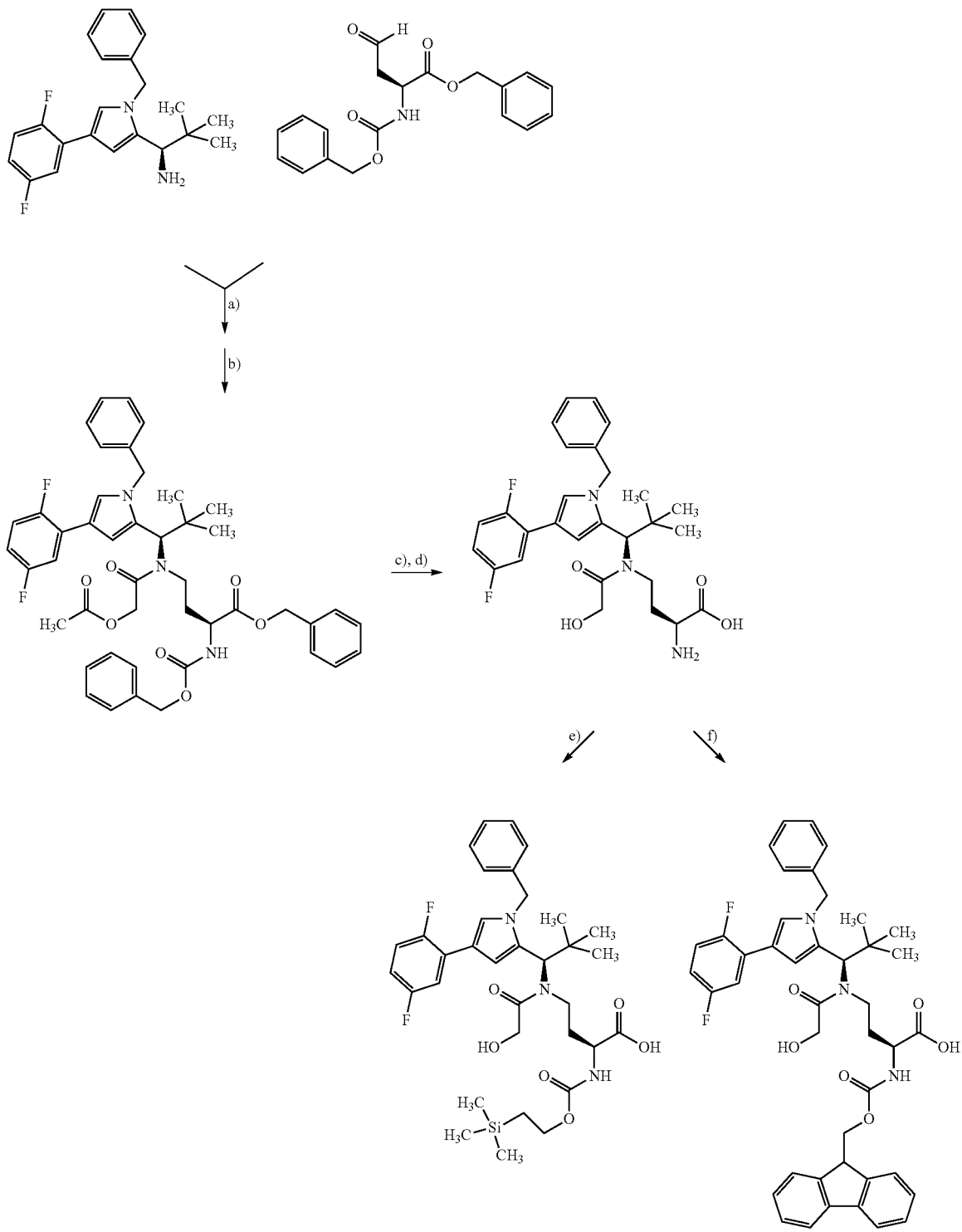

[a]: for example sodium triacetoxy borohydride, acetic acid, DCM, RT; b) for example acetoxyacetyl chloride, NEt3, DCM, RT; c) for example LiOH, THF/water, RT; d) for example H₂, Pd—C, EtOH, RT; e) for example Teoc-OSu, NEt3, dioxane, RT; f) for example Fmoc-Cl, diisopropyl-ethylamine, dioxane/water 2:1, RT]
Scheme 2: Synthesis of cysteine-linked ADCs via ring-opened succinimides
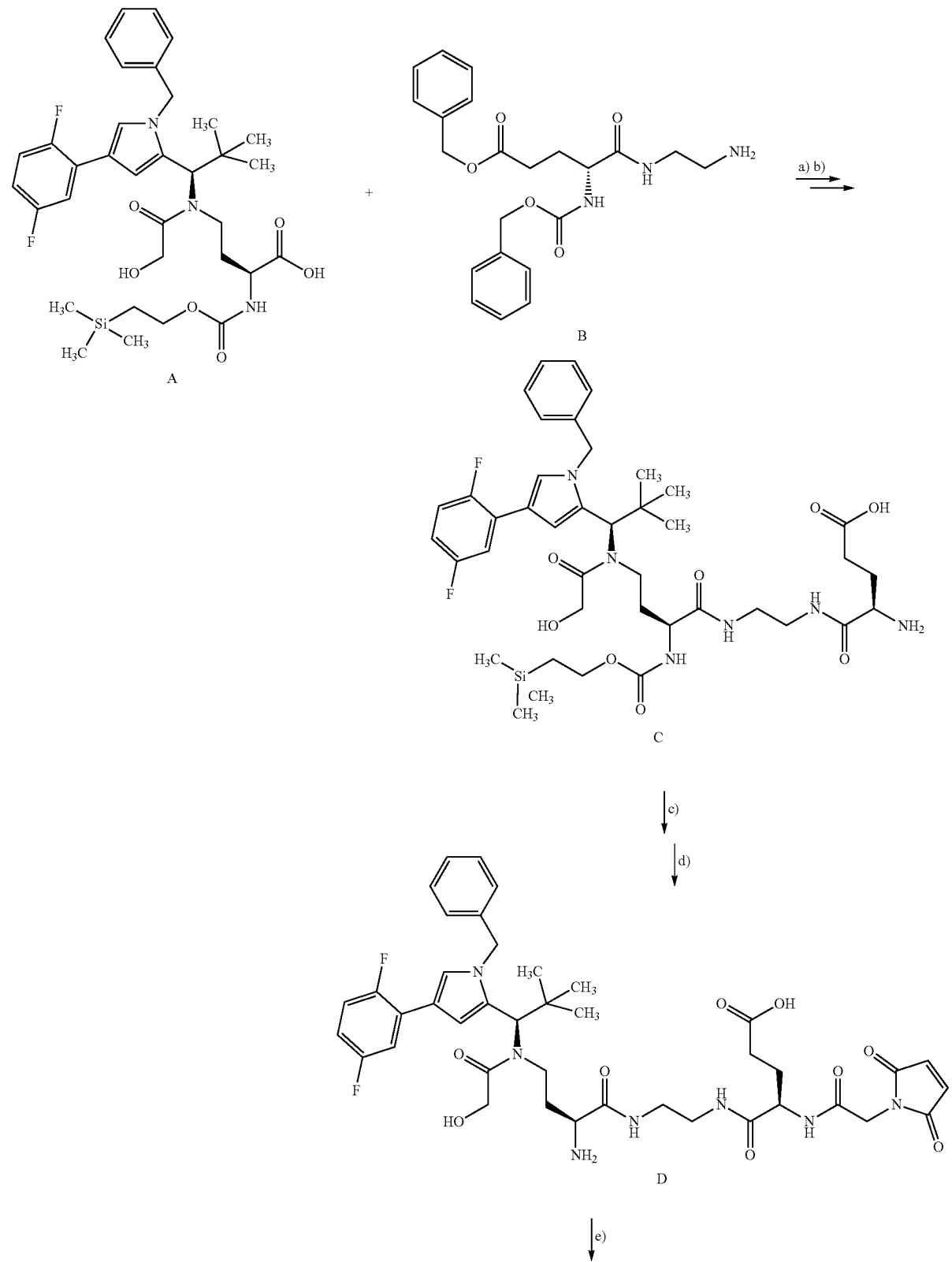

-continued

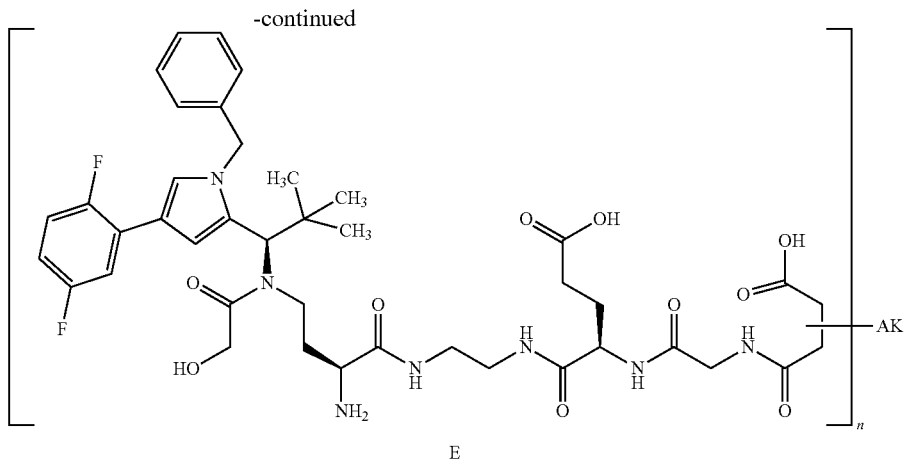

E

[a]: HATU, DMF, N,N-diisopropylethylamine, RT; b): H₂, 10% Pd—C, methanol, RT c): 1,1'-[(1,5-dioxopyrrolidin-1-yl)oxy]-2-oxoethyl}-1H-pyrrole-2,5-dione, N, N-diisopropylethylamine, DMF, stirring at RT; d) 2,2,2-trifluoroethanol, 4-8 equivalents of zinc chloride, 2-6 h at 50° C.; e) AK dissolved in PBS, under argon addition of 3-4 equivalents of TCEP in PBS buffer and about 30 min stirring at RT, then addition of 5-10 equivalents of compound D dissolved in DMSO, about 90 min of stirring at RT, then rebuffering to pH 8 by means of PD 10 columns equilibrated with PBS buffer (pH 8) (Sephadex® G-25, GE Healthcare), then stirring at RT overnight, then optionally purification by means of PD 10 columns equilibrated with PBS buffer (pH 7.2) (Sephadex® G-25, GE Healthcare) and subsequent concentration by means of ultracentrifugation and setting of the concentration desired with PBS buffer (pH 7.2)]. In the case of in vivo batches, this is optionally followed by sterile filtration.

A. Examples

Abbreviations and Acronyms

ABCB1 ATP-binding cassette sub-family B member 1 (synonym for P-gp and MDR1)
abs. absolute
Ac acetyl
ACN acetonitrile
aq. aqueous, aqueous solution
ATP adenosine triphosphate
BCRP breast cancer resistance protein, an efflux transporter
BEP 2-bromo-1-ethylpyridinium tetrafluoroborate
Boc tert-butoxycarbonyl
br. broad (in NMR)
Ex. Example
C concentration
ca. circa, about
CI chemical ionization (in MS)
d doublet (in NMR)
d day(s)
DAR drug-to-antibody ratio
TLC thin layer chromatography
DCI direct chemical ionization (in MS)
DCM dichloromethane
dd doublet of doublets (in NMR)
DMAP 4-N,N-dimethylaminopyridine
DME 1,2-dimethoxyethane
DMEM Dulbecco's Modified Eagle Medium (standardized nutrient medium for cell culture)
DMF N,N-dimethylformamide
DMSO dimethyl sulfoxide
D/P dye (fluorescent dye)/protein ratio
DPBS, D-PBS, Dulbecco's phosphate-buffered salt solution
DSMZ Deutsche Sammlung von Mikroorganismen and Zellkulturen (German Collection of Microorganisms and Cell Cultures)
PBS PBS=DPBS=D-PBS, pH 7.4, from Sigma, No D8537
 Composition:
 0.2 g KCl
 0.2 g $KH_2PO_4$ (anhyd)
 8.0 g NaCl
 1.15 g $Na_2HPO_4$ (anhyd)
 made up ad 1 l with $H_2O$
dt doublet of triplets (in NMR)
DTT DL-dithiothreitol
EDC N'-(3-dimethylaminopropyl)-N-ethylcarbodiimide hydrochloride
EGFR epidermal growth factor receptor
EI electron impact ionization (in MS)
ELISA enzyme-linked immunosorbent assay
eq. equivalent(s)
ESI electrospray ionization (in MS)
ESI-MicroTofq ESI-MicroTofq (name of the mass spectrometer with Tof=time of flight and q=quadrupole)
FCS foetal calf serum
Fmoc (9H-fluoren-9-ylmethoxy)carbonyl
sat. saturated
GTP guanosine-5'-triphosphate
H hour(s)
HATU O-(7-azabenzotriazol-1-yl)-N,N,N',N'-tetramethyluronium hexafluorophosphate
HEPES 4-(2-hydroxyethyl)piperazine-1-ethanesulfonic acid
HOAc acetic acid
HOAt 1-hydroxy-7-azabenzotriazole
HOBt 1-hydroxy-1H-benzotriazole hydrate
HOSu N-hydroxysuccinimide
HPLC high-pressure, high-performance liquid chromatography
$IC_{50}$ half-maximal inhibitory concentration
i.m. intramuscularly, administration into the muscle
i.v. intravenously, administration into the vein
KPL-4 human tumour cell line
conc. concentrated LC-MS liquid chromatography-coupled mass spectrometry
LLC-PK1 cells Lewis lung carcinoma pork kidney cell line
L-MDR human MDR1 transfected LLC-PK1 cells
M multiplet (in NMR)
MDR1 Multidrug resistance protein 1
MeCN acetonitrile
Me methyl
min minute(s)
MOLM-13 human tumour cell line
MS mass spectrometry
MTT 3-(4,5-dimethylthiazol-2-yl)-2,5-diphenyl-2H-tetrazolium bromide
MV-4-11 human tumour cell line
NCI-H292 human tumour cell line
NMM N-methylmorpholine
NMP N-methyl-2-pyrrolidinone
NMR nuclear magnetic resonance spectrometry
NMRI mouse strain originating from the Naval Medical Research Institute (NMRI)
Nude mice experimental animals
NSCLC non small cell lung cancer
PBS phosphate-buffered salt solution
Pd/C palladium on activated charcoal
P-gp P-glycoprotein, a transporter protein
PNGaseF enzyme for cleaving sugar
quant. quantitative (in yield)
quart quartet (in NMR)
quint quintet (in NMR)
Rec-1 human tumour cell line
$R_f$ retention index (in TLC)
RT room temperature
$R_t$ retention time (in HPLC)
s singlet (in NMR)
s.c. subcutaneously, administration under the skin
SCID mice test mice with severe combined immunodeficiency
SK-HEP-1 human tumour cell line
triplet (in NMR)
TBAF tetra-n-butylammonium fluoride
TEMPO (2,2,6,6-tetramethylpiperidin-1-yl)oxyl
Teoc trimethylsilylethoxycarbonyl
Teoc-OSu 1-({[2-(trimethylsilyl)ethoxy]carbonyl}oxy)pyrrolidine-2,5-dione
tert tertiary
TFA trifluoroacetic acid
THF tetrahydrofuran
T3P® 2,4,6-tripropyl-1,3,5,2,4,6-trioxatriphosphinane 2,4,6-trioxide
UV ultraviolet spectrometry
v/v volume to volume ratio (of a solution)
Z benzyloxycarbonyl
HPLC and LC-MS Methods:
Method 1 (LC-MS):
  Instrument: Waters ACQUITY SQD UPLC System; column: Waters Acquity UPLC HSS T3 1.8µ 50×1 mm; mobile phase A: 1 l of water+0.25 ml of 99% strength formic acid; mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 208-400 nm.
Method 2 (LC-MS):
  MS instrument type: Waters Synapt G2S; UPLC instrument type: Waters Acquity I-CLASS; column: Waters, BEH300, 2.1×150 mm, C18 1.7 µm; mobile phase A: 1 l of water+0.01% formic acid; mobile phase B: 1 l of acetonitrile+0.01% formic acid; gradient: 0.0 min 2% B→1.5 min 2% B→8.5 min 95% B→10.0 min 95% B; oven: 50° C.; flow rate: 0.50 ml/min; UV detection: 220 nm
Method 3 (LC-MS):
  MS instrument: Waters (Micromass) QM; HPLC instrument: Agilent 1100 series; column: Agilent ZORBAX Extend-C18 3.0×50 mm 3.5 micron; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm
Method 4 (LC-MS):
  MS instrument type: Waters Synapt G2S; UPLC instrument type: Waters Acquity I-CLASS; column: Waters, HSST3, 2.1×50 mm, C18 1.8 µm; mobile phase A: 1 l of water+0.01% formic acid; mobile phase B: 1 l of acetonitrile+0.01% formic acid; gradient: 0.0 min 10% B→0.3 min 10% B→1.7 min 95% B→2.5 min 95% B; oven: 50° C.; flow rate: 1.20 ml/min; UV detection: 210 nm
Method 5 (LC-MS):
  Instrument: Waters ACQUITY SQD UPLC System; column: Waters Acquity UPLC HSS T3 1.8µ 50×1 mm; mobile phase A: 1 l of water+0.25 ml of 99% strength formic acid; mobile phase B: 1 l of acetonitrile+0.25 ml of 99% strength formic acid; gradient: 0.0 min 95% A→6.0 min 5% A→7.5 min 5% A; oven: 50° C.; flow rate: 0.35 ml/min; UV detection: 210-400 nm.
Method 6 (LC-MS):
  Instrument: Micromass Quattro Premier with Waters UPLC Acquity; column: Thermo Hypersil GOLD 1.9µ, 50×1 mm; mobile phase A: 1 l of water+0.5 ml of 50% strength formic acid; mobile phase B: 1 l of acetonitrile+0.5 ml of 50% strength formic acid; gradient: 0.0 min 97% A→0.5 min 97% A→3.2 min 5% A→4.0 min 5% A oven: 50° C.; flow rate: 0.3 ml/min; UV detection: 210 nm.
Method 7 (LC-MS):
  Instrument: Agilent MS Quad 6150; HPLC: Agilent 1290; column: Waters Acquity UPLC HSS T3 1.8µ 50×2.1 mm; mobile phase A: 1 l of water+0.25 ml of 99% strength formic acid; mobile phase B: 1 l of acetonitrile+0.25 ml of 99% strength formic acid; gradient: 0.0 min 90% A→0.3 min 90% A→1.7 min 5% A→3.0 min 5% A oven: 50° C.; flow rate: 1.20 ml/min; UV detection: 205-305 nm.
Method 8 (LC-MS):
  MS instrument type: Waters Synapt G2S; UPLC instrument type: Waters Acquity !-CLASS; column: Waters, HSST3, 2.1×50 mm, C18 1.8 µm; mobile phase A: 1 l of water+0.01% formic acid; mobile phase B: 1 l of acetonitrile+0.01% formic acid; gradient: 0.0 min 2% B→2.0 min 2% B→13.0 min 90% B→15.0 min 90% B; oven: 50° C.; flow rate: 1.20 ml/min; UV detection: 210 nm.
Method 9: (LC-MS prep. purification method)
  MS instrument: Waters, HPLC instrument: Waters (column Waters X-Bridge C18, 19 mm×50 mm, 5 µm, eluent A: water+0.05% ammonia, mobile phase B: acetonitrile (ULC) with gradient; flow rate: 40 ml/min; UV detection: DAD; 210-400 nm).

or

MS instrument: Waters, HPLC instrument: Waters (column Phenomenex Luna 5μ C18(2) 100A, AXIA Tech. 50×21.2 mm, eluent A: water+0.05% formic acid, eluent B: acetonitrile (ULC) with gradient; flow rate: 40 ml/min; UV detection: DAD; 210-400 nm).

Method 10: (LC-MS Analysis Method)

MS instrument: Waters SQD; HPLC instrument: Waters UPLC; column: Zorbax SB-Aq (Agilent), 50 mm×2.1 mm, 1.8 μm; mobile phase A: water+0.025% formic acid, eluent B: acetonitrile (ULC)+0.025% formic acid; gradient: 0.0 min 98% A—0.9 min 25% A—1.0 min 5% A—1.4 min 5% A—1.41 min 98% A—1.5 min 98% A; oven: 40° C.; flow rate: 0,600 ml/min; UV detection: DAD; 210 nm.

Method 11 (HPLC):

Instrument: HP1100 Series, column: Merck Chromolith SpeedROD RP-18e, 50-4.6 mm, Cat. No. 1.51450.0001, precolumn Chromolith Guard Cartridge Kit, RP-18e, 5-4.6 mm, Cat. No. 1.51470.0001; gradient: flow rate 5 ml/min; injection volume 5 μl; solvent A: HClO4 (70%) in water (4 ml/1), solvent B: acetonitrile start 20% B, 0.50 min 20% B, 3.00 min 90% B, 3.50 min 90% B, 3.51 min 20% B, 4.00 min 20% B, column temperature: 40° C., wavelength: 210 nm Method 12 (LC-MS):

MS instrument type: Thermo Scientific FT-MS; instrument type UHPLC+: Thermo Scientific UltiMate 3000; column: Waters, HSST3, 2.1×75 mm, C18 1.8 μm; mobile phase A: 1 l of water+0.01% formic acid; mobile phase B: 1 l of acetonitrile+0.01% formic acid; gradient: 0.0 min 10% B→2.5 min 95% B→3.5 min 95% B; oven: 50° C.; flow rate: 0.90 ml/min; UV detection: 210 nm/optimum integration path 210-300 nm Method 13: (LC-MS):

MS instrument: Waters (Micromass) Quattro Micro; instrument Waters UPLC Acquity; column: Waters BEH C18 1.7μ 50×2.1 mm; mobile phase A: 1 l of water+0.01 mol of ammonium formate, mobile phase B: 1 l of acetonitrile; gradient: 0.0 min 95% A→0.1 min 95% A→2.0 min 15% A→2.5 min 15% A→2.51 min 10% A→3.0 min 10% A; oven: 40° C.; flow rate: 0.5 ml/min; UV detection: 210 nm.

Method 14: (LC-MS):

MS instrument type: ThermoFisherScientific LTQ-Orbitrap-XL; HPLC instrument type: Agilent 1200SL; column: Agilent, POROSHELL 120, 3×150 mm, SB—C18 2.7 μm; mobile phase A: 1 l of water+0.1% trifluoroacetic acid; mobile phase B: 1 l of acetonitrile+0.1% trifluoroacetic acid; gradient: 0.0 min 2% B→0.3 min 2% B→5.0 min 95% B 10.0 min 95% B; oven: 40° C.; flow rate: 0.75 ml/min; UV detection: 210 nm All reactants or reagents whose preparation is not described explicitly hereinafter were purchased commercially from generally accessible sources. For all other reactants or reagents whose preparation likewise is not described hereinafter and which were not commercially obtainable or were obtained from sources which are not generally accessible, a reference is given to the published literature in which their preparation is described.

Starting Compounds and Intermediates

Intermediate C52

(1R)-1-[1-Benzyl-4-(2,5-difluorophenyl)-1H-pyrol-2-yl]-2,2-dimethylpropan-1-amine

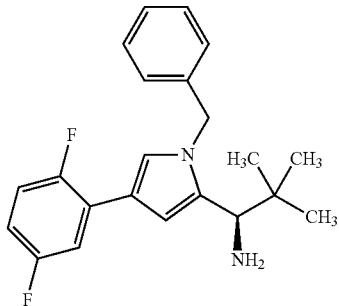 [SMILES: CC(C)(C)[C@@H](N)c1cc(-c2cc(F)ccc2F)cn1Cc1ccccc1]

10.00 g (49.01 mmol) of methyl 4-bromo-1H-pyrrole-2-carboxylate were initially charged in 100.0 ml of DMF, and 20.76 g (63.72 mmol) of caesium carbonate and 9.22 g (53.91 mmol) of benzyl bromide were added. The reaction mixture was stirred at RT overnight. The reaction mixture was partitioned between water and ethyl acetate and the aqueous phase was extracted with ethyl acetate. The combined organic phases were dried over magnesium sulfate and the solvent was evaporated under reduced pressure. The reaction was repeated with 90.0 g of methyl 4-bromo-1H-pyrrole-2-carboxylate.

The two combined reactions were purified by preparative RP-HPLC (column: Daiso 300×100; 10μ, flow rate: 250 ml/min, MeCN/water). The solvents were evaporated under reduced pressure and the residue was dried under high vacuum. This gave 125.15 g (87% of theory) of the compound methyl 1-benzyl-4-bromo-1H-pyrrole-2-carboxylate.

LC-MS (Method 1): $R_t$=1.18 min; MS (ESIpos): m/z=295 [M+H]$^+$.

Under argon, 4.80 g (16.32 mmol) of methyl 1-benzyl-4-bromo-1H-pyrrole-2-carboxylate were initially charged in DMF, and 3.61 g (22.85 mmol) of (2,5-difluorophenyl) boronic acid, 19.20 ml of saturated sodium carbonate solution and 1.33 g (1.63 mmol) of [1,1'-bis(diphenylphosphino) ferrocene]-dichloropalladium(II):dichloromethane were added. The reaction mixture was stirred at 85° C. overnight. The reaction mixture was filtered through Celite and the filter cake was washed with ethyl acetate. The organic phase was extracted with water and then washed with saturated NaCl solution. The organic phase was dried over magnesium sulfate and the solvent was evaporated under reduced pressure. The residue was purified on silica gel (mobile phase: cyclohexane/ethyl acetate 100:3). The solvents were evaporated under reduced pressure and the residue was dried under high vacuum. This gave 3.60 g (67% of theory) of the compound methyl 1-benzyl-4-(2,5-difluorophenyl)-1H-pyrrole-2-carboxylate.

LC-MS (Method 7): $R_t$=1.59 min; MS (ESIpos): m/z=328 [M+H]$^+$.

3.60 g (11.00 mmol) of methyl 1-benzyl-4-(2,5-difluorophenyl)-1H-pyrrole-2-carboxylate were initially charged in 90.0 ml of THF, and 1.04 g (27.50 mmol) of lithium aluminium hydride (2.4 M in THF) were added at 0° C. The reaction mixture was stirred at 0° C. for 30 minutes. Saturated potassium sodium tartrate solution was added at 0° C.

and the reaction mixture was admixed with ethyl acetate. The organic phase was extracted three times with sat. potassium sodium tartrate solution. The organic phase was washed once with saturated NaCl solution and dried over magnesium sulfate. The solvent was evaporated under reduced pressure and the residue was dissolved in 30.0 ml of dichloromethane. 3.38 g (32.99 mmol) of manganese(IV) oxide were added, and the mixture was stirred at RT for 48 h. Another 2.20 g (21.47 mmol) of manganese(IV) oxide were added, and the mixture was stirred at RT overnight. The reaction mixture was filtered through Celite and the filter cake was washed with dichloromethane. The solvent was evaporated under reduced pressure and the residue 2.80 g of (1-benzyl-4-(2,5-difluorophenyl)-1H-pyrrole-2-carbaldehyde) was used without further purification in the next step of the synthesis.

LC-MS (Method 7): $R_t$=1.48 min; MS (ESIpos): m/z=298 $[M+H]^+$.

28.21 g (94.88 mmol) of 1-benzyl-4-(2,5-difluorophenyl)-1H-pyrrole-2-carbaldehyde together with 23.00 g (189.77 mmol) of (R)-2-methylpropane-2-sulfinamide were initially charged in 403.0 ml of absolute THF, and 67.42 g (237.21 mmol) of titanium(IV) isopropoxide were added and the mixture was stirred at RT overnight. 500 ml of saturated NaCl solution and 1000.0 ml of ethyl acetate were added, and the mixture was stirred at RT for 1 h. The mixture was filtered through kieselguhr and the filtrate was washed twice with saturated NaCl solution. The organic phase was dried over magnesium sulfate, the solvent was evaporated under reduced pressure and the residue was purified using Biotage Isolera (silica gel, column 1500+340 g SNAP, flow rate 200 ml/min, ethyl acetate/cyclohexane 1:10).

LC-MS (Method 7): $R_t$=1.63 min; MS (ESIpos): m/z=401 $[M+H]^+$.

25.00 g (62.42 mmol) of (R)—N-{(E/Z)-[1-benzyl-4-(2,5-difluorophenyl)-1H-pyrrol-2-yl]-methylene}-2-methyl-propane-2-sulfinamide were initially charged in absolute THF under argon and cooled to −78° C. 12.00 g (187.27 mmol) of tert-butyllithium (1.7 M solution in pentane) were then added at −78° C. and the mixture was stirred at this temperature for 3 h. At −78° C., 71.4 ml of methanol and 214.3 ml of saturated ammonium chloride solution were then added successively and the reaction mixture was allowed to warm to RT and stirred at RT for 1 h. The mixture was diluted with ethyl acetate and washed with water. The organic phase was dried over magnesium sulfate and the solvent was evaporated under reduced pressure. The residue (R)—N-{(1R)-1-[1-benzyl-4-(2,5-difluorophenyl)-1H-pyrrol-2-yl]-2,2-dimethylpropyl}-2-methylpropane-2-sulfinamide was used without further purification in the next step of the synthesis.

LC-MS (Method 6): $R_t$=2.97 min; MS (ESIpos): m/z=459 $[M+H]^+$.

28.00 g (61.05 mmol) of (R)—N-{(1R)-1-[1-benzyl-4-(2,5-difluorophenyl)-1H-pyrrol-2-yl]-2,2-dimethylpropyl}-2-methylpropane-2-sulfinamide were initially charged in 186.7 ml of 1,4-dioxane, and 45.8 ml of HCl in 1,4-dioxane solution (4.0 M) were then added. The reaction mixture was stirred at RT for 2 h and the solvent was evaporated under reduced pressure. The residue was purified by preparative HPLC (column: Kinetix 100×30; flow rate: 60 ml/min, MeCN/water). The acetonitrile was evaporated under reduced pressure and dichloromethane was added to the aqueous residue. The organic phase was washed with sodium bicarbonate solution and dried over magnesium sulfate. The solvent was evaporated under reduced pressure and the residue was dried under high vacuum. This gave 16.2 g (75% of theory) of the title compound.

LC-MS (Method 6): $R_t$=2.10 min; MS (ESIpos): m/z=338 $[M-NH_2]^+$, 709 $[2M+H]^+$.

$^1$H-NMR (400 MHz, DMSO-$d_6$): δ [ppm]=0.87 (s, 9H), 1.53 (s, 2H), 3.59 (s, 1H), 5.24 (d, 2H), 6.56 (s, 1H), 6.94 (m, 1H), 7.10 (d, 2H), 7.20 (m, 1H), 7.26 (m, 2H), 7.34 (m, 2H), 7.46 (m, 1H).

Intermediate C58

(2S)-4-[{(1R)-1-[1-Benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoic acid

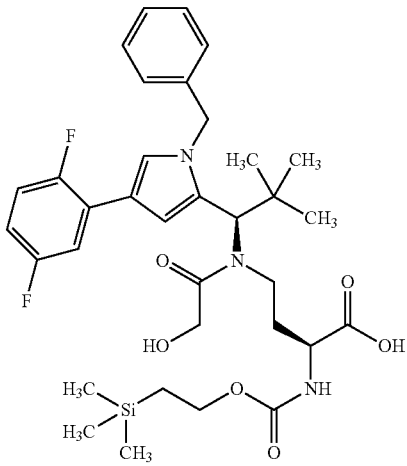 [SMILES: CC(C)(C)[C@H](c1cc(-c2cc(F)ccc2F)cn1Cc1ccccc1)N(CC[C@H](NC(=O)OCC[Si](C)(C)C)C(=O)O)C(=O)CO]

4.3 g (12.2 mmol) of Intermediate C52 were dissolved in 525 ml of DCM, and 3.63 g (17.12 mmol) of sodium triacetoxyborohydride and 8.4 ml of acetic acid were added. After 5 min of stirring at RT, 8.99 g (24.5 mmol) of Intermediate L57 dissolved in 175 ml of DCM were added and the reaction was stirred at RT for a further 45 min. The reaction was then diluted with 300 ml of DCM and washed twice with 100 ml of sodium bicarbonate solution and once with saturated NaCl solution. The organic phase was dried over magnesium sulfate, the solvent was evaporated under reduced pressure and the residue was dried under high vacuum. The residue was then purified by preparative RP-HPLC (column: Chromatorex C18). After combination of the appropriate fractions, the solvent was evaporated under reduced pressure and the residue was dried under high vacuum. This gave 4.6 g (61% of theory) of methyl (2S)-4-({(1R)-1-[1-benzyl-4-(2,5-difluorophenyl)-1H-pyrrol-2-yl]-2,2-dimethylpropyl}amino)-2-({[2-(trimethylsilyl)ethoxy]carbonyl}amino)butanoate.

LC-MS (Method 12): $R_t$=1.97 min; MS (ESIpos): m/z=614 $(M+H)^+$.

2.06 g (3.36 mmol) of this intermediate were initially charged in 76 ml of DCM and acylated with 0.81 ml (7.17 mmol) of 2-chloro-2-oxoethyl acetate in the presence of 2.1 ml of triethylamine. After 20 h of stirring at RT, 0.36 ml of 2-chlor-2-oxoethyl acetate and 0.94 ml of triethylamine were added and the reaction was stirred at RT for a further 15 min. The mixture was then diluted with 500 ml of ethyl acetate and extracted successively twice with 300 ml of 5% citric acid, twice with 300 ml of saturated sodium hydrogencarbonate solution and once with 100 ml of saturated sodium chloride solution and then dried over magnesium sulfate and concentrated. Drying under high vacuum gave 2.17 g (79% of theory) of the protected intermediate.

LC-MS (Method 1): $R_t$=1.48 min; MS (ESIpos): m/z=714 $(M+H)^+$.

2.17 mg (2.64 mmol) of this intermediate were dissolved in 54 ml of THF and 27 ml of water, and 26 ml of a 2-molar lithium hydroxide solution were added. The mixture was stirred at RT for 30 min and then adjusted to a pH between 3 and 4 using 1.4 ml of TFA. The mixture was concentrated under reduced pressure. Once most of the THF had been distilled off, the aqueous solution was extracted twice with DCM and then concentrated to dryness under reduced pressure. The residue was purified by preparative HPLC (column: Chromatorex C18). After combination of the appropriate fractions, the solvent was evaporated under reduced pressure and the residue was lyophilized from acetonitrile/water. This gave 1.1 g (63% of theory) of the title compound.

LC-MS (Method 1): $R_t$=1.34 min; MS (ESIpos): m/z=656 $(M-H)^-$.

$^1$H-NMR (400 MHz, DMSO-$d_6$): δ [ppm]=0.03 (s, 9H), 0.58 (m, 1H), 0.74-0.92 (m, 11H), 1.40 (m, 1H), 3.3 (m, 2H), 3.7 (m, 1H), 3.8-4.0 (m, 2H), 4.15 (q, 2H), 4.9 and 5.2 (2d, 2H), 5.61 (s, 1H), 6.94 (m, 2H), 7.13-7.38 (m, 7H), 7.48 (s, 1H), 7.60 (m, 1H), 12.35 (s, 1H).

Intermediate C66

2-(Trimethylsilyl)ethyl [(2S)-4-[{(1R)-1-[1-benzyl-4-(2,5-difluorophenyl)-1H-pyrrol-2-yl]-2,2-dimethylpropyl}(glycoloyl)amino]-1-{[2-(glycylamino)ethyl]amino}-1-oxobutan-2-yl]-carbamate

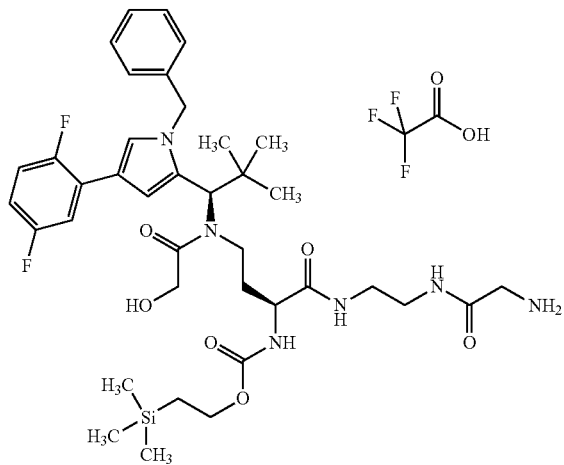 [SMILES: CC(C)(C)[C@H](c1cc(-c2cc(F)ccc2F)cn1Cc1ccccc1)N(CC[C@H](NC(=O)OCC[Si](C)(C)C)C(=O)NCCNC(=O)CN)C(=O)CO ; O=C(O)C(F)(F)F]

First, trifluoroacetic acid benzyl {2-[(2-aminoethyl) amino]-2-oxoethyl}carbamate was prepared from N-[(benzyloxy)carbonyl]glycine and tert-butyl (2-aminoethyl)carbamate by conventional methods of peptide chemistry (HATU coupling and Boc cleavage).

13 mg (0.036 mmol) of this intermediate and 25 mg (0.033 mmol) of intermediate C58 were taken up in 3 mL of DMF, and 19 mg (0.05 mmol) of HATU and 17 μl of N,N-diisopropylethylamine were added. After 10 min of stirring at RT, the mixture was concentrated and the residue was purified by preparative HPLC. This gave 17.8 mg (60% of theory) of the intermediate.

LC-MS (Method 1): $R_t$=1.36 min; MS (ESIpos): m/z=891 $(M+H)^+$.

17 mg (0.019 mmol) of this intermediate were dissolved in 10 ml of ethanol, palladium on carbon (10%) was added and the mixture was hydrogenated at RT using hydrogen under standard pressure for 2 h. The catalyst was filtered off, the solvents were evaporated under reduced pressure and the residue was dried under high vacuum. This gave 9 mg (62% of theory) of the title compound.

LC-MS (Method 1): $R_t$=1.03 min; MS (ESIpos): m/z=757 $(M+H)^+$.

Intermediate C118 tert-Butyl N-[(8S)-8-{2-[{(1R)-1-[1-benzyl-4-(2,5-difluorophenyl)-1H-pyrrol-2-yl]-2,2-dimethylpropyl}(glycoloyl)amino]ethyl}-2,2-dimethyl-6,9-dioxo-5-oxa-7,10-diaza-2-siladodecan-12-yl]-D-alpha-glutaminate

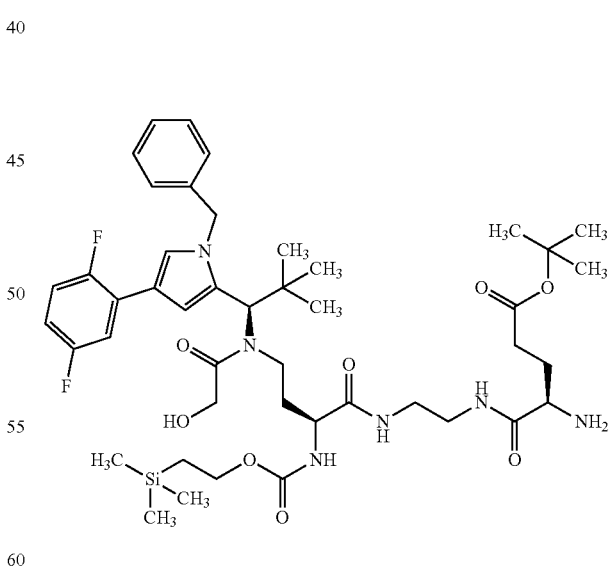

The title compound was prepared by conventional methods of peptide chemistry by coupling intermediate L119 and intermediate C58 in the presence of HATU and subsequent hydrogenolytical cleavage of the Z protective group.

LC-MS (Method 1): $R_t$=1.05 min; MS (ESIpos): m/z=885 $(M+H)^+$.

Intermediate C119 tert-Butyl glycyl-N-[(8S)-8-{2-[{(1R)-1-[1-benzyl-4-(2,5-difluorophenyl)-1H-pyrrol-2-yl]-2,2-dim ethylpropyl}(glycoloyl)amino]ethyl}-2,2-dimethyl-6,9-dioxo-5-oxa-7,10-diaza-2-siladodecan-12-yl]D-alpha-glutaminate

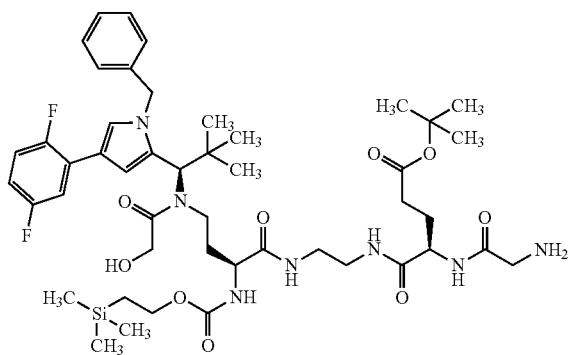 [SMILES: CC(C)(C)OC(=O)CC[C@@H](NC(=O)CN)C(=O)NCCNC(=O)[C@H](CCN(C(=O)CO)[C@@H](c1cc(-c2cc(F)ccc2F)cn1Cc1ccccc1)C(C)(C)C)NC(=O)OCC[Si](C)(C)C]

Intermediate C119 was prepared by conventional methods of peptide chemistry by coupling 2,5-dioxopyrrolidin-1-yl N-[(benzyloxy)carbonyl]glycinate and intermediate C118 in the presence of HATU and subsequent removal of the Z protective group by hydrogenation over 10% palladium on activated carbon in methanol/dichloromethane at RT under hydrogen standard pressure.

LC-MS (Method 1): $R_t$=1.03 min; MS (ESIpos): m/z=942 (M+H)$^+$.

Intermediate L1

Trifluoroacetic acid N-(2-aminoethyl)-2-(2,5-dioxo-2,5-dihydro-1H-pyrrol-1-yl)acetamide

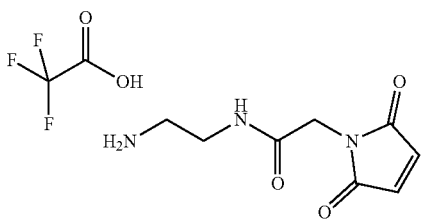

The title compound was prepared by conventional methods of peptide chemistry from commercial (2,5-dioxo-2,5-dihydro-1H-pyrrol-1-yl)acetic acid and tert-butyl (2-aminoethyl) carbamate.

LC-MS (Method 1): $R_t$=0.17 min; MS (ESIpos): m/z=198 (M+H)$^+$.

Intermediate L57

Methyl (2S)-4-oxo-2-({[2-(trimethylsilyl)ethoxy]carbonyl}amino)butanoate

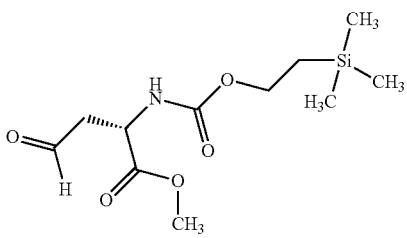 [SMILES: COC(=O)[C@H](CC=O)NC(=O)OCC[Si](C)(C)C]

500.0 mg (2.72 mmol) of methyl L-asparaginate hydrochloride and 706.3 mg (2.72 mmol) of 2-(trimethylsilyl)ethyl 2,5-dioxopyrrolidine-1-carboxylate were initially charged in 5.0 ml of 1,4-dioxane, and 826.8 mg (8.17 mmol) of triethylamine were added. The reaction mixture was stirred at RT overnight. The reaction mixture was purified directly by preparative RP-HPLC (column: Reprosil 250× 40; 10μ, flow rate 50 ml/min, MeCN/water, 0.1% TFA). The solvents were then evaporated under reduced pressure and the residue was dried under high vacuum. This gave 583.9 mg (74% of theory) of the compound (3S)-4-methoxy-4-oxo-3-({[2-(trimethylsilyl)ethoxy]carbonyl}amino)butanoic acid. LC-MS (Method 1): $R_t$=0.89 min; MS (ESIneg): m/z=290 (M–H)$^-$.

592.9 mg of (3S)-4-methoxy-4-oxo-3-({[2-(trimethylsilyl)ethoxy]carbonyl}amino)butanoic acid were initially charged in 10.0 ml of 1,2-dimethoxyethane, the mixture was cooled to –15° C. and 205.8 mg (2.04 mmol) of 4-methylmorpholine and 277.9 mg (2.04 mmol) of isobutyl chloroformate were added. The precipitate was filtered off with suction after 15 min and twice with in each case 10.0 ml of 1,2-dimethoxyethane. The filtrate was cooled to –10° C., and 115.5 mg (3.05 mmol) of sodium borohydride dissolved in 10 ml of water were added with vigorous stirring. The phases were separated and the organic phase was washed once each with saturated sodium hydrogencarbonate solution and saturated NaCl solution. The organic phase was dried over magnesium sulfate, the solvent was evaporated under reduced pressure and the residue was dried under high vacuum. This gave 515.9 mg (91% of theory) of the compound methyl N-{[2-(trimethylsilyl)ethoxy]carbonyl}-L-homoserinate.

LC-MS (Method 1): $R_t$=0.87 min; MS (ESIpos): m/z=278 (M+H)$^+$.

554.9 mg (2.00 mmol) of methyl N-{[2-(trimethylsilyl)ethoxy]carbonyl}-L-homoserinate were initially charged in 30.0 ml of dichloromethane, and 1.27 g (3.0 mmol) of Dess-Martin periodinane and 474.7 mg (6.00 mmol) of pyridine were added. The mixture was stirred at RT overnight. After 4 h, the reaction was diluted with dichloromethane and the organic phase was washed in each case three times with 10% strength $Na_2S_2O_3$ solution, 10% strength citric acid solution and saturated sodium hydrogencarbonate solution. The organic phase was dried over magnesium sulfate and the solvent was evaporated under reduced pressure. This gave 565.7 mg (97% of theory) of the title compound.

$^1$H-NMR (400 MHz, DMSO-d$_6$): δ [ppm]=0.03 (s, 9H), 0.91 (m, 2H), 2.70-2.79 (m, 1H), 2.88 (dd, 1H), 3.63 (s, 3H), 4.04 (m, 2H), 4.55 (m, 1H), 7.54 (d, 1H), 9.60 (t, 1H).

Intermediate L119

Trifluoroacetic Acid tert-butyl N-(2-aminoethyl)-N²-[(benzyloxy)carbonyl]-D-alpha-glutaminate Salt

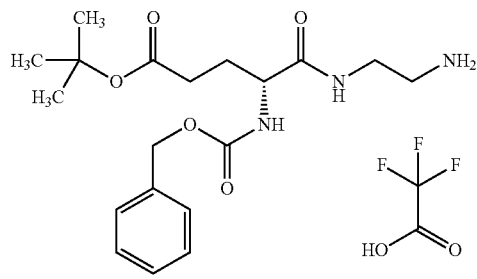 [SMILES: CC(C)(C)OC(=O)CC[C@@H](NC(=O)OCc1ccccc1)C(=O)NCCN ; O=C(O)C(F)(F)F]

Intermediate L119 was prepared by conventional methods of peptide chemistry by coupling commercial (2R)-2-{[(benzyloxy)carbonyl]amino}-5-tert-butoxy-5-oxopentanoic acid (1.00 g, 2.96 mmol) and tert-butyl (2-aminoethyl)carbamate (560 µl, 3.6 mmol) in the presence of HATU and subsequent acidic removal of the Boc protective group using 10% strength TFA in dichloromethane, with substantial preservation of the t-butyl ester protective group. Purification by preparative HPLC gave the title compound.

LC-MS (Method 1): R$_t$=0.62 min; MS (ESI-pos): m/z=380 (M+H)$^+$.

Intermediate L120

Benzyl N-(2-aminoethyl)-N2-[(benzyloxy)carbonyl]-D-alpha-glutaminate

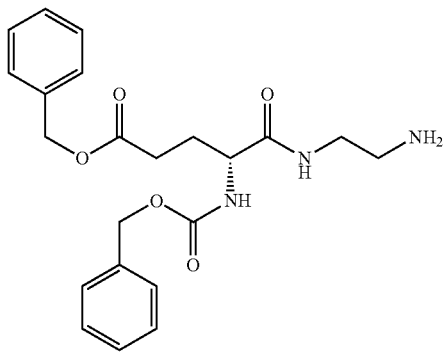 [SMILES: NCCNC(=O)[C@@H](CCC(=O)OCc1ccccc1)NC(=O)OCc1ccccc1]

Intermediate L120 was prepared by conventional methods of peptide chemistry by coupling commercial (2R)-5-(benzyloxy)-2-{[(benzyloxy)carbonyl]amino}-5-oxopentanoic acid (830 mg, 2.23 mmol) and tert-butyl (2-aminoethyl)carbamate (420 µl, 2.7 mmol) in the presence of HATU and subsequent acidic removal of the Boc protective group using TFA in dichloromethane.

Intermediate F104

Trifluoroacetic Acid (2S)-2-amino-4-[{(1R)-1-[1-benzyl-4-(2,5-difluorophenyl)-1H-pyrrol-2-yl]-2,2-dimethylpropyl}(glycoloyl)amino]-N-(2-{[(2,5-dioxo-2,5-dihydro-1H-pyrrol-1-yl)acetyl]amino}ethyl) butanamide Salt

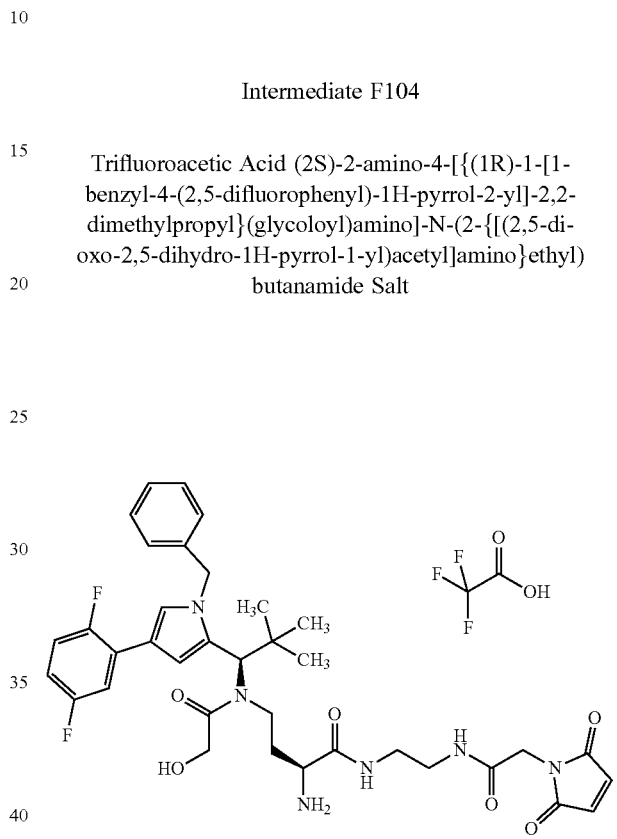

300 mg (0.456 mmol) of intermediate C58 were dissolved in 38 ml of DMF, and 142 mg (0.456 mmol) of intermediate L1 and 260 mg (0.684 mmol) of HATU and 318 µl of N,N-diisopropylethylamine were added. The mixture was stirred at RT for 60 min and then concentrated. The residue was purified by preparative HPLC, giving, after lyophilization, 338 mg (87% of theory) of the protected intermediate.

LC-MS (Method 1): R$_t$=1.30 min; MS (ESIpos): m/z=837 (M+H)$^+$.

In the second step, 338 mg (0.404 mmol) of this intermediate were dissolved in 40 ml of 2,2,2-trifluoroethanol. 330.2 mg (2.42 mmol) of zinc chloride were added and the mixture was stirred at 50° C. for 3 h. 708 mg (2.42 mmol) of ethylenediamine-N,N,N',N'-tetraacetic acid and 4 ml of a 0.1% strength aqueous trifluoroacetic acid solution were then added. The mixture was purified by preparative HPLC. Concentration of the appropriate fractions and lyophilization of the residue from acetonitrile/water gave 265 mg (81% of theory) of the title compound.

LC-MS (Method 1): R$_t$=0.82 min; MS (ESIpos): m/z=693 (M+H)$^+$.

Intermediate F325

N-[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-$N^2$-[(2,5-dioxo-2,5-dihydro-1H-pyrrol-1-yl)acetyl]-D-alpha-glutamine trifluoroacetic Acid Salt

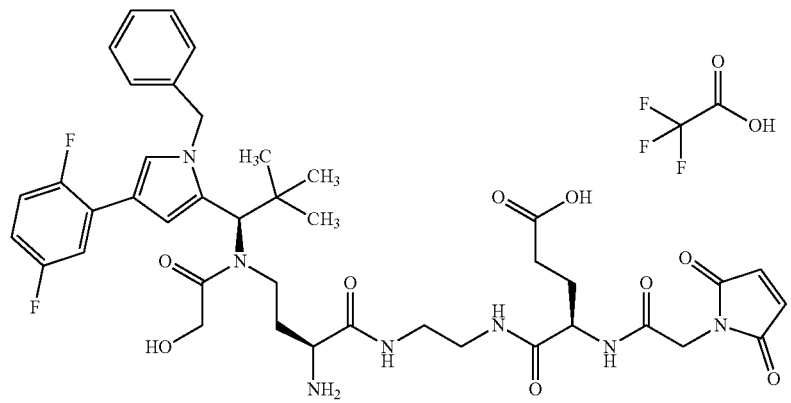 [SMILES: CC(C)(C)[C@H](c1cc(-c2cc(F)ccc2F)cn1Cc1ccccc1)N(CC[C@H](N)C(=O)NCCNC(=O)[C@@H](CCC(=O)O)NC(=O)CN1C(=O)C=CC1=O)C(=O)CO ; O=C(O)C(F)(F)F]
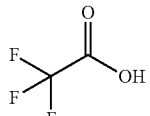
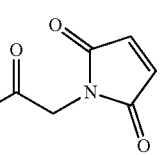

30 mg (0.046 mmol) of intermediate C58 were coupled with 29 mg (0.055 mmol) of trifluoroacetic acid benzyl N-(2-aminoethyl)-N2-[(benzyloxy)carbonyl]-D-alpha-glutaminate salt (intermediate L120) in the presence of 1.5 equiv. of HATU and 3 equiv. of N,N-diisopropylethylamine. Purification by preparative HPLC gave 39.5 mg (82% of theory) of the protected intermediate. From this intermediate, initially the benzyl ester groups were removed hydrogenolytically. Subsequently, coupling with 1-{2-[(2,5-dioxopyrrolidin-1-yl)-oxy]-2-oxoethyl}-1H-pyrrole-2,5-dione was carried out in DMF in the presence of 3 equiv. of N,N-diisopropylethylamine. In the last step, 13.5 mg (0.012 mmol) of this intermediate were dissolved in 5 ml of 2,2,2-trifluoroethanol. 13 mg (0.096 mmol) of zinc chloride were added and the mixture was stirred at 50° C. for 3 h. Subsequently, 28 mg (0.096 mmol) of ethylenediamine-N,N,N',N'-tetraacetic acid were added. The mixture was purified by preparative HPLC. Concentration of the appropriate fractions and lyophilization of the residue from acetonitrile/water gave 9 mg (81% of theory) of the title compound.

LC-MS (Method 12): $R_t$=1.44 min; MS (ESIpos): m/z=822 (M+H)$^+$.

B: Preparation of Antibody-Drug Conjugates (ADC)

B-1. General Method for Generation of Anti-CD123 and Anti-CXCR5 Antibodies and Chimeric and Humanized Variants of Anti-CD123 and Anti-CXCR5 Antibodies The protein sequence (amino acid sequence) of the antibodies used, for example the anti-CD123 antibodies TPP-8987, TPP-8988 and TPP-9476 and the anti-CXCR5 antibodies TPP-9024, TPP-9574 and TPP-9580, was transformed into a DNA sequence that encodes the respective protein by a method known to those skilled in the art and inserted into an expression vector suitable for transient mammalian cell culture (as described by Tom et al., Chapter 12 in Methods Express: Expression Systems, edited by Michael R. Dyson and Yves Durocher, Scion Publishing Ltd, 2007).

B-2. General Method for Expression of Antibodies in Mammalian Cells

The antibodies, for example the anti-CD123 antibodies TPP-8987, TPP-8988 and TPP-9476 and the anti-CXCR5 antibodies TPP-9024, TPP-9574 and TPP-9580, were produced in transient mammalian cell cultures, as described by Tom et al., Chapter 12 in Methods Express: Expression Systems, edited by Michael R. Dyson and Yves Durocher, Scion Publishing Ltd, 2007.

B-3. General Method for Purification of Antibodies from Cell Supernatants

The antibodies, for example the anti-CD123 antibodies TPP-8987, TPP-8988 and TPP-9476 and the anti-CXCR5 antibodies TPP-9024, TPP-9574 and TPP-9580, were obtained from the cell culture supernatants. The cell supernatants were clarified by centrifugation of cells. The cell supernatant was then purified by affinity chromatography on a MabSelect Sure (GE Healthcare) chromatography column. To this end, the column was equilibrated in DPBS pH 7.4 (Sigma/Aldrich), the cell supernatant was applied and the column was washed with about 10 column volumes of DPBS pH 7.4+500 mM sodium chloride. The antibodies were eluted in 50 mM sodium acetate pH 3.5+500 mM sodium chloride and then purified further by gel filtration chromatography on a Superdex 200 column (GE Healthcare) in DPBS pH 7.4.

Commercially available antibodies were purified by standard chromatography methods (protein A chromatography, preparative gel filtration chromatography (SEC—size exclusion chromatography)) from the commercial products.

B-4. General Method for Coupling to Cysteine Side Chains

The following antibodies were used in the coupling reactions:
anti-CD123 AK TPP-8987
anti-CD123 AK TPP-8988
anti-CD123 AK TPP-9476
anti-CXCR5 AK TPP-9024
anti-CXCR5 AK TPP-9574
anti-CXCR5 AK TPP-9580

Small-Scale Coupling:

Between 2 and 5 equivalents of tris(2-carboxyethyl)phosphine hydrochloride (TCEP), dissolved in PBS buffer, were added to a solution of 2-5 mg of the appropriate antibody in PBS buffer in the concentration range between 1 mg/ml and 20 mg/ml, preferably in the range of about 5 mg/ml to 15 mg/ml, and the mixture was stirred at RT for 30 min to 1 h.

Subsequently, depending on the intended loading, from 2 to 12 equivalents, preferably about 5-10 equivalents of the maleimide precursor compound to be coupled were added as a solution in DMSO. Here, the amount of DMSO should not exceed 10% of the total volume. The mixture was stirred at RT for 60-240 min and subsequently diluted with PBS buffer, which had been adjusted to pH 8 beforehand, to a volume of 2.5-7.5 ml and then passed through a PD 10 column (Sephadex® G-25, GE Healthcare) equilibrated with PBS buffer pH 8, and eluted with PBS buffer pH 8. The eluate was stirred at RT under argon overnight. Subsequently, the solution was concentrated by ultracentrifugation and rediluted with PBS buffer (pH 7.2).

Medium-Scale Coupling:

Under argon, a solution of 2-5 equivalents, preferably 3 equivalents, of TCEP in PBS buffer (c~0.2-0.8 mg/ml, preferably 0.5 mg/ml) was added to 20-200 mg of the antibody in question in PBS buffer (c~5-15 mg/ml). The mixture was stirred at RT for 30 min, and then 2-12, preferably 5-10, equivalents of a maleimide precursor compound dissolved in DMSO were added. After stirring at RT for a further 1.5 h-2 h, the mixture was diluted with PBS buffer which had been adjusted to pH 8 beforehand.

This solution was then applied to PD 10 columns (Sephadex® G-25, GE Healthcare) which had been equilibrated with PBS buffer pH 8 and was eluted with PBS buffer pH 8. The eluate was diluted with PBS buffer pH 8 to a concentration of 1-5 mg/ml. This solution was stirred at RT under argon overnight. If required, the solution was then rebuffered to pH 7.2. The ADC solution was concentrated by ultracentrifugation, rediluted with PBS buffer (pH 7.2) and then optionally concentrated again to a concentration of about 10 mg/ml.

In the structural formulae shown, AK can have the meaning taken from the tables according to the working examples:

anti-CD123 AK TPP-8987 (partially reduced)-S§ [1]
anti-CD123 AK TPP-8988 (partially reduced)-S§ [1]
anti-CD123 AK TPP-9476 (partially reduced)-S§ [1]
anti-CXCR5 AK TPP-9024 (partially reduced)-S§ [1]
anti-CXCR5 AK TPP-9574 (partially reduced)-S§ [1]
anti-CXCR5 AK TPP-9580 (partially reduced)-S§ [1]

wherein

§ [1] represents the linkage to the succinimide group or to any isomeric hydrolysed open-chain succinamides or the alkylene radical resulting therefrom, and S represents the sulfur atom of a cysteine residue of the partially reduced antibody.

Further Purification and Characterization of the Conjugates According to the Invention After the reaction, in some instances the reaction mixture was concentrated, for example by ultrafiltration, and then desalted and purified by chromatography, for example using a Sephadex® G-25 column. Elution was carried out, for example, with phosphate-buffered saline (PBS). The solution was then sterile filtered and frozen. Alternatively, the conjugate can be lyophilized.

B-7. Determination of the Antibody, the Toxophore Loading and the Proportion of Open Cysteine Adducts For protein identification in addition to molecular weight determination after deglycosylation and/or denaturing, a tryptic digestion was carried out which, after denaturing, reduction and derivatization, confirms the identity of the protein via the tryptic peptides found.

toxophore loading (in the tables referred to as DAR, drug-to-antibody ratio) of the PBS buffer solutions obtained of the conjugates described in the working examples was determined as follows:

Determination of toxophore loading of lysine-linked ADCs was carried out by mass spectrometry determination of the molecular weights of the individual conjugate species. Here, the antibody conjugates were first deglycosylated with PNGaseF, and the sample was acidified and, after HPLC separation/desalting, analysed by mass spectrometry using ESI-MicroTof$_Q$ (Bruker Daltonik). All spectra over the signal in the TIC (Total Ion Chromatogram) were added and the molecular weight of the different conjugate species was calculated based on MaxEnt deconvolution. The DAR (=drug/antibody ratio) was then calculated after signal integration of the different species. For this purpose, the sum total of the integration results for all species weighted by the toxophore count was divided by the sum total of the simply weighted integration results for all species.

The toxophore loading of cysteine-linked conjugates was determined by reversed-phase chromatography of the reduced and denatured ADCs. Guanidinium hydrochloride (GuHCl) (28.6 mg) and a solution of DL-dithiothreitol (DTT) (500 mM, 3 µl) were added to the ADC solution (1 mg/ml, 50 µl). The mixture was incubated at 55° C. for one hour and analysed by HPLC.

HPLC analysis was carried out on an Agilent 1260 HPLC system with detection at 220 nm. A Polymer Laboratories PLRP-S polymeric reversed-phase column (catalogue number PL1912-3802) (2.1×150 mm, 8 µm particle size, 1000 Å) was used at a flow rate of 1 ml/min with the following gradient: 0 min, 25% B; 3 min, 25% B; 28 min, 50% B. Eluent A consisted of 0.05% trifluoroacetic acid (TFA) in water, eluent B of 0.05% trifluoroacetic acid in acetonitrile.

The detected peaks were assigned by retention time comparison with the light chain (L0) and the heavy chain (H0) of the non-conjugated antibody. Peaks detected exclusively in the conjugated sample were assigned to the light chain with one toxophore (L1) and the heavy chains with one, two and three toxophores (H1, H2, H3).

Average loading of the antibody with toxophores (referred to as DAR, drug-to-antibody ratio) was calculated from the peak areas determined by integration as double the sum of HC load and LC load, where LC load is calculated from the sum of the toxophore number-average weighed integration results of all LC peaks divided by the sum of the singly weighed integration results of all LC peaks, and where the HC load is calculated from the sum of the toxophore number-average weighed integration results of all HC peaks divided by the sum of the singly weighed integration results of all HC peaks. In individual cases, it was be possible that, owing to co-elution of some peaks, it was not possible to determine toxophore loading accurately.

In the cases where light and heavy chains could not be separated sufficiently by HPLC, determination of toxophore loading of cysteine-linked conjugates was carried out by mass spectrometry determination of the molecular weights of the individual conjugate species at light and heavy chain.

For this purpose, guanidinium hydrochloride (GuHCl) (28.6 mg) and a solution of DL-dithiothreitol (DTT) (500 mM, 3 µl) were added to the ADC solution (1 mg/ml, 50 µl). The mixture was incubated for one hour at 55° C. and analysed by mass spectrometry after online desalting using ESI-MicroTofQ (Bruker Daltonik).

For the DAR determination, all spectra were added over the signal in the TIC (Total Ion Chromatogram), and the molecular weight of the different conjugate species at light and heavy chain was calculated based on MaxEnt deconvolution. The average loading of the antibody with toxophores was determined from the peak areas determined by integration as twice the sum total of the HC loading and the LC loading. In this context, the LC loading is calculated from the sum total of the integration results for all LC peaks weighted by the toxophore count, divided by the sum total of the simply weighted integration results for all LC peaks, and the HC loading from the sum total of the integration results for all HC peaks weighted by the toxophore count, divided by the sum total of the simply weighted integration results for all HC peaks.

In the case of the open constructs, to determine the proportion of the open cysteine adduct, the molecular weight area ratio of closed to open cysteine adduct (molecular weight delta 18 daltons) of all singly conjugated light and heavy chain variants was determined. The mean of all variants yielded the proportion of the open cysteine adduct.

B-8. Verification of the Antigen Binding of the ADC

The capability of the binder of binding to the target molecule was checked after coupling had taken place. The person skilled in the art is familiar with various methods which can be used for this purpose; for example, the affinity of the conjugate can be checked using ELISA technology or surface plasmon resonance analysis (BIAcore™ measurement). The conjugate concentration can be measured by the person skilled in the art using customary methods, for example for antibody conjugates by protein determination. (see also Doronina et al.; Nature Biotechnol. 2003; 21:778-784 and Polson et al., Blood 2007; 1102:616-623).

Working Examples ADCs

The ADCs shown in the structural formulae of the working examples and the reference examples, which were coupled to the cysteine side chains of the antibodies via maleimide radicals, are, depending on the linker and the coupling procedure, mainly present in the ring-opened form shown. However, the preparation may comprise a small proportion of the ring-closed form.

Examples 1

Exemplary Procedure A:

Under argon, a solution of 0.029 mg of TCEP in 0.05 ml of PBS buffer was added to 5 mg of the antibody in question in 0.5 ml of PBS (c=10 mg/ml). The mixture was stirred at RT for 30 min, and then 0.26 mg (0.00023 mmol) of Intermediate F325 dissolved in 50 µl of DMSO was added. After stirring at RT for a further 90 min, the mixture was diluted to a volume of 2.5 ml PBS buffer which had been adjusted to pH 8 beforehand and then passed through a PD 10 column (Sephadex® G-25, GE Healthcare) equilibrated with PBS buffer pH 8, and eluted with PBS buffer pH 8. The eluate was then stirred at RT under argon overnight. This was followed by concentration by ultracentrifugation and redilution with PBS buffer (pH 7.2).

Exemplary Procedure B:

Under argon, a solution of 0.172 mg of TCEP in 0.3 ml of PBS buffer was added to 30 mg of the antibody in question in 3 ml of PBS (c=10 mg/ml). The mixture was stirred at RT for 30 min, and then 1.57 mg (0.0014 mmol) of Intermediate F325 dissolved in 300 µl of DMSO was added. After stirring at RT for a further 90 min, the mixture was diluted to a volume of 5 ml PBS buffer which had been adjusted to pH 8 beforehand, then passed through a PD 10 column (Sephadex® G-25, GE Healthcare) equilibrated with PBS buffer pH 8, and eluted with PBS buffer pH 8. The eluate was then stirred at RT under argon overnight. This solution was then applied to a PD 10 column (Sephadex® G-25, GE Healthcare) which had been equilibrated with PBS buffer pH 7.2 and was eluted with PBS buffer pH 7.2. The eluate was then concentrated by ultracentrifugation, rediluted with PBS buffer (pH 7.2), reconcentrated and then sterile-filtered.

The following ADCs were prepared analogously to these procedures and characterized as indicated in the table:

| Example | Target | Antibody (TPP-) | Procedure | C [mg/mL] | DAR |
|---|---|---|---|---|---|
| 1c-8987 | CD123 | 8987 | B | 7.63 | 3.7 |
| 1c-8988 | CD123 | 8988 | B | 9.10 | 3.5 |
| 1c-9476 | CD123 | 9476 | B | 8.5 | 3.1 |
| 1x-9024 | CXCR5 | 9024 | B | 8.76 | 3.8 |
| 1x-9574 | CXCR5 | 9574 | B | 9.48 | 4.1 |
| 1x-9580 | CXCR5 | 9580 | B | 9.25 | 4.2 |

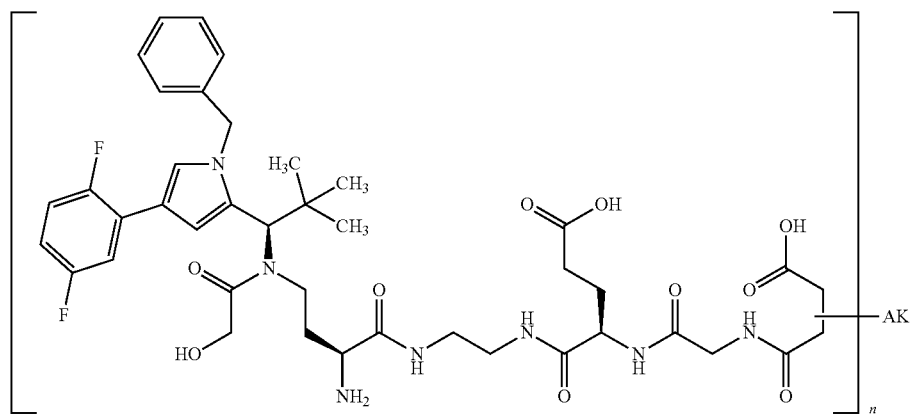

Working Examples of Metabolites

Example M1

N-(3-{[(2R)-2-Amino-2-carboxyethyl]sulfanyl}-3-carboxypropanoyl)glycyl-N-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-D-alpha-glutamine trifluoroacetic Acid Salt Regioisomer 1, Epimer Mixture

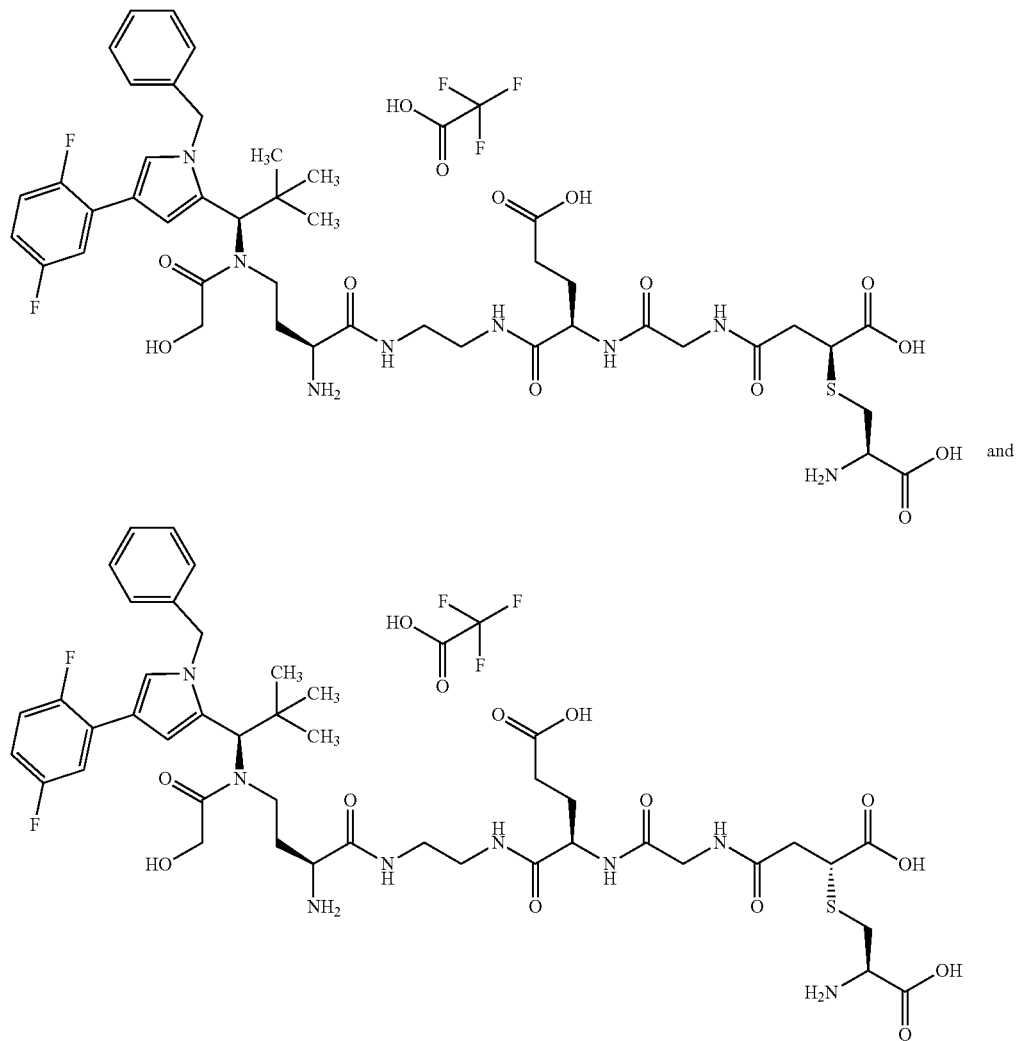

Triethylamine (10 ml, 73 mmol) and then 1-({[2-(trimethylsilyl)ethoxy]carbonyl}oxy)pyrrolidine-2,5-dione (8.31 g, 32.0 mmol) were added to a solution of methyl L-cysteinate hydrochloride (1:1) (5.00 g, 29.1 mmol) in 1,4-dioxane (200 ml). The reaction was stirred at room temperature for 20 h. The solid was then filtered off and the filtrate was concentrated under high vacuum. The residue was purified by preparative HPLC.

210 µl (1.4 mmol) of 1,8-diazabicyclo[5.4.0]undec-7-ene were added to a solution of the methyl N-{[2-(trimethylsilyl)ethoxy]carbonyl}-L-cysteinate obtained (130 mg, 465 µmop and 3-bromo-4-methoxy-4-oxobutanoic acid (393 mg, 1.86 mmol) in DMF (6.5 ml), and the reaction was stirred at room temperature for 10 min. The reaction was then concentrated under reduced pressure and the residue was purified by preparative HPLC. The solvent was evaporated under reduced pressure and the residue was dried under high vacuum.

The resulting intermediate was coupled by conventional methods of peptide chemistry in the presence of HATU with intermediate C119. The methyl esters were then hydrolysed by treating with a solution of lithium hydroxide in THF/water (1:1).

In the last step, 22 mg of the intermediate obtained were dissolved in 10 ml of 2,2,2-trifluoroethanol. 34 mg (0.252 mmol) of zinc chloride were added and the mixture was stirred at 50° C. for 1 h. 74 mg (0.252 mmol) of ethylenediamine-N,N,N',N'-tetraacetic acid, 10 ml of water and 500 µl of TFA were then added. The mixture was filtered and the solvent was evaporated under reduced pressure. The residue was purified by preparative HPLC. Concentration of the appropriate fractions and lyophilization of the residue from acetonitrile/water gave 13 mg (72% of theory) of the title compound.

LC-MS (Method 5): Rt=2.44 min; MS (ESIneg): m/z=959 [M−H]⁻

Example M2

N-(2-{[(2R)-2-Amino-2-carboxyethyl]sulfanyl}-3-carboxypropanoyl)glycyl-N-[2-({(2S)-2-amino-4-[{(1R)-1-[1-benzyl-4-(2,5-difluorophenyl)-1H-pyrrol-2-yl]-2,2-dimethylpropyl}-(glycoloyl)amino]butanoyl}amino)ethyl]-D-alpha-glutamine Trifluoroacetic Acid Salt Regioisomer 2, Epimer Mixture

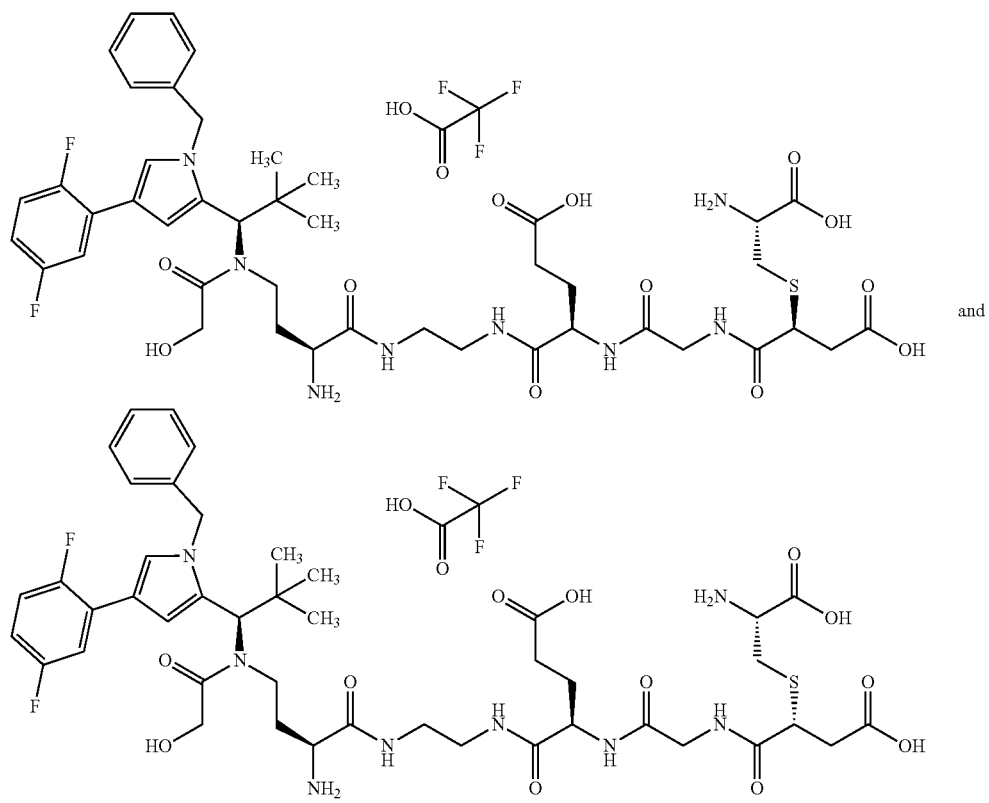

The title compounds M2 were prepared as epimer mixture analogously to Example M1:

801 μl (5.4 mmol) of 1,8-diazabicyclo[5.4.0]undec-7-ene were added to a solution of methyl N-{[2-(trimethylsilyl)ethoxy]carbonyl}-L-cysteinate (1000 mg, 3.58 mmol) and 2-bromo-4-ethoxy-4-oxobutanoic acid (926 mg, 4.11 mmol) in DMF (40 ml), and the reaction was stirred at room temperature for 2 h. The reaction was then concentrated under reduced pressure and the residue was purified by preparative HPLC.

The intermediate obtained was coupled by conventional methods of peptide chemistry in the presence of HATU and methylmorpholine with intermediate C119. The methyl ester and the ethyl ester were then hydrolysed by treatment with a solution of lithium hydroxide in THF/water (1:1).

In the last step, 48 mg of this intermediate were dissolved in 5 ml of 2,2,2-trifluoroethanol. 75 mg (0.550 mmol) of zinc chloride were added and the mixture was stirred at 50° C. for 3 h. 160 mg (0.550 mmol) of ethylenediamine-N,N,N',N'-tetraacetic acid, 2 ml of water and 20 μl of TFA were then added. The solvent was concentrated under reduced pressure and the residue was purified by preparative HPLC. Concentration of the appropriate fractions and lyophilization of the residue from acetonitrile/water gave 14 mg (39% of theory) of the title compound.

LC-MS (Method 5): Rt=2.41 min; MS (ESIneg): m/z=959 [M−H]−

For comparison, the reference-ADCs R1 were prepared. In section C, the superiority of the ADCs according to the invention from Example 1 over the corresponding reference-ADCs R1 is shown in an exemplary manner.

Reference Examples R1

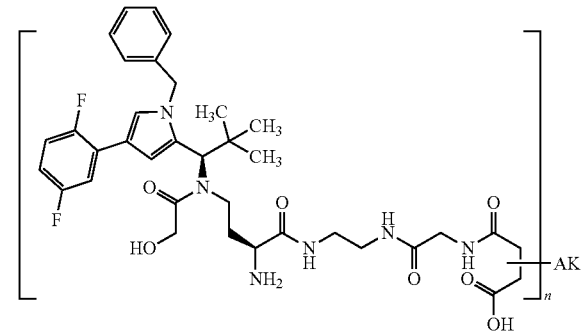

Exemplary Procedure

Under argon, a solution of 0.172 mg of TCEP in 300 µl of PBS buffer was added to 30 mg of the appropriate AK in 3 ml of PBS (c=10 mg/mL). The mixture was stirred at RT for 30 min, and 1.291 mg (1.6 µmop of intermediate F104, dissolved in 300 µl of DMSO, were then added. After a further 90 min of stirring at RT, the mixture was diluted with 1.4 ml of PBS buffer which had been adjusted to pH 8 beforehand.

This solution was then passed over PD 10 columns (Sephadex® G-25, GE Healthcare) equilibrated with PBS buffer pH 8 and eluted with PBS buffer pH 8. The eluate was diluted with PBS buffer pH 8 to a total volume of 7.5 ml. This solution was stirred at RT under argon overnight and then, once more using PD-10 columns, rebuffered to pH 7.2. The eluate was diluted to a total volume of 14 ml. By ultracentrifugation, the mixture was then concentrated to 2 ml, rediluted to 14 ml with PBS buffer (pH 7.2) and re-concentrated to a volume of 3 ml. The sample is filtered through a centrifuge tube (Microsep Advance Centrifugal Device 0.2 µm Supor Membrane/from PALL). The ADC batch obtained was characterized as follows:

The following ADCs were prepared analogously to these procedures and characterized as stated in the table:

| Example | Target | Antibody (TPP-) | C [mg/mL] | DAR |
|---|---|---|---|---|
| R1c-8987 | CD123 | 8987 | 9.11 | 1.5 |
| R1c-8988 | CD123 | 8988 | 6.45 | 3.4 |
| R1c-9476 | CD123 | 9476 | 7.0 | 3.1 |
| R1x-9024 | CXCR5 | 9024 | 9.47 | 3.7 |
| R1x-9574 | CXCR5 | 9574 | 7.57 | 3.9 |
| R1x-9580 | CXCR5 | 9580 | 9.10 | 3.7 |

Also for comparison, the metabolites Rm1 and Rm2 formed from the Reference Examples R1 were prepared:

Reference Example Rm1

4-[(2-{[2-({(2S)-2-Amino-4-[{(1R)-1-[1-benzyl-4-(2,5-difluorophenyl)-1H-pyrrol-2-yl]-2,2-dimethyl-propyl}(glycoloyl)amino]butanoyl}amino)ethyl]amino}-2-oxoethyl)amino]-2-{[(2R)-2-amino-2-carboxyethyl]sulfanyl}-4-oxobutanoic Acid Trifluoroacetic Acid Salt Regioisomer 1 as Epimer Mixture:

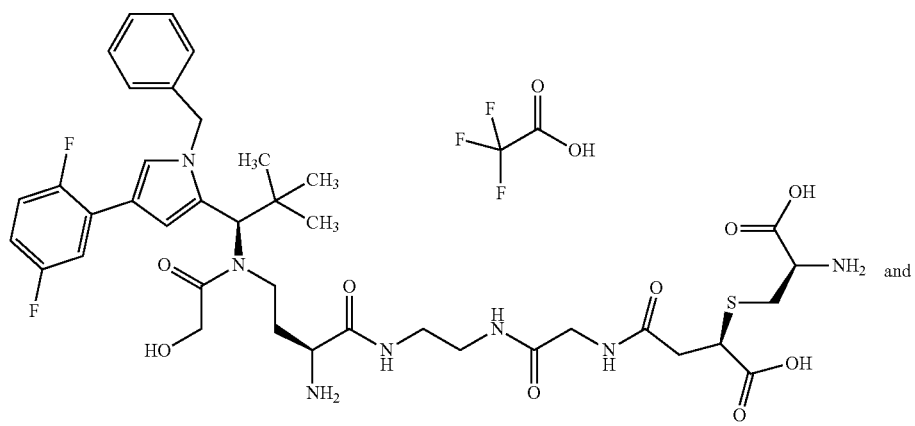

and

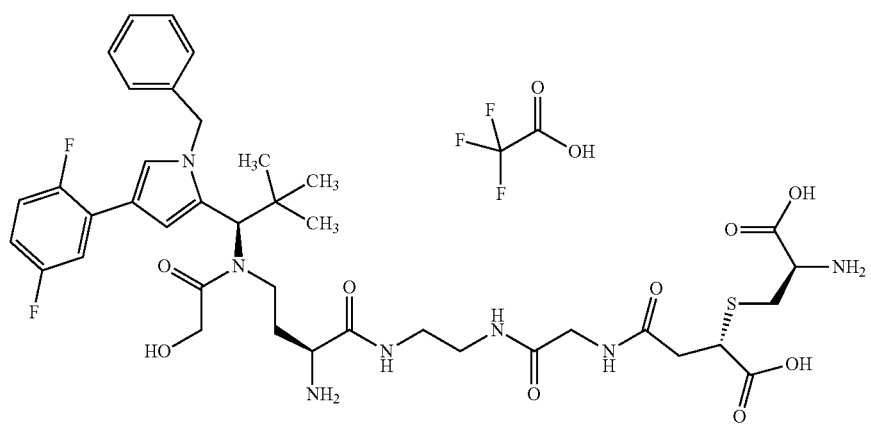

First, methyl L-cysteinate hydrochloride (1:1) was converted into methyl N-{[2-(trimethylsilyl)ethoxy]carbonyl}-L-cysteinate using 1-({[2-(trimethylsilyl)ethoxy]carbonyl}oxy)pyrrolidine-2,5-dione in DMF in the presence of N,N-diisopropylethylamine.

A little at a time, 208 μl (1.4 mmol) of 1,8-diazabicyclo[5.4.0]undec-7-ene were added to a solution of methyl N-{[2-(trimethylsilyl)ethoxy]carbonyl}-L-cysteinate (130 mg, 465 μmop and 3-bromo-4-methoxy-4-oxobutanoic acid (393 mg, 1.86 mmol) in DMF (6.5 ml), and the reaction was stirred at room temperature for 10 min. The mixture was then concentrated under reduced pressure and the residue was purified by preparative HPLC. The solvent was evaporated under reduced pressure and the residue was dried under high vacuum.

The intermediate obtained was coupled with intermediate C66 by conventional methods of peptide chemistry in the presence of HATU. The methyl esters were then hydrolysed by treatment with a solution of lithium hydroxide in THF/water (1:1).

In the last step, 18 mg of this intermediate were dissolved in 10.6 ml of 2,2,2-trifluoroethanol. 22 mg (0.16 mmol) of zinc chloride were added and the mixture was stirred at 50° C. for 2 h. 47 mg (0.16 mmol) of ethylenediamine-N,N,N',N'-tetraacetic acid and 2 ml of water and 2-3 drops of TFA were then added. The mixture was filtered and the solvent was evaporated under reduced pressure. The residue was purified by preparative HPLC. Concentration of the appropriate fractions and lyophilization of the residue from acetonitrile/water gave 10.5 mg (78.5% of theory) of the title compound (isomer 2) as regioisomer mixture.

LC-MS (Method 5): Rt=2.43 min; MS (ESI-pos): m/z=832 [M+H]⁺

Reference Example Rm2

4-[(2-{[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-3-{[(2R)-2-amino-2-carboxyethyl]sulfanyl}-4-oxobutanoic Acid Trifluoroacetic Acid Salt Isomer 2 as Epimer Mixture:

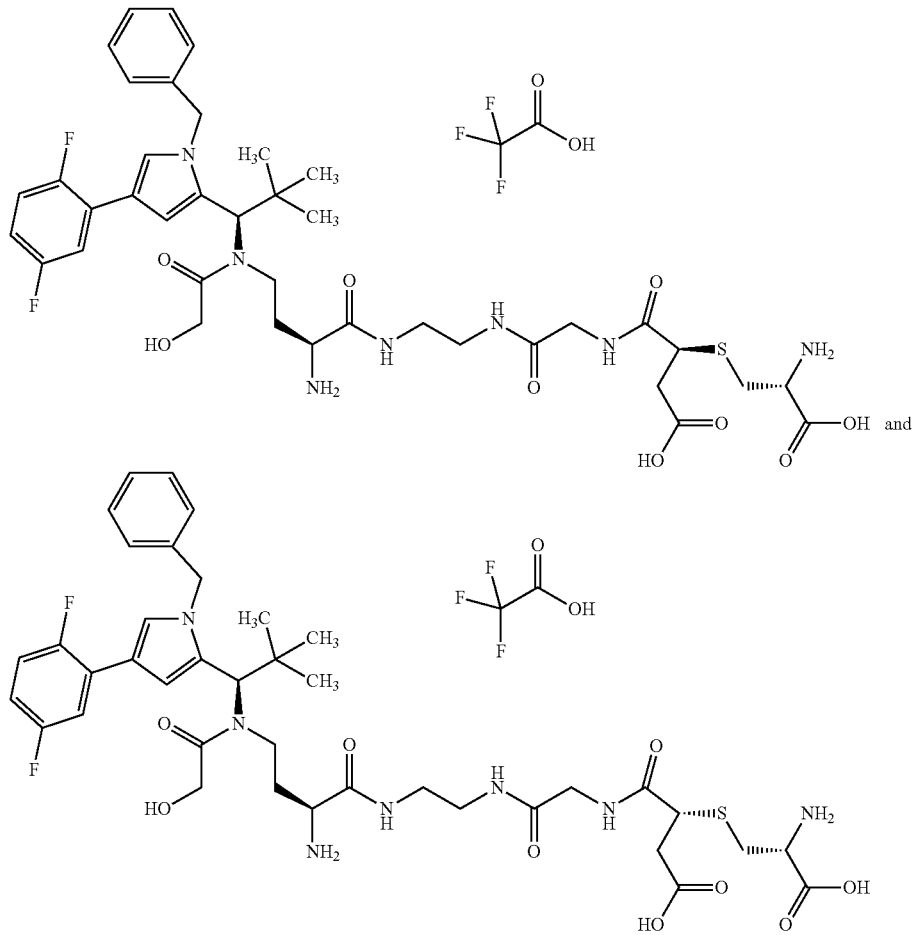

First, methyl L-cysteinate hydrochloride (1:1) was converted into methyl N-{[2-(trimethylsilyl)ethoxy]carbonyl}-L-cysteinate using 1-({[2-(trimethylsilyl)ethoxy]carbonyl}oxy)pyrrolidine-2,5-dione in DMF in the presence of N,N-diisopropylethylamine.

801 μl (5.4 mmol) of 1,8-diazabicyclo[5.4.0]undec-7-ene were added to a solution of methyl N-{[2-(trimethylsilyl)ethoxy]carbonyl}-L-cysteinate (1000 mg, 3.58 mmol) and 2-bromo-4-ethoxy-4-oxobutanoic acid (926 mg, 4.11 mmol) in DMF (40 ml), and the reaction was stirred at room temperature for 2 h. The mixture was then concentrated under reduced pressure and the residue was purified by preparative HPLC. The solvent was evaporated under reduced pressure and the residue was dried under high vacuum.

The intermediate obtained was coupled with intermediate C66 by conventional methods of peptide chemistry in the presence of HATU. The methyl ester and the ethyl ester were then hydrolysed by treatment with a solution of lithium hydroxide in THF/water (1:1).

In the last step, 24 mg of this intermediate were dissolved in 6.4 ml of 2,2,2-trifluoroethanol. 28.5 mg (0.21 mmol) of zinc chloride were added and the mixture was stirred at 50° C. for 2 h. 61 mg (0.21 mmol) of ethylenediamine-N,N,N',N'-tetraacetic acid and 2 ml of water and 2-3 drops of TFA were then added. The mixture was filtered and the solvent was evaporated under reduced pressure. The residue was purified by preparative HPLC. Concentration of the appropriate fractions and lyophilization of the residue from acetonitrile/water gave 14.5 mg (71% of theory) of the title compound.

LC-MS (Method 5): Rt=2.41 min; MS (ESI-pos): m/z=832 [M+H]$^+$

C: Assessment of Biological Efficacy

The biological activity of the compounds according to the invention can be shown in the assays described below:

C-1a: Determination of the Cytotoxic Effect of the ADCs Directed Against CD123 and CXCR5

The analysis of the cytotoxic effect of the exemplary ADCs was carried out with various cell lines:

NCI-H292: human mucoepidermoid lung carcinoma cells, ATCC-CRL-1848, standard medium: RPMI 1640 (Biochrom; #FG1215, stab. glutamine)+10% FCS (Sigma; #F2442), TWEAKR-positive; EGFR-positive, KPL4: human breast cancer cell line, Bayer Pharma AG (identity checked and confirmed on 19 Jul. 2012 at DSMZ), standard medium: RPMI 1640 (from Gibco; #21875-059, stab. L-glutamine)+10% heat inactivated FCS (Gibco, No. 10500-064); HER2-positive.

SK-HEP-1: human liver cell cancer line, ATCC No. HTB-52, standard medium: MEM with Earle's salts+Glutamax I (Invitrogen 41090)+10% heat inactivated FCS (from Gibco, No. 10500-064); TWEAKR-positive MOLM-13: human acute monocytic leukaemia cells (AML-M5a), DSMZ, No. ACC 554, standard medium: RPMI 1640 (from Gibco; #21875-059, stab. L-glutamine)+20% heat inactivated FCS (Gibco, No. 10500-064); CD123-positive.

MV-4-11: human biphenotypic B myelomonocytic leukaemia cells obtained from peripheral blood, ATCC-CRL-9591, standard medium: IMDM (ATCC: 30-2005), +10% heat inactivated FCS (Gibco, No. 10500-064); CD123-positive NB4: human acute promyelocytic leukaemia cells obtained from bone marrow, DSMZ, No. ACC 207, standard medium: RPMI 1640+GlutaMAX I (Invitrogen 61870)+10% heat inactivated FCS (Gibco, No. 10500-064)+2.5 g of glucose (20% glucose solution, Gibco, No. 19002)+10 mM Hepes (Invitrogen 15630)+1 mM sodium pyruvate (Invitrogen 11360); CD123-negative Rec-1: human mantle cell lymphoma cells (B cell non-Hodgkin's lymphoma) ATCC CRL-3004, standard medium: RPMI 1640+GlutaMAX I (Invitrogen 61870)+10% heat inactivated FCS (Gibco, No. 10500-064) CXCR5-positive The cells were cultivated by the standard method as stated by the American Tissue Culture Collection (ATCC) or the Leibniz-Institut DSMZ-Deutsche Sammlung von Mikroorganismen and Zellkulturen GmbH (DSMZ) for the cell lines in question.

MTT Assay

The cells were cultivated by the standard method, with the growth media specified in section C-1. The test was carried out by detaching the cells with a solution of Accutase in PBS (from Biochrom AG #L2143), pelletizing, resuspending in culture medium, counting and sowing into a 96-well culture plate with white bottom (from Costar #3610) (NCI H292: 2500 cells/well; SK-HEP-1: 1000 cells/well; KPL-4: 1200 cells/well; in total volume 100 µl). The cells were then incubated in an incubator at 37° C. and 5% carbon dioxide. After 48 h, the medium was replaced. The antibody drug conjugates in 10 µl of culture medium in concentrations from $10^{-5}$M to $10^{-13}$M were then pipetted to the cells (in triplicate), and the assay was then incubated in an incubator at 37° C. and 5% carbon dioxide. The suspension cells were counted and sown into a 96-well culture plate with white bottom (from Costar #3610) (#3610) (MOLM-13: 2000 cells/well; NB4: 7000 cells/well; MV-4-11: 5000 cells/well in a total volume of 100 µl). After 6 hours of incubation at 37° C. and 5% carbon dioxide, the medium was changed and the antibody-drug conjugates or metabolites were added by pipette in 10 µl of culture medium in concentrations of $10^{-5}$M to $10^{-13}$M to the cells (triplicates) in 90 µl. The batch was incubated in an incubator at 37° C. and 5% carbon dioxide. After 96 h, the cell proliferation was detected using the MTT assay (ATCC, Manassas, Va., USA, catalogue No. 30-1010K). To this end, the MTT reagent was incubated with the cells for 4 h, followed by lysis of the cells overnight by addition of the detergent. The dye formed was detected at 570 nm (Infinite M1000 pro, Tecan). The measured data were used to calculate the $IC_{50}$ of the growth inhibition using the DRC (dose response curve). The proliferation of cells which were not treated with test substance but were otherwise identically treated was defined as the 100% figure.

Table 1a below sets out the $IC_{50}$ values for representative working examples from this assay:

TABLE 1a

| Example | MV-4-11 $IC_{50}$ [M] | MOLM-13 $IC_{50}$ [M] | Rec-1 $IC_{50}$ [M] |
|---|---|---|---|
| 1c-8987 | 1.26E-09 | 2.10E-10 | |
| 1c-8988 | 2.94E-08 | 3.02E-11 | |
| 1c-9476 | 2.78E-09 | 2.85E-10 | |
| 1x-9024 | | | 1.34E-10 |
| 1x-9574 | | | 2.94E-11 |
| 1x-9580 | | | 2.78E-09 |

Table 1b below lists the $IC_{50}$ values for representative reference examples from this assay.

TABLE 1b

| Example | MV-4-11 $IC_{50}$ [M] | MOLM-13 $IC_{50}$ [M] | Rec-1 $IC_{50}$ [M] |
|---|---|---|---|
| R1c-8987 | 1.33E-07 | 7.57E-08 | |
| R1c-8988 | 3.27E-08 | 4.26E-09 | |
| R1c-9476 | 5.30E-09 | 3.04E-10 | |
| R1x-9024 | | | 1.84E-10 |
| R1x-9574 | | | 2.62E-10 |
| R1x-9580 | | | 7.16E-11 |

The activity data reported relate to the working examples described in the present experimental section, with the drug/mAB ratios indicated. The values may possibly deviate for different drug/mAB ratios. The IC50 values are means of several independent experiments or individual values. The action of the antibody drug conjugates was selective for the respective isotype control comprising the respective linker and toxophore. In addition, the target specificity of the antibody-drug conjugates directed against CD123 was demonstrated by testing with a CD123-negative cell (NB4).

C-1 b: Determination of the Inhibition of the Kinesin Spindle Protein KSP/Eg5 by Selected Examples The motor domain of the human kinesin spindle protein KSP/Eg5 (tebu-bio/Cytoskeleton Inc, No. 027EG01-XL) was incubated in a concentration of 10 nM with microtubuli (bovine or porcine, tebu-bio/Cytoskeleton Inc) stabilized with 50 µg/ml taxol (Sigma No. T7191-5MG) for 5 min at RT in 15 mM PIPES, pH 6.8 (5 mM $MgCl_2$ and 10 mM DTT, Sigma). The freshly prepared mixture was aliquoted into a 384 MTP (from Corning). The inhibitors to be examined at concentrations of 1.0×10-6 M to 1.0×10-13 M and ATP (final concentration 500 µM, Sigma) were then added. Incubation was at RT for 2 h. ATPase activity was detected by detecting the inorganic phosphate formed using malachite green (Biomol). After addition of the reagent, the assay was incubated at RT for 50 min prior to detection of the absorption at a wavelength of 620 nm. The positive controls used were monastrol (Sigma, M8515-1 mg) and ispinesib (AdooQ Bioscience A10486). The individual data of the dose-activity curve are eight-fold determinations. The $IC_{50}$ values are means of two independent experiments. The 100% control was the sample which had not been treated with inhibitors.

Table 2 below lists the $IC_{50}$ values of representative working examples from the assay described and summarizes the corresponding cytotoxicity data (MTT assay):

The dye load of the antibodies examined here and the isotype control were of a comparable order of magnitude. In cell binding assays, it was confirmed that the coupling did not lead to any change in the affinity of the antibodies.

The labelled antibodies were used for the internalization assay. Prior to the start of the treatment, cells ($2\times10^4$/well) were sown in 100 µl medium in a 96-well MTP (fat, black, clear bottom No 4308776, from Applied Biosystems). After 18 h of incubation at 37° C./5% $CO_2$, the medium was replaced and labelled antibodies were added in different concentrations (10, 5, 2.5, 1, 0.1 µg/ml). The same treatment protocol was applied to the labelled isotype control (negative control). The chosen incubation times were 0 h, 0.25 h, 0.5 h, 1 h, 1.5 h, 2 h, 3 h, 6 h and 24 h. The fluorescence measurement was carried out using the InCellAnalyzer 1000 (from GE Healthcare). This was followed by kinetic evaluation via measurement of the parameters granule counts/cell and total granule intensity/cell.

Following binding to the receptor, the antibodies were examined for their internalization capacity. For this purpose, tumour cells with different receptor expression levels were chosen. A target-mediated highly specific internalization was observed with the antibodies of the invention, whereas the isotype control showed no internalization.

C-2b: Internalization Assay with Suspended Cells

Coupling of the fluorescent dye was carried out as described in section C-2. The antigen to be examined is expressed by haematopoietic suspension cells; consequently, the internalization was examined in an FACS-based internalization assay.

Cells having different target expression levels were examined. The cells ($5\times10^4$/well) were sown in a 96-MTP (Greiner bio-one, CELLSTAR, 650 180, U-bottom) in a total volume of 100 µl. After addition of the target-specific antibody in a final concentration of 10 µg/ml, the batches were incubated at 37° C. for different periods of time (1 h,

TABLE 2

| Example | KSP-Assay $IC_{50}$ [M] | NCI-H292 $IC_{50}$ [M] | SKHep-1 $IC_{50}$ [M] | KPL-4 $IC_{50}$ [M] | MV 4--11 $IC_{50}$ [M] | MOLM-13 $IC_{50}$ [M] |
|---|---|---|---|---|---|---|
| Rm1 | 9.44E−10 | 6.36E−08 | 1.90E−08 | | | |
| M1 | 2.13E−09 | 5.00E−07 | 9.88E−08 | 5.00E−07 | 3.02E−07 | 1.25E−07 |
| Rm2 | 2.03E−09 | 2.76E−07 | 8.90E−08 | | | |
| M2 | 4.67E−10 | | | | 1.85E−07 | 2.15E−07 |

The activity data reported relate to the working examples described in the present experimental section.

C-2a Internalization Assay

Internalization is a key process which enables specific and efficient provision of the cytotoxic payload in antigen-expressing cancer cells via antibody drug conjugates (ADC). This process is monitored via fluorescent labelling of specific antibodies and an isotype control antibody. First, the fluorescent dye was conjugated to lysines of the antibody. Conjugation was carried out using a two-fold molar excess of CypHer 5E mono NHS ester (Batch 357392, GE Healthcare) at pH 8.3. After the coupling, the reaction mixture was purified by gel chromatography (Zeba Spin Desalting Columns, 40K, Thermo Scientific, No. 87768; elution buffer: DULBECCO'S PBS, Sigma-Aldrich, No. D8537), to eliminate excess dye and to adjust the pH. The protein solution was concentrated using VIVASPIN 500 columns (Sartorius stedim biotec). The dye load of the antibody was determined by means of spectrophotometry analysis (from NanoDrop) and subsequent calculation (D/P=$A_{dye}$ $\varepsilon_{protein}$:($A_{280}$−0.16$A_{dye}$)$\varepsilon_{dye}$).

2 h, 6 h, in triplicate). The isotype control was treated under identical conditions. A parallel batch was treated and incubated constantly at 4° C. (negative control). FACS analysis was carried out using the Guava flow cytometer (Millipore). Kinetic evaluation was carried out by measuring the fluorescence intensity, and evaluation took place using the guavaSoft 2.6 software (Millipore). For the targets and target-specific antibodies described here, a significant and specific internalization was detected in various cells; the isotype controls showed no internalization.

C-2c: Co-Localization: Assays of the Anti-CD123 Antibodies

Owing to the linker, the active metabolite of the antibody-drug conjugate is generated by lysosomal degradation. Accordingly, intracellular trafficking after internalization has taken place is of essential importance. Studies about the co-localization of the antibody using labels specific for the lysosomal organelle (e.g. surface molecules or small GTPases) allow the selection of antibodies having the desired profile. To this end, target-positive cells ($5\times10^4$/well)

in a total volume of 100 µl were sown into a 96-MTP (Greiner bio-one, CELLSTAR, 650 180, U-bottom). Following addition of the CypHer5E-labelled anti-target antibody (final concentration 20 µg/ml), the batches (duplicates per point in time) were incubated at 37° C. for 30 min, 2 h and 6 h in an incubator (5% $CO_2$). 30 min prior to the end of the chosen incubation time, the lysosome-specific label was added to the batches to be examined. The lysosomes were stained with CytoPainter LysoGreen indicator reagent (final concentration 1:2000; abcam, ab176826). After incubation, 200 µl of ice-cold FACS buffer (DULBECCO'S PBS, Sigma-Aldrich, No. D8537+3% FBS heat inactivated FBS, Gibco, No. 10500-064) were added and the cell suspension was centrifuged at 400×g and 4° C. for 5 min. The cell pellet was resuspended in 300 µl ice-cold FACS buffer and centrifuged again (4 min, 400×g at 4° C.). After centrifugation, the supernatant was discarded and the cell pellet was taken up in 30 µl of ice-cold FACS buffer. The samples were then immediately subjected to FACS/image analysis (FlowSight amnis, Millipore). Co-localization was evaluated using a special software (co-localization software IDEAS Application v6.1). Table 3 summarizes the results from this assay for examples of the anti-CD123 antibodies.

TABLE 3

| Example | Co-localization [%] |
|---|---|
| TPP-9476 | 29 |
| TPP-8997 | 28 |
| TPP-8988 | 41 |
| 7G3 | 10 |
| Isotype control | 0.2 |

The antibodies TPP-8987 and TPP-9476 exhibit a markedly improved profile compared to the parental murine antibody.

C-3 In Vitro Tests for Determining Cell Permeability

The cell permeability of a substance can be investigated by means of in vitro testing in a flux assay using Caco-2 cells [M. D. Troutman and D. R. Thakker, *Pharm. Res.* 20 (8), 1210-1224 (2003)]. For this purpose, the cells were cultured for 15-16 days on 24-well filter plates. For the determination of permeation, the respective test substance was applied in a HEPES buffer to the cells either apically (A) or basally (B) and incubated for 2 hours. After 0 hours and after 2 hours, samples were taken from the cis and trans compartments. The samples were separated by HPLC (Agilent 1200, Böblingen, Germany) using reverse phase columns. The HPLC system was coupled via a Turbo Ion Spray Interface to a Triple Quadropole mass spectrometer API 4000 (AB SCIEX Deutschland GmbH, Darmstadt, Germany). The permeability was evaluated on the basis of a $P_{app}$ value, which was calculated using the formula published by Schwab et al. [D. Schwab et al., *J. Med. Chem.* 46, 1716-1725 (2003)]. A substance was classified as actively transported when the ratio of $P_{app}$ (B-A) to $P_{app}$ (A-B) (efflux ratio) was >2 or <0.5.

Of critical importance for toxophores which are released intracellularly is the permeability from B to A [$P_{app}$ (B-A)] and the ratio of $P_{app}$ (B-A) to $P_{app}$ (A-B) (efflux ratio): The lower this permeability, the slower the active and passive transport processes of the substance through the monolayer of Caco-2 cells. If the efflux ratio, moreover, gives no indications as to active transport, the substance, following intracellular release, can remain in the cell for longer. As a consequence, the time available for interaction with the biochemical target (here: kinesin spindle protein KSP/Eg5) also increases.

Table 4 below sets out permeability data for representative working examples from this assay:

TABLE 4

| Working Example | $P_{app}$ (B-A) [nm/s] | Efflux ratio |
|---|---|---|
| M1 | 1.2 | 0.8 |
| M2 | 1.1 | 1.6 |
| Rm1 | 13.0 | 9.6 |
| Rm2 | 13.2 | 11.9 |

The metabolites M1 and M2, which can be formed from the ADCs according to the invention in Example 1, exhibit both reduced transport from the cell and a reduced efflux ratio compared with the reference metabolites RM1 and RM2, which are formed from the ADC in Reference Example 1.

C-4 In Vitro Tests for Determining the Substrate Properties for P-Glycoprotein (P-gp)

Many tumour cells express transporter proteins for drugs, and this frequently accompanies the development of resistance towards cytostatics. Substances which are not substrates of such transporter proteins, such as P-glycoprotein (P-gp) or BCRP, for example, could therefore exhibit an improved activity profile.

The substrate properties of a substance for P-gp (ABCB1) were determined by means of a flux assay using LLC-PK1 cells which overexpress P-gp (L-MDR1 cells) [A. H. Schinkel et al., *J. Clin. Invest.* 96, 1698-1705 (1995)]. For this purpose, the LLC-PK1 cells or L-MDR1 cells were cultured on 96-well filter plates for 3-4 days. For determination of the permeation, the respective test substance, alone or in the presence of an inhibitor (such as ivermectin or verapamil, for example), was applied in a HEPES buffer to the cells either apically (A) or basally (B) and incubated for 2 hours. After 0 hours and after 2 hours, samples were taken from the cis and trans compartments. The samples were separated by HPLC using reverse phase columns. The HPLC system was coupled via a Turbo Ion Spray Interface to an API 3000 triple quadropole mass spectrometer (Applied Biosystems Applera, Darmstadt, Germany). The permeability was evaluated on the basis of a $P_{app}$ value, which was calculated using the formula published by Schwab et al. [D. Schwab et al., *J. Med. Chem.* 46, 1716-1725 (2003)]. A substance was classified as P-gp substrate when the efflux ratio of $P_{app}$ (B-A) to $P_{app}$ (A-B) was >2.

As further criteria for the evaluation of the P-gp substrate properties, the efflux ratios in L-MDR1 and LLC-PK1 cells or the efflux ratio in the presence or absence of an inhibitor may be compared. If these values differ by a factor of more than 2, the substance in question is a P-gp substrate.

C-5a: Identification of the ADC Metabolites after Internalization In Vitro

Description of the Method:

Internalization studies with immunoconjugates were carried out to analyse metabolites formed intracellularly. To this end, human lung tumour cells NCI H292 ($3\times10^5$/well) were sown in 6-well plates and incubated overnight (37° C., 5% $CO_2$). The cells were treated with 10 µg/ml (66 nM) of the ADC to be examined. Internalization was carried out at 37° C. and 5% $CO_2$. Cell samples were taken for further analysis at various times (0, 4, 24, 48, 72 h). First of all, the supernatants (about 5 ml) were harvested and, after centrifugation (2 min, RT, 1000 rpm Heraeus Variofuge 3.0R), stored at −80° C. The cells were washed with PBS and detached with Accutase, and the cell number was determined. After another washing, a defined number of cells ($2\times10^5$) was treated with 100 ml of lysis buffer (Mammalian Cell Lysis Kit (Sigma MCL1) and incubated with continuous shaking (Thermomixer, 15 min, 4° C., 650 rpm) in Protein LoBind tubes (Eppendorf Cat. No. 0030 108.116). After the incubation, the lysate was centrifuged (10 min, 4° C., 12000 g, eppendorf 5415R) and the supernatant was harvested. The supernatant obtained was stored at −80° C. All samples were then analysed as follows.

The compounds in the culture supernatant or cell lysate were analysed after precipitation of the proteins with methanol or acetonitrile by high-pressure liquid chromatography (HPLC) coupled to a triple-quadrupole mass spectrometer (MS).

For workup of 50 μl of culture supernatant/cell lysate, 150 μl of precipitation reagent (methanol) are added and the mixture is shaken for 10 seconds. The precipitation reagent contains an internal standard (ISTD) in a suitable concentration (generally in the range of 20-100 μg/l). After centrifugation at 1881 g for 10 minutes, the supernatant is transferred into an autosampler vial, made up with 300 μl of a buffer matched to the eluent and shaken again and centrifuged at 1881 g for 10 min.

The cell lysate and supernatant samples are finally analysed using the HPLC-coupled AP14200 triple-quadrupole mass spectrometer from AB SCIEX Deutschland GmbH.

For calibration, blank lysate or blank supernatant is admixed with appropriate concentrations (0.1-1000 μg/l). The detection limit (LLOQ) is about 0.2 μg/l.

Quality controls for testing validity contain 4 and 40 μg/l.
C-5b: Identification of the ADC Metabolites In Vivo
Analysis for Quantification of the Potential Metabolites After i.v. administration of 10 mg/kg of different conjugates according to the invention to xenograft mice, it is possible to measure the plasma, tumour, liver, spleen and kidney concentrations of the antibody and any metabolites occurring 24 h after administration of these conjugates. A more detailed description of the methods with respect to xenograft models can be found under C-6. Here, only the concentrations of the metabolites of the conjugates according to the invention are dealt with. The values measured for the metabolites in the matrices mentioned additionally indicate how pronounced the metabolite burden is in plasma, kidney, spleen and liver, compared to the burden in the tumour.

Analysis for Quantification of the Potential Metabolites

The analysis of the compounds in the plasma, tumour, liver, spleen and kidney follows after precipitation of the proteins with generally methanol by high-pressure liquid chromatography (HPLC) coupled to a triple-quadrupole mass spectrometer (MS).

For workup of 50 μl of plasma, 150 μl of precipitation reagent (generally methanol) are added and the mixture is shaken for 10 sec. The precipitation reagent contains an internal standard (ISTD) in a suitable concentration (generally in the range of 20-100 μg/l). After centrifugation at 1881 g for 10 minutes, the supernatant is transferred into an autosampler vial, made up with 300 μl of a buffer matched to the eluent and shaken again.

In the workup of tumour or organ material, the particular material is admixed with 3-20 times the amount of extraction buffer. The extraction buffer contains 50 ml of Tissue Protein Extraction Reagent (Pierce, Rockford, Ill.), two pellets of Complete-Protease-Inhibitor-Cocktail (Roche Diagnostics GmbH, Mannheim, Germany) and phenylmethylsulfonyl fluoride (Sigma, St. Louis, Mo.) in a final concentration of 1 mM. According to the tissue type (hard: tumour; soft:liver, kidney, spleen), the lysis and homogenization programme of the Prescellys 24 lysis and homogenization system (Bertin Technologies) is selected. The homogenized samples are left to stand at 4° C. overnight. 50 μl of the homogenizate are transferred into an autosampler vial and made up with 150 μl of methanol including ISTD, agitated for 10 sec and then left to stand for 5 min. After adding 300 μl of ammonium acetate buffer (pH 6.8) and agitating briefly, the sample is centrifuged at 1881 g for 10 minutes.

For calibration, plasma for plasma samples and corresponding blank matrix for tissue samples is admixed with concentrations of 0.6-1000 μg/l. According to the sample type or tissue type, the detection limit (LOQ) is between 1 and 20 μg/l.

The plasma and matrix samples are finally analysed using the HPLC-coupled AP14200 triple-quadrupole mass spectrometer from AB SCIEX Deutschland GmbH.

Quality controls for testing validity contain 4, 40 and 400 μg/l.

Table 5: Concentrations of metabolite M1 in tumour, liver, kidney, spleen and plasma 24 h after single 10 mg/kg i.v. administration of Example 1x-9024 in comparison to isotype control in REC-1 xenograft nunu mice.

TABLE 5

| Example | Tissue | Example M1 Mean (μg/l) | Example M1 SD (μg/l) | LLOQ (μg/l) |
|---|---|---|---|---|
| Isotype control | | | | |
| | Tumour | 54.2 | 0.7 | 20.0 |
| | Liver | 26.1 | 1.2 | 4.0 |
| | Kidney | 93.3 | 9.3 | 10.0 |
| | Spleen | 31.5 | 2.4 | 10.0 |
| | Plasma | 4.2 | 0.8 | 1.0 |
| 1x-9024 | | | | |
| | Tumour | 186.4 | 32.4 | 20.0 |
| | Liver | 19.8 | 3.6 | 4.0 |
| | Kidney | 28.0 | 7.0 | 10.0 |
| | Spleen | 20.3 | 6.3 | 10.0 |
| | Plasma | 2.9 | 0.9 | 1.0 |

C-6 Activity Test In Vivo

The activity of the conjugates according to the invention can be tested in vivo, for example, using xenograft models. The person skilled in the art is familiar with methods in the prior art which allow the activity of the compounds according to the invention to be tested (see, for example, WO 2005/081711; Polson et al., Cancer Res. 2009 Mar. 15; 69(6):2358-64).

Human tumour cells which express the antigen for the antibody-drug conjugate are inoculated subcutaneously into the flank of immunosuppressed mice, for example NMRi nude or SCID mice. 1-10 million cells are detached from the cell culture, centrifuged and resuspended in medium or medium/matrigel. The cell suspension is injected under the skin of the mouse.

Within a few days, a tumour grows. Treatment is commenced after the tumour is established, at a tumour size of approximately 40 mm$^2$. To examine the effect on larger tumours, treatment may be initiated only at a tumour size of 50-100 mm$^2$.

Treatment with the ADCs is carried out via the intravenous (i.v.) route into the tail vein of the mouse. The ADC is administered in a volume of 5 ml/kg.

The treatment protocol depends on the pharmacokinetics of the antibody conjugate. Treatment was effected three times in succession every seventh day as the standard. For a quick assessment, a protocol with a single treatment may also be suitable. However, the treatment may also be continued, or a second cycle of further treatment days may follow at a later time.

As standard, 8 animals are used per treatment group. In addition to the groups to which the active substances are administered, one group is treated as control group only with the buffer or isotonic salt solution, according to the same protocol.

During the experiment, the tumour area is measured regularly in two dimensions (length/width) using a caliper. The tumour area is determined as length×width. The ratio of the mean tumour area of the treatment group to that of the control group is stated as T/C area.

When, after the end of the treatment, all groups of the experiment are terminated at the same time, the tumours can be removed and weighed. The ratio of the mean tumour weights of the treatment group to that of the control group is stated as T/C weight.

C-6a. Growth Inhibition/Regression of Experimental Tumours in the Mouse

The tumour cells (REC-1, MOLM-13 or MV-4-11) are inoculated subcutaneously into the flank of female NMRI-nude mice (Janvier). At a tumour size of 40-50 $mm^2$, intravenous treatment is effected with the antibody-drug conjugate once a week for two or three weeks.

The treatment with the ADCs according to the invention leads to a distinct inhibition of tumour growth compared to the control group. Table 6 shows the T/C values determined for tumour area on the respective day of the end of the experiment, calculated from the start of treatment.

TABLE 6

| Example | Tumour model | Dose | Dose scheme | T/C area |
|---------|--------------|------|-------------|----------|
| R1x-9024 | REC1 | 10 mg/kg | Q7d × 3 | 0.48 (day 23) |
| 1x-9024 |  |  |  | 0.19 (day 23) |
| 1x-9024 | REC1 | 10 mg/kg | Q7d × 3 | 0.22 (day 24) |
| 1x-9574 |  |  |  | 0.20 (day 24) |
| 1c-8988 | MV-4-11 | 5 mg/kg | Q7d × 2 | 0.16 (day 20) |
| 1c-9476 |  |  |  | 0.21 (day 20) |
| 1c-8988 | MOLM-13 | 5 mg/kg | Q7d × 2 | 0.33 (day 14) |
| 1c-9476 |  |  |  | 0.5 (day 14) |
| 1c-8987 |  |  |  | 0.35 (day 14) |

The invention claimed is:

1. An antibody-drug conjugate (ADC) of formula (I):

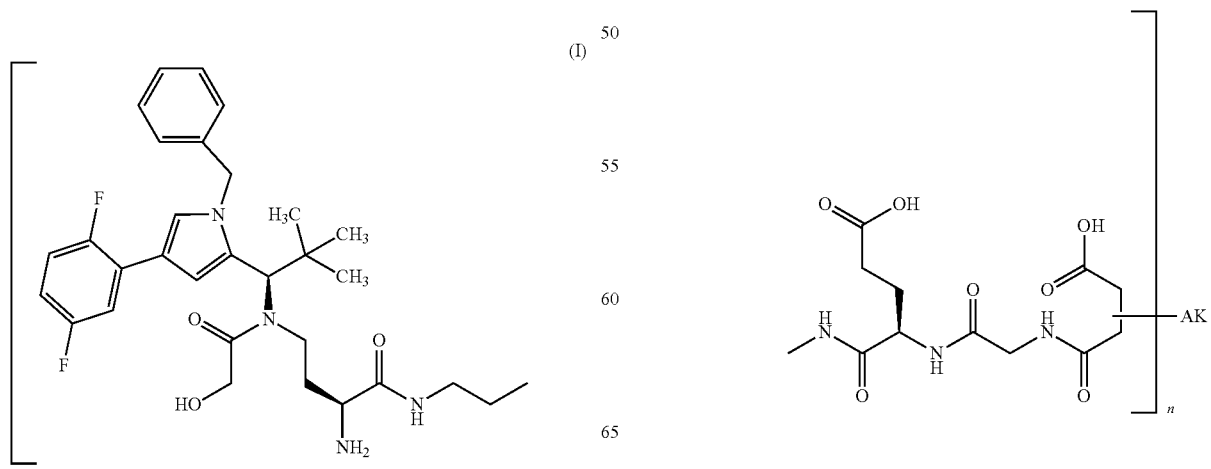

or a salt, a solvate, or a salt of the solvate thereof;

wherein:

n is 1 to 8;

AK is an anti-CD123 antibody comprising a variable region of the heavy chain (VH) comprising the variable CDR1 sequence of the heavy chain (H-CDR1), as shown by SEQ ID NO: 12, the variable CDR2 sequence of the heavy chain (H CDR2), as shown by SEQ ID NO: 13 and the variable CDR3 sequence of the heavy chain (H-CDR3), as shown by SEQ ID NO: 14, and a variable region of the light chain (VL) comprising the variable CDR1 sequence of the light chain (L CDR1), as shown by SEQ ID NO: 16, the variable CDR2 sequence of the light chain (L-CDR2), as shown by SEQ ID NO: 17 and the variable CDR3 sequence of the light chain (L-CDR3), as shown by SEQ ID NO: 18, or is an antigen-binding fragment thereof, wherein the antibody or the antigen-binding fragment thereof is attached via a sulfur atom of a cysteine side group.

2. The antibody-drug conjugate according to claim 1, or a salt, a solvate, or a salt of the solvate thereof, wherein n is 2 to 8.

3. The antibody-drug conjugate according to claim 1, or a salt, a solvate or a salt of the solvate thereof wherein n is 4 to 8.

4. The antibody-drug conjugate according to claim 1, or a salt, a solvate, or a salt of the solvate thereof, wherein AK is an anti-CD123 antibody comprising a variable region of the heavy chain (VH) as shown in SEQ ID NO: 11 and a variable region of the light chain (VL) as shown in SEQ ID NO: 15, or is an antigen-binding fragment thereof.

5. The antibody-drug conjugate according to claim 1, or a salt, a solvate, or a salt of the solvate thereof, wherein AK is an anti-CD123 antibody comprising a region of the heavy chain as shown in SEQ ID NO: 19 and a region of the light chain as shown in SEQ ID NO: 20, or is an antigen-binding fragment thereof.

6. A pharmaceutical composition comprising at least one antibody-drug conjugate (ADC) according to claim 1, or a salt, a solvate, or a salt of the solvate thereof, in combination with an inert, non-toxic, pharmaceutically suitable auxiliary.

7. A method for treatment of hyperproliferative and/or angiogenic disorders which overexpress CD123 or CXCR5, comprising administering to a patient in need thereof an effective amount of an antibody-drug conjugate according to claim 1, or a salt, a solvate, or a salt of the solvate thereof.

8. A method for treatment of cancer and tumours which overexpress CD123 or CXCR5, comprising administering to a human in need thereof an effective amount of an antibody-drug conjugate according to claim 1, or a salt, a solvate, or a salt of the solvate thereof.

9. A method for treatment of cancer and tumours which overexpress CD123 or CXCR5, comprising administering to a human in need thereof an effective amount of an antibody-drug conjugate according to claim 1, or a salt, a solvate, or a salt of the solvate thereof, in combination with one or more therapeutic approaches for cancer immunotherapy or with one or more active compounds directed against a molecular target of cancer immunotherapy.

* * * * *

SEQUENCE LISTING

```
<160> NUMBER OF SEQ ID NOS: 62

<210> SEQ ID NO 1
<211> LENGTH: 120
<212> TYPE: PRT
<213> ORGANISM: Artificial Sequence
<220> FEATURE:
<223> OTHER INFORMATION: Antibody Sequence

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Asp Ile Ile Pro Ser Asn Gly Ala Thr Phe Tyr Asn Gln Lys Phe
    50                  55                  60

Lys Gly Gln Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser
        115                 120

<210> SEQ ID NO 2
<211> LENGTH: 5
<212> TYPE: PRT
<213> ORGANISM: Artificial Sequence
<220> FEATURE:
<223> OTHER INFORMATION: Antibody Sequence

<400> SEQUENCE: 2
```

```
Asp Tyr Tyr Met Lys
1               5

<210> SEQ ID NO 3
<211> LENGTH: 17
<212> TYPE: PRT
<213> ORGANISM: Artificial Sequence
<220> FEATURE:
<223> OTHER INFORMATION: Antibody Sequence

<400> SEQUENCE: 3

Asp Ile Ile Pro Ser Asn Gly Ala Thr Phe Tyr Asn Gln Lys Phe Lys
1               5                   10                  15

Gly

<210> SEQ ID NO 4
<211> LENGTH: 11
<212> TYPE: PRT
<213> ORGANISM: Artificial Sequence
<220> FEATURE:
<223> OTHER INFORMATION: Antibody Sequence

<400> SEQUENCE: 4

Ser His Leu Leu Arg Ala Ser Trp Phe Ala Tyr
1               5                   10

<210> SEQ ID NO 5
<211> LENGTH: 113
<212> TYPE: PRT
<213> ORGANISM: Artificial Sequence
<220> FEATURE:
<223> OTHER INFORMATION: Antibody Sequence

<400> SEQUENCE: 5

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Val Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 6
<211> LENGTH: 17
<212> TYPE: PRT
<213> ORGANISM: Artificial Sequence
<220> FEATURE:
<223> OTHER INFORMATION: Antibody Sequence

<400> SEQUENCE: 6

Glu Ser Ser Gln Ser Val Leu Asn Ser Gly Asn Gln Lys Asn Tyr Leu
1               5                   10                  15

Thr
```

```
<210> SEQ ID NO 7
<211> LENGTH: 7
<212> TYPE: PRT
<213> ORGANISM: Artificial Sequence
<220> FEATURE:
<223> OTHER INFORMATION: Antibody Sequence

<400> SEQUENCE: 7

Trp Ala Ser Thr Arg Glu Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Antibody Sequence

<400> SEQUENCE: 8

Gln Asn Asp Tyr Ser Tyr Pro Tyr Thr
1               5

<210> SEQ ID NO 9
<211> LENGTH: 449
<212> TYPE: PRT
<213> ORGANISM: Artificial Sequence
<220> FEATURE:
<223> OTHER INFORMATION: Antibody Sequence

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Asp Ile Ile Pro Ser Asn Gly Ala Thr Phe Tyr Asn Gln Lys Phe
    50                  55                  60

Lys Gly Gln Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
```

```
                225                 230                 235                 240
        Pro Ser Val Phe Leu Phe Pro Lys Pro Lys Asp Thr Leu Met Ile
                        245                 250                 255

Ser Arg Thr Pro Glu Val Thr Cys Val Val Asp Val Ser His Glu
                        260                 265                 270

Asp Pro Glu Val Lys Phe Asn Trp Tyr Val Asp Gly Val Glu Val His
                        275                 280                 285

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
        305                 310                 315                 320

Glu Tyr Lys Cys Lys Val Ser Asn Lys Ala Leu Pro Ala Pro Ile Glu
                        325                 330                 335

Lys Thr Ile Ser Lys Ala Lys Gly Gln Pro Arg Glu Pro Gln Val Tyr
                        340                 345                 350

Thr Leu Pro Pro Ser Arg Asp Glu Leu Thr Lys Asn Gln Val Ser Leu
                        355                 360                 365

Thr Cys Leu Val Lys Gly Phe Tyr Pro Ser Asp Ile Ala Val Glu Trp
                        370                 375                 380

Glu Ser Asn Gly Gln Pro Glu Asn Asn Tyr Lys Thr Thr Pro Pro Val
        385                 390                 395                 400

Leu Asp Ser Asp Gly Ser Phe Phe Leu Tyr Ser Lys Leu Thr Val Asp
                        405                 410                 415

Lys Ser Arg Trp Gln Gln Gly Asn Val Phe Ser Cys Ser Val Met His
                        420                 425                 430

Glu Ala Leu His Asn His Tyr Thr Gln Lys Ser Leu Ser Leu Ser Pro
                        435                 440                 445

Gly

<210> SEQ ID NO 10
<211> LENGTH: 220
<212> TYPE: PRT
<213> ORGANISM: Artificial Sequence
<220> FEATURE:
<223> OTHER INFORMATION: Antibody Sequence

<400> SEQUENCE: 10

Asp Ile Val Met Thr Gln Ser Pro Asp Ser Leu Ala Val Ser Leu Gly
        1               5                   10                  15

Glu Arg Ala Thr Ile Asn Cys Glu Ser Ser Gln Ser Val Leu Asn Ser
                        20                  25                  30

Gly Asn Gln Lys Asn Tyr Leu Thr Trp Tyr Gln Gln Lys Pro Gly Gln
                    35                  40                  45

Pro Pro Lys Leu Leu Ile Tyr Trp Ala Ser Thr Arg Glu Ser Gly Val
            50                  55                  60

Pro Asp Arg Phe Ser Gly Ser Gly Ser Gly Thr Asp Phe Thr Leu Thr
        65                  70                  75                  80

Ile Ser Ser Leu Gln Ala Glu Asp Val Ala Val Tyr Tyr Cys Gln Asn
                        85                  90                  95

Asp Tyr Ser Tyr Pro Tyr Thr Phe Gly Gln Gly Thr Lys Leu Glu Ile
                        100                 105                 110

Lys Arg Thr Val Ala Ala Pro Ser Val Phe Ile Phe Pro Pro Ser Asp
                    115                 120                 125

Glu Gln Leu Lys Ser Gly Thr Ala Ser Val Val Cys Leu Leu Asn Asn
                130                 135                 140
```

```
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
        180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220

<210> SEQ ID NO 11
<211> LENGTH: 118
<212> TYPE: PRT
<213> ORGANISM: Artificial Sequence
<220> FEATURE:
<223> OTHER INFORMATION: Antibody Sequence

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115

<210> SEQ ID NO 12
<211> LENGTH: 6
<212> TYPE: PRT
<213> ORGANISM: Artificial Sequence
<220> FEATURE:
<223> OTHER INFORMATION: Antibody Sequence

<400> SEQUENCE: 12

Ser Gly Tyr Tyr Trp Asn
1               5

<210> SEQ ID NO 13
<211> LENGTH: 17
<212> TYPE: PRT
<213> ORGANISM: Artificial Sequence
<220> FEATURE:
<223> OTHER INFORMATION: Antibody Sequence

<400> SEQUENCE: 13

Tyr Ile Ser Tyr Asp Gly Ser Asn Asn Tyr Asn Pro Ser Leu Lys Asn
1               5                   10                  15

Gly
```

```
<210> SEQ ID NO 14
<211> LENGTH: 8
<212> TYPE: PRT
<213> ORGANISM: Artificial Sequence
<220> FEATURE:
<223> OTHER INFORMATION: Antibody Sequence

<400> SEQUENCE: 14

Gly Glu Gly Phe Tyr Phe Asp Ser
1               5

<210> SEQ ID NO 15
<211> LENGTH: 113
<212> TYPE: PRT
<213> ORGANISM: Artificial Sequence
<220> FEATURE:
<223> OTHER INFORMATION: Antibody Sequence

<400> SEQUENCE: 15

Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser Thr Gln Lys Asn Tyr Leu Ala Trp Tyr Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
                100                 105                 110

Lys

<210> SEQ ID NO 16
<211> LENGTH: 17
<212> TYPE: PRT
<213> ORGANISM: Artificial Sequence
<220> FEATURE:
<223> OTHER INFORMATION: Antibody Sequence

<400> SEQUENCE: 16

Lys Ser Ser Gln Ser Leu Phe Phe Gly Ser Thr Gln Lys Asn Tyr Leu
1               5                   10                  15

Ala

<210> SEQ ID NO 17
<211> LENGTH: 7
<212> TYPE: PRT
<213> ORGANISM: Artificial Sequence
<220> FEATURE:
<223> OTHER INFORMATION: Antibody Sequence

<400> SEQUENCE: 17

Trp Ala Ser Thr Arg Glu Ser
1               5

<210> SEQ ID NO 18
<211> LENGTH: 9
<212> TYPE: PRT
<213> ORGANISM: Artificial Sequence
<220> FEATURE:
```

<223> OTHER INFORMATION: Antibody Sequence

<400> SEQUENCE: 18

Gln Gln Tyr Tyr Asn Tyr Pro Trp Thr
1               5

<210> SEQ ID NO 19
<211> LENGTH: 447
<212> TYPE: PRT
<213> ORGANISM: Artificial Sequence
<220> FEATURE:
<223> OTHER INFORMATION: Antibody Sequence

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

```
Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 20
<211> LENGTH: 220
<212> TYPE: PRT
<213> ORGANISM: Artificial Sequence
<220> FEATURE:
<223> OTHER INFORMATION: Antibody Sequence

<400> SEQUENCE: 20

Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 21
<211> LENGTH: 113
<212> TYPE: PRT
<213> ORGANISM: Artificial Sequence
```

<220> FEATURE:
<223> OTHER INFORMATION: Antibody Sequence

<400> SEQUENCE: 21

Glu Val Gln Leu Val Glu Ser Gly Gly Gly Leu Val Gln Pro Gly Lys
1               5                   10                  15

Ser Leu Lys Leu Ser Cys Ser Ala Ser Gly Phe Thr Phe Ser Thr Ser
            20                  25                  30

Gly Met His Trp Phe Arg Gln Ala Pro Gly Lys Gly Leu Asp Trp Val
        35                  40                  45

Ala Tyr Ile Ser Ser Ser Gly Phe Val Tyr Ala Asp Ala Val Lys
    50                  55                  60

Gly Arg Phe Thr Ile Ser Arg Asp Asn Ala Gln Asn Thr Leu Tyr Leu
65                  70                  75                  80

Gln Leu Asn Ser Leu Lys Ser Glu Asp Thr Ala Ile Tyr Tyr Cys Ala
                85                  90                  95

Arg Ser Glu Ala Ala Phe Trp Gly Gln Gly Thr Leu Val Thr Val Ser
            100                 105                 110

Ser

<210> SEQ ID NO 22
<211> LENGTH: 5
<212> TYPE: PRT
<213> ORGANISM: Artificial Sequence
<220> FEATURE:
<223> OTHER INFORMATION: Antibody Sequence

<400> SEQUENCE: 22

Thr Ser Gly Met His
1               5

<210> SEQ ID NO 23
<211> LENGTH: 16
<212> TYPE: PRT
<213> ORGANISM: Artificial Sequence
<220> FEATURE:
<223> OTHER INFORMATION: Antibody Sequence

<400> SEQUENCE: 23

Tyr Ile Ser Ser Ser Gly Phe Val Tyr Ala Asp Ala Val Lys Gly
1               5                   10                  15

<210> SEQ ID NO 24
<211> LENGTH: 5
<212> TYPE: PRT
<213> ORGANISM: Artificial Sequence
<220> FEATURE:
<223> OTHER INFORMATION: Antibody Sequence

<400> SEQUENCE: 24

Ser Glu Ala Ala Phe
1               5

<210> SEQ ID NO 25
<211> LENGTH: 112
<212> TYPE: PRT
<213> ORGANISM: Artificial Sequence
<220> FEATURE:
<223> OTHER INFORMATION: Antibody Sequence

<400> SEQUENCE: 25

Asp Ile Val Leu Thr Gln Ala Pro Arg Ser Val Ser Val Thr Pro Gly
1               5                   10                  15

-continued

```
Glu Ser Ala Ser Ile Ser Cys Arg Ser Asn Lys Ser Arg Leu Ser Arg
            20                  25                  30

Met Gly Ile Thr Pro Leu Asn Trp Tyr Leu Gln Lys Pro Gly Lys Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Glu Thr Asp Phe Thr Leu Lys Ile
65                  70                  75                  80

Ser Lys Val Glu Thr Glu Asp Val Gly Val Tyr Tyr Cys Ala Gln Phe
                85                  90                  95

Leu Glu Tyr Pro Pro Thr Phe Gly Ser Gly Thr Lys Leu Glu Ile Lys
            100                 105                 110

<210> SEQ ID NO 26
<211> LENGTH: 16
<212> TYPE: PRT
<213> ORGANISM: Artificial Sequence
<220> FEATURE:
<223> OTHER INFORMATION: Antibody Sequence

<400> SEQUENCE: 26

Arg Ser Asn Lys Ser Arg Leu Ser Arg Met Gly Ile Thr Pro Leu Asn
1               5                   10                  15

<210> SEQ ID NO 27
<211> LENGTH: 7
<212> TYPE: PRT
<213> ORGANISM: Artificial Sequence
<220> FEATURE:
<223> OTHER INFORMATION: Antibody Sequence

<400> SEQUENCE: 27

Arg Met Ser Asn Leu Ala Ser
1               5

<210> SEQ ID NO 28
<211> LENGTH: 9
<212> TYPE: PRT
<213> ORGANISM: Artificial Sequence
<220> FEATURE:
<223> OTHER INFORMATION: Antibody Sequence

<400> SEQUENCE: 28

Ala Gln Phe Leu Glu Tyr Pro Pro Thr
1               5

<210> SEQ ID NO 29
<211> LENGTH: 442
<212> TYPE: PRT
<213> ORGANISM: Artificial Sequence
<220> FEATURE:
<223> OTHER INFORMATION: Antibody Sequence

<400> SEQUENCE: 29

Glu Val Gln Leu Val Glu Ser Gly Gly Gly Leu Val Gln Pro Gly Lys
1               5                   10                  15

Ser Leu Lys Leu Ser Cys Ser Ala Ser Gly Phe Thr Phe Ser Thr Ser
            20                  25                  30

Gly Met His Trp Phe Arg Gln Ala Pro Gly Lys Gly Leu Asp Trp Val
        35                  40                  45

Ala Tyr Ile Ser Ser Ser Ser Gly Phe Val Tyr Ala Asp Ala Val Lys
    50                  55                  60
```

Gly Arg Phe Thr Ile Ser Arg Asp Asn Ala Gln Asn Thr Leu Tyr Leu
65                  70                  75                  80

Gln Leu Asn Ser Leu Lys Ser Glu Asp Thr Ala Ile Tyr Tyr Cys Ala
            85                  90                  95

Arg Ser Glu Ala Ala Phe Trp Gly Gln Gly Thr Leu Val Thr Val Ser
        100                 105                 110

Ser Ala Ser Thr Lys Gly Pro Ser Val Phe Pro Leu Ala Pro Ser Ser
    115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly
        435                 440

<210> SEQ ID NO 30
<211> LENGTH: 219
<212> TYPE: PRT
<213> ORGANISM: Artificial Sequence
<220> FEATURE:

<223> OTHER INFORMATION: Antibody Sequence

<400> SEQUENCE: 30

Asp Ile Val Leu Thr Gln Ala Pro Arg Ser Val Ser Val Thr Pro Gly
1               5                   10                  15

Glu Ser Ala Ser Ile Ser Cys Arg Ser Asn Lys Ser Arg Leu Ser Arg
            20                  25                  30

Met Gly Ile Thr Pro Leu Asn Trp Tyr Leu Gln Lys Pro Gly Lys Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Glu Thr Asp Phe Thr Leu Lys Ile
65                  70                  75                  80

Ser Lys Val Glu Thr Glu Asp Val Gly Val Tyr Tyr Cys Ala Gln Phe
                85                  90                  95

Leu Glu Tyr Pro Pro Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 31
<211> LENGTH: 120
<212> TYPE: PRT
<213> ORGANISM: Artificial Sequence
<220> FEATURE:
<223> OTHER INFORMATION: Antibody Sequence

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met Lys Trp Val Arg Gln Ala Pro Gly Gln Gly Leu Glu Trp Met
        35                  40                  45

Gly Asp Ile Ile Pro Ser Asn Gly Ala Thr Phe Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser
        115                 120

```
<210> SEQ ID NO 32
<211> LENGTH: 5
<212> TYPE: PRT
<213> ORGANISM: Artificial Sequence
<220> FEATURE:
<223> OTHER INFORMATION: Antibody Sequence

<400> SEQUENCE: 32

Asp Tyr Tyr Met Lys
1               5

<210> SEQ ID NO 33
<211> LENGTH: 17
<212> TYPE: PRT
<213> ORGANISM: Artificial Sequence
<220> FEATURE:
<223> OTHER INFORMATION: Antibody Sequence

<400> SEQUENCE: 33

Asp Ile Ile Pro Ser Asn Gly Ala Thr Phe Tyr Asn Gln Lys Phe Lys
1               5                   10                  15

Gly

<210> SEQ ID NO 34
<211> LENGTH: 11
<212> TYPE: PRT
<213> ORGANISM: Artificial Sequence
<220> FEATURE:
<223> OTHER INFORMATION: Antibody Sequence

<400> SEQUENCE: 34

Ser His Leu Leu Arg Ala Ser Trp Phe Ala Tyr
1               5                   10

<210> SEQ ID NO 35
<211> LENGTH: 113
<212> TYPE: PRT
<213> ORGANISM: Artificial Sequence
<220> FEATURE:
<223> OTHER INFORMATION: Antibody Sequence

<400> SEQUENCE: 35

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Val Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 36
<211> LENGTH: 17
<212> TYPE: PRT
```

```
<213> ORGANISM: Artificial Sequence
<220> FEATURE:
<223> OTHER INFORMATION: Antibody Sequence

<400> SEQUENCE: 36

Glu Ser Ser Gln Ser Val Leu Asn Ser Gly Asn Gln Lys Asn Tyr Leu
1               5                   10                  15

Thr

<210> SEQ ID NO 37
<211> LENGTH: 7
<212> TYPE: PRT
<213> ORGANISM: Artificial Sequence
<220> FEATURE:
<223> OTHER INFORMATION: Antibody Sequence

<400> SEQUENCE: 37

Trp Ala Ser Thr Arg Glu Ser
1               5

<210> SEQ ID NO 38
<211> LENGTH: 9
<212> TYPE: PRT
<213> ORGANISM: Artificial Sequence
<220> FEATURE:
<223> OTHER INFORMATION: Antibody Sequence

<400> SEQUENCE: 38

Gln Asn Asp Tyr Ser Tyr Pro Tyr Thr
1               5

<210> SEQ ID NO 39
<211> LENGTH: 449
<212> TYPE: PRT
<213> ORGANISM: Artificial Sequence
<220> FEATURE:
<223> OTHER INFORMATION: Antibody Sequence

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
                20                  25                  30

Tyr Met Lys Trp Val Arg Gln Ala Pro Gly Gln Gly Leu Glu Trp Met
            35                  40                  45

Gly Asp Ile Ile Pro Ser Asn Gly Ala Thr Phe Tyr Asn Gln Lys Phe
        50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 40
<211> LENGTH: 220
<212> TYPE: PRT
<213> ORGANISM: Artificial Sequence
<220> FEATURE:
<223> OTHER INFORMATION: Antibody Sequence

<400> SEQUENCE: 40

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Val Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
            85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 41
<211> LENGTH: 113
<212> TYPE: PRT
<213> ORGANISM: Artificial Sequence
<220> FEATURE:
<223> OTHER INFORMATION: Antibody Sequence

<400> SEQUENCE: 41

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Phe Ser Thr Ser
            20                  25                  30

Gly Met His Trp Phe Arg Gln Ala Pro Gly Lys Gly Leu Glu Trp Val
            35                  40                  45

Ala Tyr Ile Ser Ser Ser Gly Phe Val Tyr Ala Asp Ala Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Ser Glu Ala Ala Phe Trp Gly Gln Gly Thr Leu Val Thr Val Ser
            100                 105                 110

Ser

<210> SEQ ID NO 42
<211> LENGTH: 5
<212> TYPE: PRT
<213> ORGANISM: Artificial Sequence
<220> FEATURE:
<223> OTHER INFORMATION: Antibody Sequence

<400> SEQUENCE: 42

Thr Ser Gly Met His
1               5

<210> SEQ ID NO 43
<211> LENGTH: 16
<212> TYPE: PRT
<213> ORGANISM: Artificial Sequence
<220> FEATURE:

<223> OTHER INFORMATION: Antibody Sequence

<400> SEQUENCE: 43

Tyr Ile Ser Ser Ser Ser Gly Phe Val Tyr Ala Asp Ala Val Lys Gly
1               5                   10                  15

<210> SEQ ID NO 44
<211> LENGTH: 5
<212> TYPE: PRT
<213> ORGANISM: Artificial Sequence
<220> FEATURE:
<223> OTHER INFORMATION: Antibody Sequence

<400> SEQUENCE: 44

Ser Glu Ala Ala Phe
1               5

<210> SEQ ID NO 45
<211> LENGTH: 112
<212> TYPE: PRT
<213> ORGANISM: Artificial Sequence
<220> FEATURE:
<223> OTHER INFORMATION: Antibody Sequence

<400> SEQUENCE: 45

Asp Ile Val Met Thr Gln Ser Pro Leu Ser Leu Pro Val Thr Pro Gly
1               5                   10                  15

Glu Pro Ala Ser Ile Ser Cys Arg Ser Gln Lys Ser Arg Leu Ser Arg
            20                  25                  30

Met Gly Ile Thr Pro Leu Asn Trp Tyr Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Phe
                85                  90                  95

Leu Glu Tyr Pro Pro Thr Phe Gly Gln Gly Thr Lys Leu Glu Ile Lys
            100                 105                 110

<210> SEQ ID NO 46
<211> LENGTH: 16
<212> TYPE: PRT
<213> ORGANISM: Artificial Sequence
<220> FEATURE:
<223> OTHER INFORMATION: Antibody Sequence

<400> SEQUENCE: 46

Arg Ser Gln Lys Ser Arg Leu Ser Arg Met Gly Ile Thr Pro Leu Asn
1               5                   10                  15

<210> SEQ ID NO 47
<211> LENGTH: 7
<212> TYPE: PRT
<213> ORGANISM: Artificial Sequence
<220> FEATURE:
<223> OTHER INFORMATION: Antibody Sequence

<400> SEQUENCE: 47

Arg Met Ser Asn Leu Ala Ser
1               5

<210> SEQ ID NO 48

```
<211> LENGTH: 9
<212> TYPE: PRT
<213> ORGANISM: Artificial Sequence
<220> FEATURE:
<223> OTHER INFORMATION: Antibody Sequence

<400> SEQUENCE: 48

Ala Gln Phe Leu Glu Tyr Pro Pro Thr
1               5

<210> SEQ ID NO 49
<211> LENGTH: 442
<212> TYPE: PRT
<213> ORGANISM: Artificial Sequence
<220> FEATURE:
<223> OTHER INFORMATION: Antibody Sequence

<400> SEQUENCE: 49

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Phe Ser Thr Ser
                20                  25                  30

Gly Met His Trp Phe Arg Gln Ala Pro Gly Lys Gly Leu Glu Trp Val
            35                  40                  45

Ala Tyr Ile Ser Ser Ser Gly Phe Val Tyr Ala Asp Ala Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ser Glu Ala Ala Phe Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
```

```
            305                 310                 315                 320
Asn Lys Ala Leu Pro Ala Pro Ile Glu Lys Thr Ile Ser Lys Ala Lys
                325                 330                 335
Gly Gln Pro Arg Glu Pro Gln Val Tyr Thr Leu Pro Pro Ser Arg Asp
                340                 345                 350
Glu Leu Thr Lys Asn Gln Val Ser Leu Thr Cys Leu Val Lys Gly Phe
                355                 360                 365
Tyr Pro Ser Asp Ile Ala Val Glu Trp Glu Ser Asn Gly Gln Pro Glu
                370                 375                 380
Asn Asn Tyr Lys Thr Thr Pro Pro Val Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
                420                 425                 430
Thr Gln Lys Ser Leu Ser Leu Ser Pro Gly
                435                 440

<210> SEQ ID NO 50
<211> LENGTH: 219
<212> TYPE: PRT
<213> ORGANISM: Artificial Sequence
<220> FEATURE:
<223> OTHER INFORMATION: Antibody Sequence

<400> SEQUENCE: 50

Asp Ile Val Met Thr Gln Ser Pro Leu Ser Leu Pro Val Thr Pro Gly
1               5                   10                  15
Glu Pro Ala Ser Ile Ser Cys Arg Ser Gln Lys Ser Arg Leu Ser Arg
                20                  25                  30
Met Gly Ile Thr Pro Leu Asn Trp Tyr Leu Gln Lys Pro Gly Gln Ser
                35                  40                  45
Pro Gln Leu Leu Ile Tyr Arg Met Ser Asn Leu Ala Ser Gly Val Pro
            50                  55                  60
Asp Arg Phe Ser Gly Ser Gly Ser Gly Thr Asp Phe Thr Leu Lys Ile
65              70                  75                  80
Ser Arg Val Glu Ala Glu Asp Val Gly Val Tyr Tyr Cys Ala Gln Phe
                85                  90                  95
Leu Glu Tyr Pro Pro Thr Phe Gly Gln Gly Thr Lys Leu Glu Ile Lys
                100                 105                 110
Arg Thr Val Ala Ala Pro Ser Val Phe Ile Phe Pro Pro Ser Asp Glu
                115                 120                 125
Gln Leu Lys Ser Gly Thr Ala Ser Val Val Cys Leu Leu Asn Asn Phe
            130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
                180                 185                 190
Lys His Lys Val Tyr Ala Cys Glu Val Thr His Gln Gly Leu Ser Ser
                195                 200                 205
Pro Val Thr Lys Ser Phe Asn Arg Gly Glu Cys
            210                 215
```

<210> SEQ ID NO 51
<211> LENGTH: 113
<212> TYPE: PRT
<213> ORGANISM: Artificial Sequence
<220> FEATURE:
<223> OTHER INFORMATION: Antibody Sequence

<400> SEQUENCE: 51

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Phe Ser Thr Ser
            20                  25                  30

Gly Met His Trp Val Arg Gln Ala Pro Gly Lys Gly Leu Glu Trp Val
        35                  40                  45

Ser Tyr Ile Ser Ser Ser Ser Gly Phe Val Tyr Ala Asp Ala Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ser Glu Ala Ala Phe Trp Gly Gln Gly Thr Leu Val Thr Val Ser
            100                 105                 110

Ser

<210> SEQ ID NO 52
<211> LENGTH: 5
<212> TYPE: PRT
<213> ORGANISM: Artificial Sequence
<220> FEATURE:
<223> OTHER INFORMATION: Antibody Sequence

<400> SEQUENCE: 52

Thr Ser Gly Met His
1               5

<210> SEQ ID NO 53
<211> LENGTH: 16
<212> TYPE: PRT
<213> ORGANISM: Artificial Sequence
<220> FEATURE:
<223> OTHER INFORMATION: Antibody Sequence

<400> SEQUENCE: 53

Tyr Ile Ser Ser Ser Ser Gly Phe Val Tyr Ala Asp Ala Val Lys Gly
1               5                   10                  15

<210> SEQ ID NO 54
<211> LENGTH: 5
<212> TYPE: PRT
<213> ORGANISM: Artificial Sequence
<220> FEATURE:
<223> OTHER INFORMATION: Antibody Sequence

<400> SEQUENCE: 54

Ser Glu Ala Ala Phe
1               5

<210> SEQ ID NO 55
<211> LENGTH: 112
<212> TYPE: PRT
<213> ORGANISM: Artificial Sequence
<220> FEATURE:
<223> OTHER INFORMATION: Antibody Sequence

<400> SEQUENCE: 55

Asp Ile Val Met Thr Gln Ser Pro Leu Ser Leu Pro Val Thr Pro Gly
1               5                   10                  15

Glu Pro Ala Ser Ile Ser Cys Arg Ser Gln Lys Ser Arg Leu Ser Arg
            20                  25                  30

Met Gly Ile Thr Pro Leu Asn Trp Tyr Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Phe
                85                  90                  95

Leu Glu Tyr Pro Pro Thr Phe Gly Gln Gly Thr Lys Leu Glu Ile Lys
            100                 105                 110

<210> SEQ ID NO 56
<211> LENGTH: 16
<212> TYPE: PRT
<213> ORGANISM: Artificial Sequence
<220> FEATURE:
<223> OTHER INFORMATION: Antibody Sequence

<400> SEQUENCE: 56

Arg Ser Gln Lys Ser Arg Leu Ser Arg Met Gly Ile Thr Pro Leu Asn
1               5                   10                  15

<210> SEQ ID NO 57
<211> LENGTH: 7
<212> TYPE: PRT
<213> ORGANISM: Artificial Sequence
<220> FEATURE:
<223> OTHER INFORMATION: Antibody Sequence

<400> SEQUENCE: 57

Arg Met Ser Asn Leu Ala Ser
1               5

<210> SEQ ID NO 58
<211> LENGTH: 9
<212> TYPE: PRT
<213> ORGANISM: Artificial Sequence
<220> FEATURE:
<223> OTHER INFORMATION: Antibody Sequence

<400> SEQUENCE: 58

Ala Gln Phe Leu Glu Tyr Pro Pro Thr
1               5

<210> SEQ ID NO 59
<211> LENGTH: 442
<212> TYPE: PRT
<213> ORGANISM: Artificial Sequence
<220> FEATURE:
<223> OTHER INFORMATION: Antibody Sequence

<400> SEQUENCE: 59

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Phe Ser Thr Ser
            20                  25                  30

Gly Met His Trp Val Arg Gln Ala Pro Gly Lys Gly Leu Glu Trp Val

```
            35                  40                  45
Ser Tyr Ile Ser Ser Ser Gly Phe Val Tyr Ala Asp Ala Val Lys
 50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Ala
                 85                  90                  95
Arg Ser Glu Ala Ala Phe Trp Gly Gln Gly Thr Leu Val Thr Val Ser
            100                 105                 110
Ser Ala Ser Thr Lys Gly Pro Ser Val Phe Pro Leu Ala Pro Ser Ser
        115                 120                 125
Lys Ser Thr Ser Gly Gly Thr Ala Ala Leu Gly Cys Leu Val Lys Asp
130                 135                 140
Tyr Phe Pro Glu Pro Val Thr Val Ser Trp Asn Ser Gly Ala Leu Thr
145                 150                 155                 160
Ser Gly Val His Thr Phe Pro Ala Val Leu Gln Ser Ser Gly Leu Tyr
                165                 170                 175
Ser Leu Ser Ser Val Val Thr Val Pro Ser Ser Ser Leu Gly Thr Gln
            180                 185                 190
Thr Tyr Ile Cys Asn Val Asn His Lys Pro Ser Asn Thr Lys Val Asp
        195                 200                 205
Lys Lys Val Glu Pro Lys Ser Cys Asp Lys Thr His Thr Cys Pro Pro
210                 215                 220
Cys Pro Ala Pro Glu Leu Leu Gly Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser His Glu Asp Pro Glu Val Lys Phe Asn
            260                 265                 270
Trp Tyr Val Asp Gly Val Glu Val His Asn Ala Lys Thr Lys Pro Arg
        275                 280                 285
Glu Glu Gln Tyr Asn Ser Thr Tyr Arg Val Val Ser Val Leu Thr Val
290                 295                 300
Leu His Gln Asp Trp Leu Asn Gly Lys Glu Tyr Lys Cys Lys Val Ser
305                 310                 315                 320
Asn Lys Ala Leu Pro Ala Pro Ile Glu Lys Thr Ile Ser Lys Ala Lys
                325                 330                 335
Gly Gln Pro Arg Glu Pro Gln Val Tyr Thr Leu Pro Pro Ser Arg Asp
            340                 345                 350
Glu Leu Thr Lys Asn Gln Val Ser Leu Thr Cys Leu Val Lys Gly Phe
        355                 360                 365
Tyr Pro Ser Asp Ile Ala Val Glu Trp Glu Ser Asn Gly Gln Pro Glu
370                 375                 380
Asn Asn Tyr Lys Thr Thr Pro Pro Val Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly
        435                 440

<210> SEQ ID NO 60
```

```
<211> LENGTH: 219
<212> TYPE: PRT
<213> ORGANISM: Artificial Sequence
<220> FEATURE:
<223> OTHER INFORMATION: Antibody Sequence

<400> SEQUENCE: 60

Asp Ile Val Met Thr Gln Ser Pro Leu Ser Leu Pro Val Thr Pro Gly
1               5                   10                  15

Glu Pro Ala Ser Ile Ser Cys Arg Ser Gln Lys Ser Arg Leu Ser Arg
            20                  25                  30

Met Gly Ile Thr Pro Leu Asn Trp Tyr Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Phe
                85                  90                  95

Leu Glu Tyr Pro Pro Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 61
<211> LENGTH: 372
<212> TYPE: PRT
<213> ORGANISM: Homo sapiens

<400> SEQUENCE: 61

Met Asn Tyr Pro Leu Thr Leu Glu Met Asp Leu Glu Asn Leu Glu Asp
1               5                   10                  15

Leu Phe Trp Glu Leu Asp Arg Leu Asp Asn Tyr Asn Asp Thr Ser Leu
            20                  25                  30

Val Glu Asn His Leu Cys Pro Ala Thr Glu Gly Pro Leu Met Ala Ser
        35                  40                  45

Phe Lys Ala Val Phe Val Pro Val Ala Tyr Ser Leu Ile Phe Leu Leu
    50                  55                  60

Gly Val Ile Gly Asn Val Leu Val Leu Val Ile Leu Glu Arg His Arg
65                  70                  75                  80

Gln Thr Arg Ser Ser Thr Glu Thr Phe Leu Phe His Leu Ala Val Ala
                85                  90                  95

Asp Leu Leu Leu Val Phe Ile Leu Pro Phe Ala Val Ala Glu Gly Ser
            100                 105                 110
```

Val Gly Trp Val Leu Gly Thr Phe Leu Cys Lys Thr Val Ile Ala Leu
            115                 120                 125

His Lys Val Asn Phe Tyr Cys Ser Ser Leu Leu Leu Ala Cys Ile Ala
130                 135                 140

Val Asp Arg Tyr Leu Ala Ile Val His Ala Val His Ala Tyr Arg His
145                 150                 155                 160

Arg Arg Leu Leu Ser Ile His Ile Thr Cys Gly Thr Ile Trp Leu Val
                165                 170                 175

Gly Phe Leu Leu Ala Leu Pro Glu Ile Leu Phe Ala Lys Val Ser Gln
                180                 185                 190

Gly His His Asn Asn Ser Leu Pro Arg Cys Thr Phe Ser Gln Glu Asn
                195                 200                 205

Gln Ala Glu Thr His Ala Trp Phe Thr Ser Arg Phe Leu Tyr His Val
            210                 215                 220

Ala Gly Phe Leu Leu Pro Met Leu Val Met Gly Trp Cys Tyr Val Gly
225                 230                 235                 240

Val Val His Arg Leu Arg Gln Ala Gln Arg Arg Pro Gln Arg Gln Lys
                245                 250                 255

Ala Val Arg Val Ala Ile Leu Val Thr Ser Ile Phe Phe Leu Cys Trp
                260                 265                 270

Ser Pro Tyr His Ile Val Ile Phe Leu Asp Thr Leu Ala Arg Leu Lys
                275                 280                 285

Ala Val Asp Asn Thr Cys Lys Leu Asn Gly Ser Leu Pro Val Ala Ile
            290                 295                 300

Thr Met Cys Glu Phe Leu Gly Leu Ala His Cys Cys Leu Asn Pro Met
305                 310                 315                 320

Leu Tyr Thr Phe Ala Gly Val Lys Phe Arg Ser Asp Leu Ser Arg Leu
                325                 330                 335

Leu Thr Lys Leu Gly Cys Thr Gly Pro Ala Ser Leu Cys Gln Leu Phe
                340                 345                 350

Pro Ser Trp Arg Arg Ser Ser Leu Ser Glu Ser Glu Asn Ala Thr Ser
                355                 360                 365

Leu Thr Thr Phe
    370

<210> SEQ ID NO 62
<211> LENGTH: 378
<212> TYPE: PRT
<213> ORGANISM: Homo sapiens

<400> SEQUENCE: 62

Met Val Leu Leu Trp Leu Thr Leu Leu Leu Ile Ala Leu Pro Cys Leu
1               5                   10                  15

Leu Gln Thr Lys Glu Asp Pro Asn Pro Ile Thr Asn Leu Arg Met
                20                  25                  30

Lys Ala Lys Ala Gln Gln Leu Thr Trp Asp Leu Asn Arg Asn Val Thr
            35                  40                  45

Asp Ile Glu Cys Val Lys Asp Ala Asp Tyr Ser Met Pro Ala Val Asn
50                  55                  60

Asn Ser Tyr Cys Gln Phe Gly Ala Ile Ser Leu Cys Glu Val Thr Asn
65                  70                  75                  80

Tyr Thr Val Arg Val Ala Asn Pro Pro Phe Ser Thr Trp Ile Leu Phe
                85                  90                  95

Pro Glu Asn Ser Gly Lys Pro Trp Ala Gly Ala Glu Asn Leu Thr Cys
                100                 105                 110

```
Trp Ile His Asp Val Asp Phe Leu Ser Cys Ser Trp Ala Val Gly Pro
        115                 120                 125
Gly Ala Pro Ala Asp Val Gln Tyr Asp Leu Tyr Leu Asn Val Ala Asn
    130                 135                 140
Arg Arg Gln Gln Tyr Glu Cys Leu His Tyr Lys Thr Asp Ala Gln Gly
145                 150                 155                 160
Thr Arg Ile Gly Cys Arg Phe Asp Asp Ile Ser Arg Leu Ser Ser Gly
            165                 170                 175
Ser Gln Ser Ser His Ile Leu Val Arg Gly Arg Ser Ala Ala Phe Gly
                180                 185                 190
Ile Pro Cys Thr Asp Lys Phe Val Val Phe Ser Gln Ile Glu Ile Leu
        195                 200                 205
Thr Pro Pro Asn Met Thr Ala Lys Cys Asn Lys Thr His Ser Phe Met
    210                 215                 220
His Trp Lys Met Arg Ser His Phe Asn Arg Lys Phe Arg Tyr Glu Leu
225                 230                 235                 240
Gln Ile Gln Lys Arg Met Gln Pro Val Ile Thr Glu Gln Val Arg Asp
            245                 250                 255
Arg Thr Ser Phe Gln Leu Leu Asn Pro Gly Thr Tyr Thr Val Gln Ile
                260                 265                 270
Arg Ala Arg Glu Arg Val Tyr Glu Phe Leu Ser Ala Trp Ser Thr Pro
        275                 280                 285
Gln Arg Phe Glu Cys Asp Gln Glu Glu Gly Ala Asn Thr Arg Ala Trp
    290                 295                 300
Arg Thr Ser Leu Leu Ile Ala Leu Gly Thr Leu Leu Ala Leu Val Cys
305                 310                 315                 320
Val Phe Val Ile Cys Arg Arg Tyr Leu Val Met Gln Arg Leu Phe Pro
            325                 330                 335
Arg Ile Pro His Met Lys Asp Pro Ile Gly Asp Ser Phe Gln Asn Asp
                340                 345                 350
Lys Leu Val Val Trp Glu Ala Gly Lys Ala Gly Leu Glu Glu Cys Leu
        355                 360                 365
Val Thr Glu Val Gln Val Val Gln Lys Thr
    370                 375
```